United States Patent
Miyake et al.

(10) Patent No.: US 11,578,030 B2
(45) Date of Patent: Feb. 14, 2023

(54) ORGANIC AMINE COLLECTION METHOD

(71) Applicant: ASAHI KASEI KABUSHIKI KAISHA, Tokyo (JP)

(72) Inventors: Nobuhisa Miyake, Tokyo (JP); Masaaki Shinohata, Tokyo (JP); Yusuke Sakurai, Tokyo (JP); Yusuke Ishii, Tokyo (JP); Takeharu Sasaki, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 255 days.

(21) Appl. No.: 16/954,318

(22) PCT Filed: Dec. 27, 2018

(86) PCT No.: PCT/JP2018/048087
§ 371 (c)(1),
(2) Date: Jun. 16, 2020

(87) PCT Pub. No.: WO2019/131855
PCT Pub. Date: Jul. 4, 2019

(65) Prior Publication Data
US 2021/0155573 A1  May 27, 2021

(30) Foreign Application Priority Data

Dec. 27, 2017 (JP) .............................. JP2017-252607
Jan. 30, 2018 (JP) .............................. JP2018-014143

(51) Int. Cl.
*C07C 209/84* (2006.01)
*C07C 209/86* (2006.01)

(52) U.S. Cl.
CPC .......... *C07C 209/84* (2013.01); *C07C 209/86* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 3,499,035 | A | 3/1970 | Kober et al. |
| 4,137,266 | A | 1/1979 | Cassata |
| 4,654,443 | A | 3/1987 | Marks et al. |
| 5,902,459 | A | 5/1999 | Gagnon et al. |
| 6,673,960 | B1 | 1/2004 | Schwarz et al. |
| 2002/0010369 | A1 | 1/2002 | Dai et al. |
| 2003/0012710 | A1 | 1/2003 | Nishida et al. |
| 2008/0262263 | A1 | 10/2008 | Wolfert et al. |
| 2011/0021836 | A1 | 1/2011 | Bock et al. |
| 2011/0092731 | A1 | 4/2011 | Shinohata et al. |
| 2012/0271067 | A1* | 10/2012 | Shimokawatoko ... C07C 209/62  568/876 |
| 2013/0041182 | A1 | 2/2013 | Su |
| 2014/0073811 | A1 | 3/2014 | Takamatsu et al. |
| 2016/0052874 | A1 | 2/2016 | Shinohata et al. |

FOREIGN PATENT DOCUMENTS

| | | |
|---|---|---|
| CA | 2335068 A1 | 12/1999 |
| CN | 1251570 A | 4/2000 |
| CN | 1305456 A | 7/2001 |
| CN | 1802344 A | 7/2006 |
| DE | 2703313 A1 | 8/1978 |
| EP | 0976719 A1 | 2/2000 |
| GB | 795639 A | 5/1958 |
| JP | 50-142501 A | 11/1975 |
| JP | 54-130525 A | 10/1979 |
| JP | 58-048538 B2 | 10/1983 |
| JP | 58-201751 A | 11/1983 |
| JP | 10-279539 A | 10/1998 |
| JP | 2002-173471 A | 6/2002 |
| JP | 2002-518369 A | 6/2002 |
| JP | 2011-516593 A | 5/2011 |
| JP | 2011-132175 A | 7/2011 |
| JP | 5240678 B2 | 7/2013 |
| JP | 5563816 B2 | 7/2014 |
| JP | 5563886 B2 | 7/2014 |

(Continued)

OTHER PUBLICATIONS

Supplementary European Search Report issued in corresponding European Patent Application No. 18896283.1, dated Dec. 2, 2020.

(Continued)

*Primary Examiner* — Sudhakar Katakam
*Assistant Examiner* — Jennifer C Sawyer
(74) *Attorney, Agent, or Firm* — Morgan, Lewis & Bockius LLP

(57) ABSTRACT

A method is provided for collecting a compound of formula (III) (in which R31 is a monovalent to trivalent organic group and n31 is an integer of 1 to 3) from a liquid phase component that is formed as a by-product in a method for producing a compound of general formula (I) (in which R11 is a monovalent to trivalent organic group and n 11 is an integer of 1 to 3), wherein the collection method contains steps (1) to (3) or steps (A) and (B), and step (4). Step (1): a step for reacting the liquid phase component with at least one active hydrogen-containing compound in a reactor. Step (2): a step for returning a condensed liquid obtained by cooling gas phase components in the reactor to the reactor. Step (3): a step for discharging gas phase components that are not condensed in the step (2) to the outside of the reactor. Step (A): a step for mixing the liquid phase component, water, and a compound of general formula (III). Step (B): a step for reacting the liquid phase component with water inside the reactor. Step (4): a step for discharging, as a liquid phase component inside the reactor, the reaction liquid containing the compound of general formula (III) to the outside of the reactor.

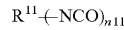

(I)

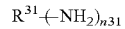

(III)

20 Claims, 12 Drawing Sheets

(56) References Cited

FOREIGN PATENT DOCUMENTS

| WO | 2004/108656 A1 | 12/2004 |
| WO | 2007/036479 A1 | 4/2007 |
| WO | 2009/127591 A2 | 10/2009 |
| WO | 2009/130842 A1 | 10/2009 |
| WO | 2009/139062 A1 | 11/2009 |
| WO | 2011/078000 A1 | 6/2011 |
| WO | 2012/157366 A1 | 11/2012 |
| WO | 2014/157636 A1 | 10/2014 |

OTHER PUBLICATIONS

International Search Report issued in corresponding International Patent Application No. PCT/JP2018/048087, dated Mar. 26, 2019.
Extended European Search Report issued in corresponding European Patent Application No. 21169951.7, dated May 17, 2021.
Written Opinion issued in corresponding International Patent Application No. PCT/JP2018/048087, dated Mar. 26, 2019.

* cited by examiner

ORGANIC AMINE COLLECTION METHOD

TECHNICAL FIELD

The present invention relates to a method for collecting an active ingredient such as an organic amine compound or an aromatic hydroxy compound from a liquid phase component generated when an isocyanate is produced.

The present invention claims priority on the basis of Japanese Patent Application No. 2017-252607, filed in Japan on Dec. 27, 2017, and, Japanese Patent Application No. 2018-014143, filed in Japan on Jan. 30, 2018, the contents of which are incorporated herein by reference.

BACKGROUND OF THE INVENTION

An isocyanate compound having at least one isocyanate group (NCO group) is industrially and widely used as a raw material used to produce a polyurethane, a polyurea or the like.

As a method for producing isocyanate compounds, methods in which organic amine compounds as the main raw materials, and a phosgene as a secondary raw material, are used, and methods in which organic amine compounds, and carbonic acid esters or urea are used are known.

In the method for producing isocyanate compounds, it is known that the resultant carbamates, NCO compounds, or intermediates thereof cause polymerization reactions such as multimerization, biuret-forming reaction, or allophanate-forming reaction, and compositions containing by-products resulting from the polymerization reactions are obtained after separating the compound (I). The by-products are by-products derived from isocyanate compounds and organic amine compounds that are raw materials of the isocyanate compounds, and are advantageous industrially if the by-products can be recovered as active ingredients.

In addition, the compositions containing the by-products may become a highly viscous liquid or solid at around room temperature, and occlusion or the like may occur in the continuous production of the isocyanate compounds.

For example, Patent Document 1 discloses a method of separating isocyanates from diisocyanate-containing organic residues under specific temperature and pressure conditions and transferring the residues forcibly.

Patent Documents 2 to 6 disclose methods for conducting post-treatment of residues resulting from the production of isocyanates.

Patent Document 7 discloses a method for conducting post-treatment of a residue resulting from the production of isocyanates in which the entire amount of gas components formed as by-products are absorbed by alkali metal as carbonates.

Patent Document 8 discloses a method for conducting post-treatment by reacting a distillate residue formed in the synthesis of a tolylene diisocyanate with water, in which the distillate residue is reacted with water continuously or semi-continuously in a reverse-mixing reactor in the presence of hydrolysate.

Patent Document 9 discloses a decomposition and collection method in which high-temperature and high-pressure water containing ammonia and/or aliphatic amines is contacted with an isocyanate-based compound to collect the resultant as a raw material of the isocyanate-based compound.

DOCUMENTS OF RELATED ART

Patent Documents

Patent Document 1: International Patent Application Publication No. WO 2007/036479
Patent Document 2: International Patent Application Publication No. WO 2009/0127591
Patent Document 3: Japanese Patent No. 5563816
Patent Document 4: Japanese Patent No. 5563886
Patent Document 5: Japanese Patent No. 5240678
Patent Document 6: International Patent Application Publication No. WO 2009/130842
Patent Document 7: Japanese Examined Patent Application Publication No. Sho 58-048538
Patent Document 8: Japanese Translation of PCT International Application Publication No. 2002-518369
Patent Document 7: Japanese Unexamined Patent Application Publication No. 2002-173471

SUMMARY OF THE INVENTION

Problems to be Solved by the Invention

However, in the method disclosed in Patent Document 1, when a diisocyanate-containing organic residue is transferred to a device to be used to separate diisocyanates, the diisocyanate-containing organic residue often has a high viscosity, which makes it difficult to transfer the diisocyanate-containing organic residue.

In the methods disclosed in Patent Documents 2 to 7, an isocyanate compound is not sufficiently obtained, and, after the treatment step is conducted, a carbamate is further required to be thermally-decomposed to obtain an isocyanate. Even if the thermal-decomposition step is conducted from the viewpoint of the reaction principle, there is a problem in which by-products are produced. In addition, the method in which a carbonic acid ester is added has an essential problem in which an organic amine compound formed by treating an isocyanate compound and a carbonic acid ester are reacted to form a carbamate that promotes the side reaction.

The method disclosed in Patent Document 8 has a problem in which the reaction efficiency is low and it takes a long time till the reaction is completed.

The method disclosed in Patent Document 9 has a problem in which the reaction efficiency depends on the interface contact efficiency between an aqueous phase and an organic phase, and that the liquid-liquid separation occurs and the reaction efficiency is low in the area where the agitation power is not available.

The present invention aims to provide a method for efficiently collecting useful components such as organic amines and aromatic hydroxy compounds from liquid phase components containing high-boiling-point compounds after collecting isocyanates.

Means to Solve the Problems

The present invention involves the following embodiments.
(1) A method for collecting a compound of general formula (III) from a liquid phase component that is formed as a by-product in a method for producing a compound of general formula (I), including:

step (1): a step for reacting the liquid phase component with at least one active hydrogen-containing compound in a reactor;

step (2): a step for returning a condensed liquid obtained by cooling gas phase components in the reactor to the reactor;

step (3): a step for discharging gas phase components that are not condensed in the step (2) to the outside of the reactor; and step (4): a step for discharging, as a liquid phase component inside the reactor, the reaction liquid containing the compound of general formula (III) to the outside of the reactor.

$$R^{11}\text{-}(NCO)_{n11} \quad (I)$$

In the general formula (I), $R^{11}$ represents a monovalent to trivalent organic group, and nI 1represents an integer of 1 to 3.

$$R^{31}\text{-}(NH_2)_{n31} \quad (III)$$

In the general formula (III), $R^{31}$ represents a monovalent to trivalent organic group, and n31 represents an integer of 1 to 3.

(2) The collection method according to (1), wherein the active hydrogen-containing compound is selected from the group consisting of water, urea, alcohols, aromatic hydroxy compounds and organic primary amines.

(3) A method for collecting a compound of the general formula (III) from a liquid phase component that is formed as a by-product, including:

step (A): a step for mixing the liquid phase component, water, and the compound of general formula (III);

step (B): a step for reacting the liquid phase component with water in a reactor; and step (4): a step for discharging, as a liquid phase component inside the reactor, the reaction liquid containing the compound of general formula (III) to an outside of the reactor.

$$R^{11}\text{-}(NCO)_{n11} \quad (I)$$

In the general formula (I), $R^{11}$ represents a monovalent to trivalent organic group, and n11 represents an integer of 1 to 3.

$$R^{31}\text{-}(NH_2)_{n31} \quad (III)$$

In the general formula (III), $R^{31}$ represents a monovalent to trivalent organic group, and n31 represents an integer of 1 to 3.

(4) The collection method according to any one of (1) to (3), wherein the method for producing a compound of general formula (I) is a method in which the compound of general formula (I) is produced from a carbonic acid derivative, a hydroxy compound and the compound of general formula (III).

(5) The collection method according to any one of (1) to (4), wherein the liquid phase component that is formed as a by-product in the method for producing the compound of general formula (I) is a liquid phase component extracted from a thermal decomposition reactor when a gas phase component containing the compound of general formula (I) generated by supplying a liquid containing a carbamate produced from a carbonic acid derivative, a hydroxy compound and the compound of general formula (III) to the thermal decomposition reactor and then subjecting the carbamate to thermal decomposition reaction is collected.

(6) The collection method according to (5), wherein the thermal decomposition reactor contains: a tubular reactor; and a separation tank in which the liquid phase component and the gas phase component containing the compound of general formula (I) are separated, wherein the flow rate per wetted perimeter of the tubular reactor is 10 kg/hour·m to 1000 kg/hour·m.

(7) The collection method according to (5) or (6), wherein the linear velocity of the gas phase component in a separation tank in which the liquid phase component and the gas phase component containing the compound of general formula (I) are separated is 10 m/second or less.

(8) The collection method according to any one of (5) to (7), wherein the liquid phase component extracted from the thermal decomposition reactor is supplied to the reactor in which the step (1) is conducted while maintaining the liquid phase component at a temperature of 150° C. to 350° C.

(9) The collection method according to any one of (1) to (8), wherein the liquid phase component contains a hydroxy compound.

(10) The collection method according to any one of (1) to (8), wherein the liquid phase component contains a compound having at least one group selected from the group consisting of a group of formula (II-1) and a group of formula (II-2).

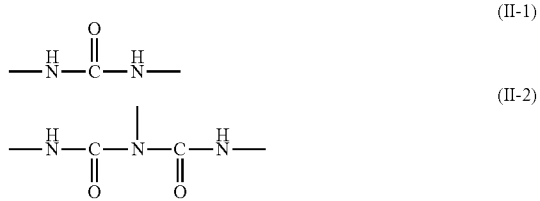

(11) The collection method according to (10), wherein the liquid phase component contains a hydroxy compound in an amount of 20% by mass to 70% by mass, relative to a total mass of the liquid phase component.

(12) The collection method according to any one of (1) to (11), wherein the liquid phase component has a viscosity at 150° C. of 100 mPa·s or less.

(13) The collection method according to any one of (1) to (12), wherein the reactor is at least one reactor selected from the group consisting of a tank-type reactor, an extruder and a thin-film evaporator.

(14) The collection method according to any one of (1), (2) and (4) to (12), wherein the at least one active hydrogen-containing compound is water, and the gas phase component discharged in the step (3) contains carbon dioxide.

(15) The collection method according to any one of (1), (2) and (4) to (12), wherein at least two of the active hydrogen-containing compounds are water and an aromatic hydroxy compound.

(16) The collection method according to any one of (1), (2) and (4) to (12), wherein at least two of the active hydrogen-containing compounds are urea and an aromatic hydroxy compound, and the gas phase component discharged in the step (3) contains carbon dioxide and ammonia.

(17) The collection method according to (14) or (15), wherein the condensed liquid in the step (2) is water.

(18) The collection method according to any one of (15) to (17), wherein the compound of the general formula (III) is further used as the active hydrogen-containing compound.

(19) The collection method according to any one of (1) to (18), further including:

step (5): a step for separating the compound of the general formula (III) from the reaction liquid obtained in the step (4); and step (6): a step for purifying the compound of the general formula (III).

(20) The collection method according to (19), wherein the compound of the general formula (III) is collected by distillation in the step (6), such that, relative to the total mass of the compound of the general formula (III), an amount of metallic components becomes 1000 ppm by mass or less and an amount of halogen atoms becomes 1000 ppm by mass or less.

(21) The collection method according to (19) or (20), wherein the compound of the general formula (III) collected in the step (6) is recycled to produce the compound of general formula (I).

(22) The collection method according to any one of (19) to (21), wherein the liquid phase component contains a compound having a group of general formula (IV), a compound of general formula (V) is separated in the step (5) together with the compound of the general formula (III) from the reaction liquid obtained in the step (4), and further including:

step (7): a step for purifying the compound of the general formula (V), wherein the step (7) is conducted after the step (6).

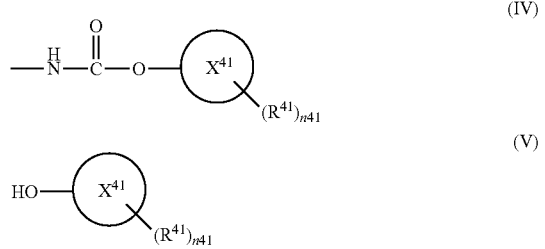

In the general formulae (IV) and (V), $X^{41}$ represents a C6-12 unsubstituted or substituted aromatic hydrocarbon ring or heteroaromatic ring, $R^{41}$ represents a C1-20 alkyl group, which may be substituted with at least one group selected from the group consisting of a phenyl group and a hydroxy phenyl group, an amino group, or a hydroxy group, n41 represents an integer of 0 to 4, and $R^{41}$ is identical to or different from each other when n41 is 2 or more.

(23) The collection method according to (22), wherein the compound of the general formula (V) is collected by distillation in the step (7), such that, relative to the total mass of the compound of the general formula (V), the amount of metallic components becomes 1000 ppm by mass or less and the amount of halogen atoms becomes 1000 ppm by mass or less.

(24) The collection method according to (22) or (23), wherein the compound of the general formula (V) collected in the step (7) is recycled to produce the compound of general formula (I).

Effects of the Invention

The present invention makes it possible to collect efficiently useful components such as organic amine compounds or aromatic hydroxy compounds from the liquid phase component containing the high-boiling point compound after collecting an isocyanate.

EMBODIMENTS FOR CARRYING OUT THE INVENTION

Figure 1:
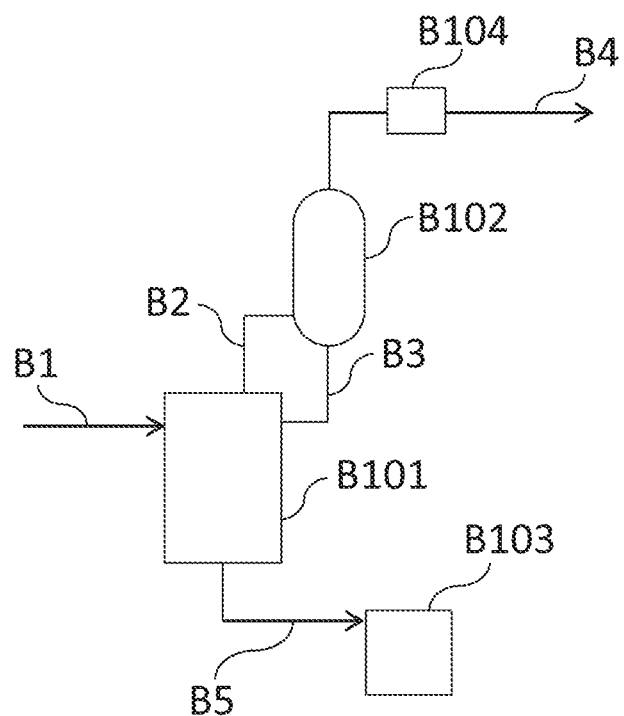
FIG. 1 is a schematic configuration drawing illustrating an example of a collection device to be used in the collection method according to the present invention.

Preferable embodiments according to the present invention will be described below. The present invention is not limited to the below-mentioned embodiments and may be modified in various ways within the summary thereof.

The terms "organic group", "aliphatic" and "aromatic" used in the present specification mean the same as those described in paragraphs [0017] to [0023] of International Patent Application Publication No. WO 2014/069605 (Reference Document 1).

Specifically, in the present specification, the terms mean those cited from "organic chemistry and biochemistry nomenclature" (published by Japanese Nankodo in 1992 as the revised second edition) containing all rules of organic chemistry and biochemistry published as a separate volume of "chemistry region" in 1980 based on Recommendations 1979, the volume encompassing the rules translated into Japanese, and all subsequent revisions and recomnnendations based thereon, when IUPAS Rules and Nomenclature rules stipulated by IUPAC and also described below (excepting the case where IUPAC Recommendations in other years is specially cited) is referred.

The term "organic" refers to general compounds which are objects of nomenclature disclosed in the nomenclature. The objects may be objects disclosed in Recommendations issued in 1993. The "organic" compounds which are objects of the nomenclature encompass organic metal compounds and metal complexes.

In the present embodiment, the terms "organic group" and "substituent group" refer to groups constituted by atoms free from metal atoms and/or metalloids, unless otherwise indicated particularly. In addition, an "organic compound", "organic group" or "substituent group", constituted by atoms selected from the group consisting of H (hydrogen atom), C (carbon atom), N (nitrogen atom), O (oxygen atom), S (sulfur atom), Cl (chlorine atom), Br (bromine atom), and I (iodine atom) are preferably used in the present embodiment.

The terms "aliphatic" and "aromatic" are used many times in the following description. It is described in the IUPAC Rules that organic compounds are classified into aliphatic compounds and aromatic compounds. The aliphatic compounds are aliphatic compounds based on IUPAC Recommendation in 1995. In the Recommendation, the aliphatic compounds are defined as "acyclic or cyclic, saturated or unsaturated carbon compounds, excluding aromatic compounds".

The term "aliphatic compound" used in the description of the present embodiment encompasses saturated or unsaturated, and chain or cyclic aliphatic compounds, and refers to "organic compound", "organic group" or "substituent group" constituted by atoms selected from the group consisting of H (hydrogen atom); C (carbon atom); N (nitrogen atom); O (oxygen atom); S (sulfur atom); Si (silicon atom); and halogen atoms such as Cl (chlorine atom), Br (bromine atom) and I (iodine atom).

In the case where an aromatic group such as an aralkyl group is bonded to an aliphatic group, it may be indicated as "an aliphatic group substituted with an aromatic group", or "a group constituted by an aliphatic group bonded with an aromatic group" depending on the reactivity in the present embodiment, because the reactivity of a group such as an aralkyl group is not similar to the reactivity of aromatic groups but extremely similar to that of aliphatic groups.

In addition, a non-aromatic reactive group encompassing an aralkyl group, an alkyl group, and the like, may be indicated as "an aliphatic group which may be substituted with an aromatic group", "an aliphatic group which may be bonded with an aromatic group", or the like.

Although the general formula of a compound used in the present specification is described in accordance with Nomenclature Rule stipulated by IUPAC, names of specific groups or exemplified compounds may be indicated by common names. In addition, all of numbers of atoms or substituent groups indicated in the present specification are integers.

In the present specification, the term "active hydrogen" refers to a hydrogen atom bonded with an oxygen atom, sulfur atom, nitrogen atom, silicon atom, or the like (excepting aromatic hydroxy group), or a hydrogen atom of a terminal methine group. The "active hydrogen" is, for example, a hydrogen included in an atomic group such as —OH group, —C(=O)OH group, —C(=O)H group, —SH group, —SO$_3$H group, —SO$_2$H group, —SOH group, —NH$_2$ group, —NH group, —SiH group, —C≡CH group, or the like. Examples of a compound having a hydroxy group (—OH group) include alcohols and aromatic hydroxy compounds.

The term "alcohol" used in the present specification means "compound in which a hydroxy group, —OH, is attached to a saturated carbon atom: R$_3$COH" described in the definition (Rule C-201) of IUPAC, and aromatic hydroxy compounds in which a hydroxy group is attached to an aromatic ring are not encompassed thereby.

The term "aromatic hydroxy compound" used in the present specification means phenol described in the definition (Rule C-202) of IUPAC "compound having one or more hydroxy groups attached to a benzene or other arene ring".

《Collection Method》

The organic amine collection method according to the first embodiment of the present invention is a method in which a compound of the general formula (III) shown below (hereinafter, which may be referred to as "compound (III)") is collected from a liquid phase component containing a high-boiling point compound that is formed as a by-product in the method for producing a compound of the general formula (I) shown below (hereinafter, which may be referred to as "compound (I)"), and contains the steps (1) to (4) described below.

Step (1): a step for reacting the liquid phase component containing the high-boiling point compound with at least one active hydrogen-containing compound in a reactor.

Step (2): a step for returning a condensed liquid obtained by cooling gas phase components in the reactor to the reactor.

Step (3): a step for discharging gas phase components that are not condensed in the step (2) to the outside of the reactor.

Step (4): a step for discharging, as a liquid phase component inside the reactor, the reaction liquid containing the compound of general formula (III) to the outside of the reactor.

  (I)

In the general formula (I), $R^{11}$ represents a monovalent to trivalent organic group, and n11 represents an integer of 1 to 3.

  (III)

In the general formula (III), $R^{31}$ represents a monovalent to trivalent organic group, and n31 represents an integer of 1 to 3.

Each of the compounds used or generated in the collection method according to the present embodiment will be described below.

<Compound (I)>

A compound (I) is a compound of general formula (I), and an isocyanate compound having at least one isocyanate group.

  (I)

In the general formula (I), $R^{11}$ represents a monovalent to trivalent organic group, and n11 represents an integer of 1 to 3.

[$R^{11}$]

In the general formula (I), $R^{11}$ represents a monovalent to trivalent organic group. Among these, $R^{11}$ preferably represents a C1-20 monovalent to trivalent aliphatic group or a C6-20 monovalent to trivalent aromatic group, and preferably a C1-20 monovalent to trivalent aliphatic hydrocarbon group, a C6-20 monovalent to trivalent aromatic group, or a C1-20 group formed by binding, via an ester group, at least two groups selected from the group consisting of the aliphatic hydrocarbon groups and the aromatic groups.

($R^{11}$: Aliphatic Hydrocarbon Group)

In the case where $R^1$ is an aliphatic hydrocarbon group, $R^{11}$ is preferably a linear or branched alkyl group, alkylene group or alkanetriyl group, a cycloalkyl group, a cycloalkylene group or a cycloalkanetriyl group, or a group formed by the alkyl group, the alkylene group or the alkanetriyl group, with the cycloalkyl group, the cycloalkylene group or the cycloalkanetriyl group, and more preferably a linear or branched alkylene group or alkanetriyl group, a cycloalkylene group or a cycloalkanetriyl group, or a group formed by the alkylene group or the alkanetriyl group, with the cycloalkyl group, the cycloalkylene group or the cycloalkanetriyl group.

Examples of the linear or branched alkylene group include methylene group, ethylene group, propylene group, trimethylene group, pentylene group, n-hexylene group, and decamethylene group.

Examples of the cycloalkylene group include cyclobutylene group, and cyclohexylene group.

Examples of the linear or branched alkanetriyl group include hexanetriyl group, nonanetriyl group, and decanetriyl group.

Examples of the cycloalkanetriyl group include cyclopropanetriyl group, cyclobutanetriyl group, cyclopentanetriyl group, and cyclohexanetriyl group.

In the case where $R^{11}$ is an aliphatic hydrocarbon group, specific examples of the compound (I) include aliphatic diisocyanates, aliphatic triisocyanates, and substituted alicyclic polyisocyanates.

Examples of the aliphatic diisocyanates include ethylene diisocyanate, diisocyanatopropane (each isomers), diisocyanatobutane (each isomers), diisocyanatopentane (each isomers), diisocyanatohexane (each isomers), diisocyanatodecane (each isomers), isophorone diisocyanate (each isomers), and dicyclohexylmethane diisocyanate (each isomers).

Examples of the aliphatic tri isocyanates include triisocyanatohexane (each isomers), triisocyanatononane (each isomers), and triisocyanatodecane (each isomers).

Examples of the substituted alicyclic polyisocyanates include diisocyanatocyclobutane (each isomers), diisocyanatocyclohexane (each isomers), 3-isocyanatomethyl-3,5,5-trimethylcyclohexyl isocyanate (at least one isomer of cis form and trans form), and methylene bis(cyclohexyl isocyanate) (each isomers).

($R^{11}$: Aromatic Group)

In the case where $R^{11}$ is an aromatic group, a group having a C6-13 aromatic ring which may have a substituent group is preferable. Examples of the substituent group include alkyl group, aryl group, and an aralkyl group. The aromatic ring may be an aromatic hydrocarbon ring or a heteroaromatic ring, and specific examples thereof include benzene ring, naphthalene ring, and pyridine ring.

In the case where $R^{11}$ is an aromatic group, specific examples of the compound (I) include aromatic diisocyanates and aromatic triisocyanates.

Examples of the aromatic diisocyanates include diisocyanatobenzene (each isomers), diisocyanatotoluene (each isomers), methylene dianiline (each isomers), diisocyanatomesitylene (each isomers), diisocyanatobiphenyl (each isomers), diisocyanatodibenzyl(each isomers), bis(isocyanatophenyl)propane (each isomers), bis(isocyanatophenyl) ether (each isomers), bis(isocyanatophenoxyethane) (each isomers), diisocyanatoxylene (each isomers), diisocyanatoanisole (each isomers), diisocyanatophenetole (each isomers), diisocyanatonaphthalene (each isomers), diisocyanatomethylbenzene (each isomers), diisocyanatomethylpyridine (each isomers), diisocyanatomethylnaphthalene (each isomers), diisocyanatodiphenylmethane (each isomers), and tetramethylxylylene diisocyanate (each isomers).

Examples of aromatic triisocyanates include triisocyanatobenzene (each isomers), triisocyanatomethylbenzene (each isomers), tris(isocyanatopropan-yl)benzene (each isomers), tris(isocyanatopropan-yl)-methylbenzene (each isomers), tris(isocyanatomethyl)-methylbenzene (each isomers), and ((isocyanatophenylene)bis(methylene)) bis (isocyanate benzene) (each isomers).

($R^{11}$: C1-20 Group Formed by Binding, Via an Ester Group, at Least Two Groups Selected from the Group Consisting of the Aliphatic Hydrocarbon Groups and the Aromatic Groups)

In the case where $R^{11}$ is a C1-20 group formed by binding, via an ester group, at least two groups selected from the group consisting of the aliphatic hydrocarbon groups and the aromatic groups, specific examples of the compound (I) include 2-isocyanato-ethyl acrylate, 2-isocyanato-ethyl 2-methylacrylate, 2-isocyanato-propyl acrylate, 2-isocyanato-propyl 2-methylacrylate, 3-isocyanato-propyl acrylate, 3-isocyanato-propyl 2-methylacrylate, 4-isocyanato-butyl acrylate, 4-isocyanato-butyl 2-methylacrylate, 5-isocyanato-pentyl acrylate, 5-isocyanato-pentyl 2-methylacrylate, 6-isocyanato-hexyl acrylate, 6-isocyanato-hexyl 2-methylacrylate, 8-isocyanato-octyl acrylate, 8-isocyanato-octyl 2-methylacrylate, 10-isocyanato-decyl acrylate, 10-isocyanato-decyl 2-methylacrylate, 11-isocyanato-undecyl acrylate, 11-isocyanato-undecyl 2-methylacrylate, 12-isocyanato-dodecyl acrylate, 12-isocyanato-dodecyl 2-methylacrylate, lysinemethyl ester diisocyanate, lysineethyl ester diisocyanate, 2-isocyanatoethyl-2,5-diisocyanatopentanoate, 2-isocyanatoethyl-2,6-diisocyanatohexanoate, bis(2-isocyanatoethyl)-2-isocyanatobutanedioate, bis(2-isocyanatoethyl)-2-isocyanatopentanedioate, and tris(2-isocyanatoethyl)hexane-1,3,6-tricarboxylate.

[n11]

In the general formula (I), n11 represents the number of isocyanate groups, and is an integer of 1 to 3. n11 is preferably 2 or 3.

Among these, the compound (I) is preferably diisocyanatohexane, diisocyanatotoluene, diisocyanatomethyltrimethylcyclohexane, dicyclohexylmethane diisocyanate, diphenylmethane diisocyanate, isophorone diisocyanate, hexamethylene diisocyanate, pentamethylene diisocyanate, xylylene diisocyanate, bis(isocyanatopropyl)benzene, bis(isocyanatopropyl)cyclohexane, or isocyanatomethyloctane diisocyanate.

<Compound (III)>

The compound (III) is a compound of the general formula (III), and an amino group-containing compound having at least one amino group.

(III)

In the general formula (III), $R^{31}$ represents a monovalent to trivalent organic group, and n31 represents an integer of 1 to 3.

[$R^{31}$]

In the general formula (III), $R^{31}$ represents a monovalent to trivalent organic group. Examples of $R^{31}$ include the same groups as those mentioned as $R^{11}$.

($R^{31}$: Aliphatic Hydrocarbon Group)

In the case where $R^{31}$ is an aliphatic hydrocarbon group, specific examples of the compound (III) include aliphatic diamines, aliphatic triamines, and substituted alicyclic polyamines.

Examples of the aliphatic diamines include ethylenediamine, diaminopropane (each isomers), diaminobutane (each isomers), diaminopentane (each isomers), diaminohexane (each isomers), and diaminodecane (each isomers).

Examples of the aliphatic triamines include triaminohexane (each isomers), triaminononane (each isomers), and triaminodecane (each isomers).

Examples of the substituted alicyclic polyamines include diaminocyclobutane (each isomers), diaminocyclohexane (each isomers), 3-aminomethyl-3,5,5-trimethylcyclohexylamine (at least one isomer of cis form and trans form), and methylenebis(cyclohexylamine) (each isomers).

($R^{31}$: Aromatic Group)

In the case where $R^{31}$ is an aromatic group, specific examples of the compound (III) include aromatic diamines and aromatic triamines.

Examples of the aromatic diamines include diaminobenzene (each isomers), diaminotoluene (each isomers), methylene dianiline (each isomers), diaminomesitylene (each isomers), diaminobiphenyl (each isomers), diaminodibenzyl (each isomers), bis(aminophenyl)propane (each isomers), bis(aminophenyl)ether (each isomers), bis(aminophenoxyethane) (each isomers), diaminoxylene (each isomers), diaminoanisole (each isomers), diaminophenetole (each isomers), diaminonaphthalene (each isomers), diaminomethylbenzene (each isomers), diaminomethylpyridine (each isomers), diaminomethylnaphthalene (each isomers), diaminodiphenylmethane (each isomers), and tetramethylxylylenediamine (each isomers).

Examples of the aromatic triamines include triaminobenzene (each isomers), triaminomethylbenzene (each isomers), tris(aminopropan-yl)benzene (each isomers), tris(aminopropan-yl)-methylbenzene (each isomers), tris(aminomethyl)-methylbenzene (each isomers), and ((aminophenylene)bis(methylene)) bis(aminebenzene) (each isomers).

($R^{31}$: C1-20 Group Formed by Binding, Via an Ester Group, at Least Two Groups Selected from the Group Consisting of the Aliphatic Hydrocarbon Groups and the Aromatic Groups)

In the case where $R^{31}$ is a C1-20 group formed by binding, via an ester group, at least two groups selected from the group consisting of the aliphatic hydrocarbon groups and the aromatic groups, specific examples of the compound (III) include 2-aminoethyl acrylate, 2-aminoethyl 2-methyl-acrylate, 2-aminopropyl acrylate, 2-aminopropyl 2-methyl-acrylate, 3-aminopropyl acrylate, 3-aminopropyl 2-methyl-acrylate, 4-aminobutyl acrylate, 4-aminobutyl 2-methyl-acrylate, 5-aminopentyl acrylate, 5-aminopentyl 2-methyl-acrylate, 6-aminohexyl acrylate, 6-aminohexyl 2-methyl-acrylate, 8-aminooctyl acrylate, 8-aminooctyl 2-methyl-acrylate, 10-aminodecyl acrylate, 10-aminodecyl 2-methyl-acrylate, 11-aminoundecyl acrylate, 11-aminoundecyl 2-methyl-acrylate, 12-aminododecyl acrylate, 12-aminododecyl 2-methyl-acrylate, lysinemethyl ester diamine, lysineethyl ester diamine, 2-aminoethyl-2,5-diaminopentanoate, 2-aminoethyl-2,6-diaminohexanoate, bis(2-aminoethyl)-2-aminobutane dioate, bis(2-aminoethyl)-2-aminopentane dioate, and tris(2-aminoethyl)hexane-1,3,6-tricarboxylate.

[n31]

In the general formula (III), n31 represents the number of amino groups and is an integer of 1 to 3. n31 is preferably 2 or 3.

Among these, the compound (111) is preferably diaminohexane, diaminotoluene, diaminomethyltrimethylcyclohexane, dicyclohexylmethane diamine, diphenylmethane diamine, isophorone diamine, hexamethylene diamine, pentamethylene diamine, xylylene diamine, bis(aminopropyl)benzene, bis(aminopropyl)cyclohexane, or aminomethyloctane diamine.

<High-Boiling Point Compound>

The high-boiling point compound is a compound that is formed as a by-product in the method for producing the compound (I), and that is not formed as a gas phase component to be extracted from a thermal decomposition reactor in the production step of the compound (I). Although the boiling point of the high-boiling point compound is not particularly limited, the boiling point thereof is, for example, 300° C. or more at an operation pressure of the thermal decomposition reactor.

<Method for Producing the Compound (I)>

The method for producing the compound (I) is preferably a method in which the compound (I) is produced from a carbonic acid derivative, a hydroxy compound and a compound (III).

The liquid phase component containing a high-boiling point compound that is formed as a by-product in the method for producing the compound (I) is preferably a liquid phase component extracted from a thermal decomposition reactor when a liquid containing a carbamate obtained by reacting a carbonic acid derivative, a hydroxy compound and a compound (III) is supplied to the thermal decomposition reactor to subject the carbamate to thermal decomposition reaction, followed by collecting a gas phase component containing the resultant compound (I).

[Carbonic Acid Derivative]

Examples of the carbonic acid derivative include urea, N-unsubstituted carbamic acid esters and carbonic acid esters.

(N-Unsubstituted Carbamic Acid Ester)

Examples of the N-unsubstituted carbamic acid esters include ethyl N-unsubstituted carbamate, butyl N-unsubstituted carbamate, hexyl N-unsubstituted carbamate, octyl N-unsubstituted carbamate, and phenyl N-unsubstituted carbamate.

The term "N-unsubstituted" means $H_2N-COOR$ (R represents a monovalent hydrocarbon group), and is used to clarify the difference from the structure $R'-NH-COOR$ (in which R and R' each independently represents a monovalent hydrocarbon group) in which one hydrogen atom bonded to a nitrogen atom is substituted with a hydrocarbon group.

(Carbonic Acid Ester)

Examples of the carbonic acid ester include dimethyl carbonate, diethyl carbonate, dibutyl carbonate, dihexyl carbonate, dioctyl carbonate, diphenyl carbonate, and di(m-ethylphenyl) carbonate.

Among these, the carbonic acid derivative is preferably urea, or a carbonic acid ester such as diphenyl carbonate or dibutyl carbonate, and is more preferably urea.

[Hydroxy Compound]

Examples of the hydroxy compound include alcohols and aromatic hydroxy compounds. Among these, the hydroxy compound is preferably an aromatic hydroxy compound.

(Alcohol)

Examples of the alcohol include methanol, ethanol, propanol (each isomers), butanol (each isomers), pentanol (each isomers), hexanol (each isomers), heptanol (each isomers), octanol (each isomers), nonanol (each isomers), decanol (each isomers), dodecanol (each isomers), octadecanol (each isomers), cyclopentanol, cyclohexanol, phenyl methanol, phenylethanol (each isomers), phenylpropanol (each isomers), phenyl butanol (each isomers), phenylpentanol (each isomers), phenylhexanol (each isomers), phenylheptanol (each isomers), phenyloctanol (each isomers), and phenylnonanol (each isomers).

(Aromatic Hydroxy Compound)

Examples of the aromatic hydroxy compound include phenol, methylphenol (each isomers), propylphenol (each isomers), butylphenol (each isomers), pentylphenol (each isomers), octylphenol (each isomers), nonylphenol (each isomers), phenylphenol (each isomers), phenylmethylphenol (each isomers), phenylpropylphenol (each isomers), and phenoxyphenol (each isomers).

In the method for producing a compound (I) from a carbonic acid derivative, a hydroxy compound and a compound (III), a carbamate is produced from the carbonic acid derivative, the hydroxy compound and the compound (III), and then the carbamate is subjected to thermal decomposition to obtain the compound (I). As the method for producing the carbamate, the following method i) or ii) may be adopted. In the production method according to the present embodiment, both the method i) and the method ii) may be adopted in combination.

i) Method for producing a carbamate in which a compound (III), a carbonic acid derivative and a hydroxy compound are reacted simultaneously.

ii) Method for producing a carbamate in which at least one compound selected from the group consisting of urea and N-unsubstituted carbamic acid esters is used as a carbonic acid derivative, the method containing: a step of producing a ureido-containing compound by reacting a compound (III) and the carbonic acid derivative (hereinafter, may be referred to as "step a"); and a step of producing a carbamate by reacting the ureido-containing compound and a hydroxy compound (hereinafter, may be referred to as "step b").

[Method i)]

In the method i), the stoichiometric ratio (molar ratio) of the hydroxy compound, relative to amino groups in the compound (III) used, may be 1 to 500.

The stoichiometric ratio (molar ratio) of the carbonic acid derivative, relative to amino groups in the compound (III) used, may be 1 to 100.

The reaction temperature may be 100° C. to 350° C.

The reaction pressure may be 0.01 kPa to 10 MPa (absolute pressure).

In the case where at least one compound selected from the group consisting of urea and N-unsubstituted carbamic acid esters is used as the carbonic acid derivative, the reaction is required to be conducted while removing ammonia generated as a by-product outside the system as far as possible so as to increase the yield of the carbamate. Examples of the method for removing ammonia outside the system include a reaction distillation method, an inert gas-replacement method, a membrane separation method, and an adsorption separation method. A solvent or a catalyst may be used, as needed in the reaction.

The reaction time (the residence time in the case of a continuous reaction) is 0.01 hours to 100 hours, and the reaction time may be determined depending on the production amount of the carbamate which is a target compound of the method i).

[Method ii)]

(Step a))

In the method ii), the step a) is a step in which a reaction mixture containing a ureido-containing compound is obtained by reacting a compound (III) and a carbonic acid derivative. In the step a), the stoichiometric ratio (molar ratio) of the carbonic acid derivative, relative to amino groups in the compound (III) used, may be 1 to 100.

The reaction temperature may be 30° C. to 250° C.

The reaction pressure may be 0.01 kPa to 10 MPa (absolute pressure).

The reaction time (the residence time in the case of a continuous method) may be 0.001 hours to 100 hours, and the reaction may be terminated after the production of a predetermined amount of the ureido-containing compound is confirmed. In the step a), a catalyst or a solvent may be used, as needed. Among these, a hydroxyl compound to be used in the subsequent step b) is preferably used as a solvent.

(Sep b))

In the method ii), the step b) is a step in which a carbamate is produced by reacting the ureido-containing compound obtained in the step a) and a hydroxy compound. In the case where a hydroxy compound is used as a reaction solvent in the step a), the step b) may be directly conducted by using the reaction liquid obtained in the step a).

The stoichiometric ratio (molar ratio) of the hydroxy compound used, relative to ureidio in the ureido-containing compound used, may be 1 to 500.

The reaction temperature may be 100° C. to 350° C.

The reaction pressure may be 0.01 kPa to 10 MPa (absolute pressure).

The reaction is required to be conducted while removing ammonia generated as a by-product outside the system as far as possible so as to increase the yield of the carbamate. Examples of the method for removing ammonia outside the system include the same methods as those mentioned in the "[Method i]]".

A solvent and/or a catalyst may be used, as needed in the step b).

The reaction time (the residence time in the case of a continuous method) may be 0.001 hours to 100 hours, and may be determined depending on the production amount of the carbamate which is a target compound of the step b).

In any of the method i) and the method ii), additional steps may be further conducted, as needed. Examples of the additional steps include: a step in which the carbamate obtained in the above-mentioned step is subjected to an ester-exchange reaction using a hydroxy compound which is of a different kind from the hydroxyl compound used in the above-mentioned method to obtain a different kind of carbamate; a step in which the partial or entire amount of the hydroxy compound is separated from the reaction liquid obtained in the above-mentioned method; and a step in which ammonia generated in the above-mentioned method is collected.

The carbamate produced by the method i) and the method ii) is a compound of the following general formula (XII) (hereinafter, may be referred to as "compound (XII)").

In the general formula (XII), $R^{121}$ represents a monovalent to trivalent organic group. $R^{122}$ is a monovalent organic group. N121 is an integer of 1 to 3.

Examples of $R^{121}$ include the same groups as those mentioned as $R^{11}$ of the compound (I).

$R^{122}$ is a group formed by removing a hydroxyl group from the hydroxy compound. That is, $R^{122}$ is a monovalent aliphatic group or aromatic group, and preferably a C1-20 linear, branched or cyclic alkyl group, a C6-13 aryl group, or a C7-20 aralkyl group.

Examples of the C1-20 linear or branched alkyl group include methyl group, ethyl group, propyl group, butyl group, pentyl group, heptyl group, octyl group, nonyl group, decyl group, dodecyl group, and octadecyl group.

Examples of the C1-20 cyclic alkyl group include cyclopentyl group and cyclohexyl group.

Examples of the C6-13 aryl group include phenyl group, tolyl group, ethylphenyl group, propylphenyl group, butylphenyl group, pentylphenyl group, octylphenyl group, nonylphenyl group, biphenyl group, phenylethylphenyl group, phenylpropylphenyl group, and phenoxyphenyl group.

Examples of the C7-20 aralkyl group include benzyl group, phenylmethyl group, phenylpropyl group, phenylbutyl group, phenylpentyl group, phenylhexyl group, phenylheptyl group, phenyloctyl group, and phenylnonyl group.

The carbamate-containing liquid containing a carbamate prepared by the method i) or ii) is supplied to the thermal decomposition reactor to collect a gas phase component containing the resultant compound (1).

The reaction temperature in which the carbamate is subjected to thermal decomposition may be 100° C. to 350° C.

The reaction pressure is usually 10 Pa to $1 \times 10^6$ Pa (absolute pressure).

Although a catalyst is not always required, and it is preferable that a catalyst be not used, a catalyst may be used to decrease the reaction temperature or to terminate the reaction promptly. The amount of the catalyst to be used may be, relative to the mass of the carbamate, 0.01% by mass to 30% by mass. Specific examples of the catalyst include organic tin compounds, copper family metal compounds, zinc compounds, and iron family metal compounds.

In the methods i) and ii), a hydroxy compound or the like, contained in the carbamate-containing liquid, may be used as a solvent.

The reaction time (the residence time in the case of the continuous method) is preferably as short as possible, within a scope which does not interfere with the progress of the desired reaction.

As the thermal decomposition reaction of the carbamate, a method in which a mixture containing a carbamate is supplied to a reactor (may be referred to as thermal decomposition reactor) continuously, subjected to a thermal decomposition reaction, the resultant compound (I) and a partial amount of hydroxy compound are extracted as gas phase components from the thermal decomposition reactor continuously, and the remaining components are extracted as liquid phase components from the thermal decomposition reactor continuously may be adopted, specifically.

The term "gas phase component" means a component present in a gas phase in the thermal decomposition reactor, and the gas phase component contains the compound (I) which is a target product of the reaction, and may contain a partial amount or all of a hydroxyl compound used as a raw material.

The term "liquid phase component" means a component present in a liquid phase in the thermal decomposition reactor, and the liquid phase component preferably contains, as a high-boiling point compound, a compound having at least one group selected from the group consisting of a group of formula (II-1) (hereinafter, may be referred to as "group (II-1)") and a group of formula (II-2) (hereinafter, may be referred to as "group (II-2)").

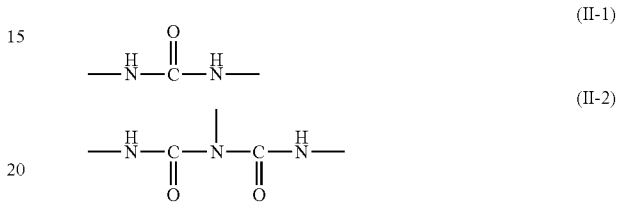

Examples of the compound having the group (II-1) include compounds of the following general formula (XIII) (hereinafter, may be referred to as "compound (XIII)").

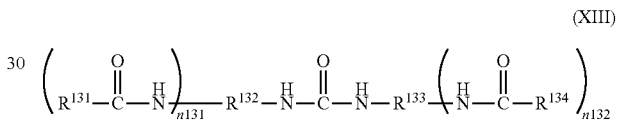

In the general formula (XIII), $R^{131}$ and $R^{134}$ each independently represents a monovalent organic group. $R^{132}$ and $R^{133}$ each independently represents a divalent or trivalent organic group. n131 and n132 each independently represents an integer of 0 to 2.

Examples of $R^{131}$ and $R^{134}$ include the same groups as those mentioned as $R^{122}$ described above. $R^{131}$ and $R^{134}$ may be identical to or different from each other.

Examples of $R^{132}$ and $R^{133}$ include the same divalent or trivalent groups as those mentioned as $R^{11}$ of the compound (I), and specific examples thereof include approximately C1-20 alkylene groups, approximately C5-20 cycloalkylene groups, and approximately C6-20 arylene groups. $R^{132}$ and $R^{133}$ may be identical to or different from each other.

Examples of the compound having the group (II-2) include compounds of the following general formula (XIV) (hereinafter, may be referred to as "compound (XIV)").

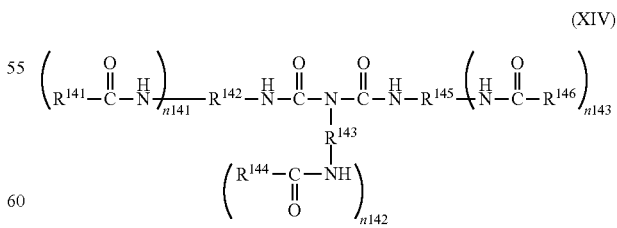

In the general formula (XIV), $R^{141}$, $R^{144}$ and $R^{146}$ each independently represents a monovalent organic group. $R^{142}$, $R^{143}$ and $R^{145}$ each independently represents a divalent or trivalent organic group. n141, n142 and n143 each independently represents an integer of 0 to 2.

Examples of $R^{141}$, $R^{144}$ and $R^{146}$ include the same groups as those mentioned as $R^{122}$ described above. $R^{141}$, $R^{144}$ and $R^{146}$ may be identical to or different from each other.

Examples of $R^{142}$, $R^{143}$ and $R^{145}$ include the same divalent or trivalent groups as those mentioned as $R^{11}$ of the compound (I), and specific examples thereof include approximately C1-20 alkylene groups, approximately C5-20 cycloalkylene groups, and approximately C6-20 arylene groups. $R^{142}$, $R^{143}$ and $R^{145}$ may be identical to or different from each other.

The liquid phase component may further contain, as the high-boiling point compound, an allophanate group-containing compound, and/or, an isocyanurate group-containing compound.

Examples of the allophanate group-containing compound include compounds of the following general formula (XV) (hereinafter, may be referred to as "compound (XV)").

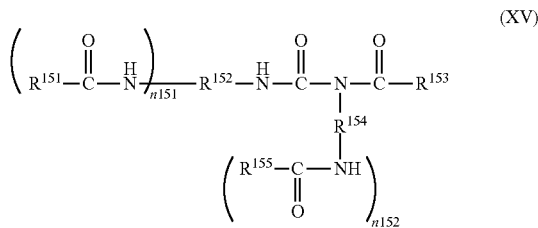

(XV)

In the general formula (XV), $R^{151}$, $R^{153}$ and $R^{155}$ each independently represents a monovalent organic group. $R^{152}$ and $R^{154}$ each independently represents a divalent or trivalent organic group. n151 and n152 each independently represents an integer of 0 to 2.

Examples of $R^{151}$, $R^{153}$ and $R^{155}$ include the same groups as those mentioned as $R^{122}$ described above. $R^{151}$, $R^{153}$ and $R^{155}$ may be identical to or different from each other.

Examples of $R^{152}$ and $R^{154}$ include the same divalent or trivalent groups as those mentioned as $R^1$ of the compound (I), and specific examples thereof include approximately C1-20 alkylene groups, approximately C5-20 cycloalkylene groups, and approximately C6-20 arylene groups. $R^{152}$ and $R^{154}$ may be identical to or different from each other.

Examples of the isocyanurate group-containing compound include compounds of the following general formula (XVI) (hereinafter, may be referred to as "compound (XVI)").

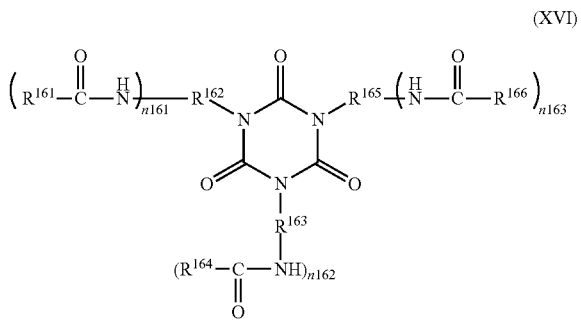

(XVI)

In the general formula (XVI), $R^{161}$, $R^{164}$ and $R^{166}$ each independently represents a monovalent organic group. $R^{162}$, $R^{163}$ and $R^{165}$ each independently represents a divalent or trivalent organic group. n161, n162 and n163 each independently represents an integer of 0 to 2.

Examples of $R^{161}$, $R^{164}$ and $R^{166}$ include the same groups as those mentioned as $R^{122}$ described above. $R^{161}$, $R^{164}$ and $R^{166}$ may be identical to or different from each other.

Examples of $R^{162}$, $R^{163}$ and $R^{165}$ include the same divalent or trivalent groups as those mentioned as $R^{11}$ of the compound (I), and specific examples thereof include approximately C1-20 alkylene groups, approximately C5-20 cycloalkylene groups, and approximately C6-20 arylene groups. $R^{162}$, $R^{163}$ and $R^{165}$ may be identical to or different from each other.

At least a partial amount of a hydroxyl compound used as a raw material may be further contained as the high-boiling point compound.

In the case where an aromatic hydroxy compound is used as a hydroxy compound to produce the compound (I), the liquid phase component may contain a compound having a Fries rearrangement terminal formed by Fries rearrangement of a carbamate group, or may contain a compound in which a partial amount or all of carbamate groups are converted to isocyanate groups in the thermal decomposition reaction. In addition, the liquid phase component may contain the compound (I) which is not extracted from the thermal decomposition reactor, a compound formed by reacting a partial amount or all of isocyanate groups of the compound (I) with a hydroxy compound to form carbamate groups, or the compound (XII) which is not decomposed thermally in the thermal decomposition reactor.

The viscosity of the liquid phase component at 150° C. is preferably 100 MPa·s or less, and more preferably 1 MPa·s to 50 MPa·s, from the viewpoint of the transfer thereof into a reactor in which the liquid phase component according to the present embodiment and at least one kind of active hydrogen-containing compounds are reacted. The viscosity of the liquid phase component may be measured by a conventionally-known measuring instrument, such as a capillary viscometer, a falling ball viscometer, or a rotary viscometer. Specifically, for example, the liquid phase component is heated at a predetermined temperature under a nitrogen atmosphere, and the viscosity thereof may be measured using a B-type viscometer. In the case where the liquid phase component contains a volatile component and the measurement of the viscosity at 150° C. is difficult, the viscosity is measured at a low temperature, and the viscosity at 150° C. may be calculated by plotting the logarithm of the viscosity with the reciprocal of the measured temperature (absolute temperature).

The thermal decomposition reactor is not particularly limited, and a reactor containing a distillation column, a multistage distillation column, a multitubular reactor, a continuous multistage distillation column, a packed column, a thin-film evaporator, a reactor equipped with a support inside thereof, a forced circulation reactor, a falling-film evaporator, or a falling-drop evaporator may be used.

Among these, the thermal decomposition reactor preferably has a structure having a large gas-liquid contact area that allows prompt transfer of the generated low-boiling point component into a gas phase, and a reactor containing a tubular reactor such as a tubular thin-film evaporator or a tubular falling-film evaporator is more preferably used. Thus, it is more preferable that the thermal decomposition reactor be composed of the above-mentioned tubular reactor and a separation tank in which the gas phase component and the liquid phase component are separated, from the viewpoint of the collection of the gas phase component containing the compound (I) from the thermal decomposition reactor.

The flow rate per wetted perimeter of the tubular reactor is preferably 10 kg/hour·m to 1000 kg/hour·m, more preferably 20 kg/hour·m to 500 kg/hour·m, and even more preferably 50 kg/hour·m to 300 kg/hour·m, so as to prevent the formation of deposits on the reactor wall surface while maintaining the wettability of the reactor wall surface.

The term "wetted perimeter" refers to a perimeter of the reactor wall with which a fluid contacts in a vertical direction relative to a flow direction of the fluid (in the case where the reactor is in a cylindrical shape, the term refers to the circumferential length in cross section of the reactor). The "flow rate per wetted perimeter" can be calculated by dividing the flow rate per unit time of the fluid (kg/hour) by the wetted perimeter (m). In the case where the liquid flow rate changes in the reactor, it is preferable that the flow rate per wetted perimeter be within the above-mentioned range when the flow rate becomes minimum.

The linear velocity of the gas phase component in a separation tank is preferably 10 m/second or less, more preferably 7 m/second or less, and even more preferably 3 m/second or less, so as to further suppress deposition of a liquid phase component entrained by a gas phase component containing the compound (I) in a pipe in which the gas phase component is collected, when the gas phase component is separated, the deposition causing clogging of the pipe.

The linear velocity can be determined by dividing the volumetric velocity ($m^3$/second) of the gas phase component passing through the separation tank by the cross-sectional are ($m^2$) of the separation tank.

The liquid phase component extracted continuously from the thermal decomposition reactor by the above-mentioned method may be used as a liquid phase component containing the high-boiling point compound in the collection method according to the present embodiment.

In the case where the liquid phase component is transferred from the thermal decomposition reactor to a reactor in which the reaction in the step 1) of the collection method according to the present embodiment is conducted, the liquid phase component is preferably transferred while maintaining a liquid state. Accordingly, the liquid phase component is preferably supplied to a reactor in which the step 1) is conducted while maintaining the temperature thereof at 150° C. to 350° C., and more preferably 200° C. to 260° C.

From the viewpoint of dissolving the above-mentioned by-products and maintaining the liquid phase state, the liquid phase component preferably contains a hydroxy compound in addition to a compound having at least one group selected from the group consisting of the group (TI-1) and the group (II-2), and the amount of the hydroxy compound, relative to the total mass of the liquid phase component, is preferably 20% by mass to 70% by mass, and more preferably 30% by mass to 50% by mass. The hydroxy compound may be supplied from at least one pipe formed in a pipe in which the liquid phase component is collected from the thermal decomposition reactor or a separation tank of the thermal decomposition reactor, so as to allow the above-mentioned amount of the hydroxy compound to be contained.

<Each Step of the Collection Method>

Next, each step of the collection method according to the present embodiment will be explained in detail.

[Step (1)]

The step (1) is a step in which a liquid phase component containing a high-boiling point compound that is formed as a by-product in the method for producing the compound (I) and at least one kind of active hydrogen-containing compounds are reacted in a reactor.

The active hydrogen-containing compound is preferably at least one selected from the group consisting of water, urea, alcohols, aromatic hydroxy compounds and organic primary amines, and more preferably at least one selected from the group consisting of water, urea, alcohols and aromatic hydroxy compounds. One kind of these may be used alone or at least two kinds thereof may be used in combination. Among these, water, the combination of water and an aromatic hydroxy compound, the combination of water and an alcohol, the combination of urea and an aromatic hydroxy compound, or the combination of urea and an alcohol is preferable.

It is preferable to supply the compound (III) at the step (1) in addition to water, the combination of water and an aromatic hydroxy compound, the combination of water and an alcohol, the combination of urea and an aromatic hydroxy compound, or the combination of urea and an alcohol, so as to allow the decomposition reaction in the reactor to proceed promptly or to increase the yield.

The stoichiometric ratio of the active hydrogen-containing compound, relative to the total mol of biuret groups, allophanate groups, isocyanurate groups, carbamate groups, urea groups and Fries rearrangement terminals, contained in the liquid phase component, may be 1 to 500.

The amount of biuret groups, allophanate groups, isocyanurate groups, carbamate groups, urea groups and Fries rearrangement terminals, may be determined by conducting an infrared spectroscopic measurement (IR measurement) or a nuclear magnetic resonance spectroscopic measurement (NMR measurement) using the liquid phase component as a sample.

The total amount of the above-mentioned groups may be estimated easily by determining the quantity of —$CH_2$— groups (methylene groups) adjacent to N atoms in the groups by conducting a NMR measurement.

In the case where the active hydrogen-containing compound contains at least two compounds and one of the compounds is water, it is preferable that the stoichiometric ratio of water, relative to the total mol of biuret groups, allophanate groups, isocyanurate groups, carbamate groups and urea groups, contained in the liquid phase component, be 1 to 200, and the stoichiometric ratio (molar ratio) of an alcohol, an aromatic hydroxy compound and an organic primary amine, be in an appropriate amount, that is, the stoichiometric ratio thereof, relative to water, be 0.01 to 200.

The liquid phase component and the active hydrogen-containing compound may be mixed in advance, followed by supplying the mixture to a reactor in which the decomposition reaction is conducted, or may be supplied to the reactor separately. In addition, the liquid phase component and the active hydrogen-containing compound may be heated before supplying them to a reactor in which the decomposition reaction is conducted within a range in which an essence of the present embodiment is not impaired.

Although the temperature at which the decomposition reaction is conducted may be determined depending on compounds to be used, the temperature is preferably 100° C.

to 350° C., more preferably 150° C. to 330° C., and even more preferably 200° C. to 300° C.

Although the pressure depends on the compound to be used, the pressure is 0.01 kPa to 15 MPa (absolute pressure), and may be reduced pressure, ordinary pressure or increased pressure.

In view of the above-mentioned preferable temperature range, the active hydrogen-containing compound to be used, and the resultant compound generated by the decomposition reaction, the reaction is preferably conducted at an increased pressure, more preferably at a pressure within a range of 0.101 MPa to 15 MPa (absolute pressure), even more preferably at a pressure within a range of 0.5 MPa to 13 MPa (absolute pressure), and even more preferably at a pressure within a range of 2 MPa to 8 MPa (absolute pressure).

The reaction time (the residence time in the case of a continuous reaction) is 0.01 hours to 100 hours, and the reaction liquid may be sampled appropriately to measure the production amount of the target compound (III) and the time required to obtain the predetermined production amount thereof may be made as the reaction time.

[Step (2)]

The step (2) is a step for returning a condensed liquid obtained by cooling a gas phase component formed as a by-product in the step (1) to the reactor.

The gas phase component formed as a by-product in the decomposition reaction at the step (1) refers to a component having a boiling point lower than that of the liquid phase component formed as a by-product in the method for producing the compound (I) or an active hydrogen-containing compound which are raw materials at the step (1), and examples thereof include components having a boiling point of 30° C. or less. The gas phase component formed as a by-product depends on an active hydrogen-containing compound to be used, and, specifically, the gas phase component contains carbon dioxide when the active hydrogen-containing compound contains water, or the gas phase component contains carbon dioxide and ammonia when the active hydrogen compound contains urea.

The decomposition reaction at the step (1) is conducted while extracting at least a partial amount of the gas phase component to the outside of the reaction system, because there is a case where the pressure in the reaction system increases or the decomposition reaction becomes slow depending on the gas phase component. It is preferable that the gas phase component be extracted continuously so as to allow the decomposition reaction in which the pressure is maintained within a certain range to proceed promptly. It is preferable that the gas phase component be extracted from the reactor, without extracting the active hydrogen-containing compound together with the gas phase component to the outside of the reactor, or while controlling the pressure inside the reactor by disposing a pressure-holding valve configured to control the pressure.

The gas phase component extracted from the reactor is introduced into a condenser connected with the reactor to conduct cooling. The condensed liquid obtained by cooling in the condenser is returned inside the reactor. The condensed liquid is preferably water. The cooling step in the condenser is preferably conducted approximately at 0° C. to 80° C.

[Step (3)]

Step (3) is a step for discharging a gas phase component that is not condensed in the step (2) to the outside of the reactor. The gas phase component that is not condensed depends on an active hydrogen-containing compound to be used. Specifically, the gas phase component that is not condensed contains carbon dioxide, when at least one of the active hydrogen-containing compounds is water, or the gas phase component that is not condensed contains carbon dioxide and ammonia, when at least one of the active hydrogen compounds is urea.

[Step (4)]

Step (4) is a step for discharging the liquid phase component formed in the decomposition reaction in the step (1) to the outside of the reactor. The liquid phase component (reaction liquid) to be discharged contains the compound (III).

(Reactor)

A reactor used at the step (1) is not particularly limited, and conventionally-known reactors may be used. The conventionally-known reactors, such as a stirring tank, a storage tank, a column-type reactor, a distillation column, a packed column, a thin-film evaporator, a paddle-type drier equipped with a forced transporting device, and an extruder equipped with a degassing device, a thin-film evaporator equipped with a forced transporting device, or a tube-type reactor, may be used in combination depending on the reaction method or conditions.

The reaction may be conducted in batches or in a continuous flow type, and the reactor may be selected depending on the reaction form.

The material of the reactor is not particularly limited, and a conventionally-known material may be used. Examples thereof include glass, stainless steel, carbon steel, HASTELLOY, and substrates subjected to glass lining or TEFLON (trademark) coating. SUS 304, SUS 316, or SUS 316L is preferably used because of the low prices thereof. The reactor may be equipped with, as needed, an instrumentation device such as a flow meter or a thermometer, or a conventionally-known process device such as a pressure-holding mechanism, a reboiler, a pump, a condenser, or a flash tank. In addition, the reactor may be heated by a conventionally-known method using a steam, a heater, or the like, or may be cooled by a conventionally-known method such as natural cooling, water-cooling or brining. The reactor may be further equipped with additional devices, as needed.

Among these reactors, at least one selected from the group consisting of a tank-type reactor, an extruder, and a thin-film evaporator is preferably used, and a tank-type reactor is more preferably used.

(1) Tank-Type Reactor

FIG. 1 is a schematic configuration drawing illustrating one example of a collection device to be used in the collection method according to the present embodiment, and a tank-type reactor (1) is used as a reactor.

The tank-type reactor is preferably a pressure-resistant reactor equipped with a stirrer, and is preferably connected with a storage tank and a condenser via pipes.

The collection device shown in FIG. 1 contains: a stirring tank (pressure-resistant reactor) B101 in which a liquid phase component formed as a by-product in the step for producing the compound (I) and at least one active hydrogen-containing compound are reacted; a condenser B102 in which a gas phase component formed as a by-product in the decomposition reaction in the stirring tank B101 is cooled; a storage tank B103 in which the liquid phase component formed by the decomposition reaction in the stirring tank B101 is stored; a pressure-holding valve B104 configured to maintain the pressure to discharge a gas phase component that is not condensed in the condenser B102; a line B1 configured to supply the liquid phase component formed as a by-product in the step for producing the compound (I) to the stirring tank B101; a line B2 configured to transfer the gas phase component generated in the stirring tank B101 o the condenser B102; a line B3 configured to return the condensed liquid obtained by cooling in the condenser B102 to the stirring tank B101; a line B4 configured to discharge the gas phase component that is not condensed in the condenser B102; and a line B5 configured to transfer the liquid phase component generated in the stirring tank B101 to the storage tank B103. The collection device shown in FIG. 1 may be further equipped with, as needed, an instrumentation device, such as a liquid feeding pump, a flow meter, or a thermometer, or a conventionally-known process device such as a heat exchanger. In addition, the collection device shown in FIG. 1 may be connected with plural tank-type reactors, as needed.

Figure 2:
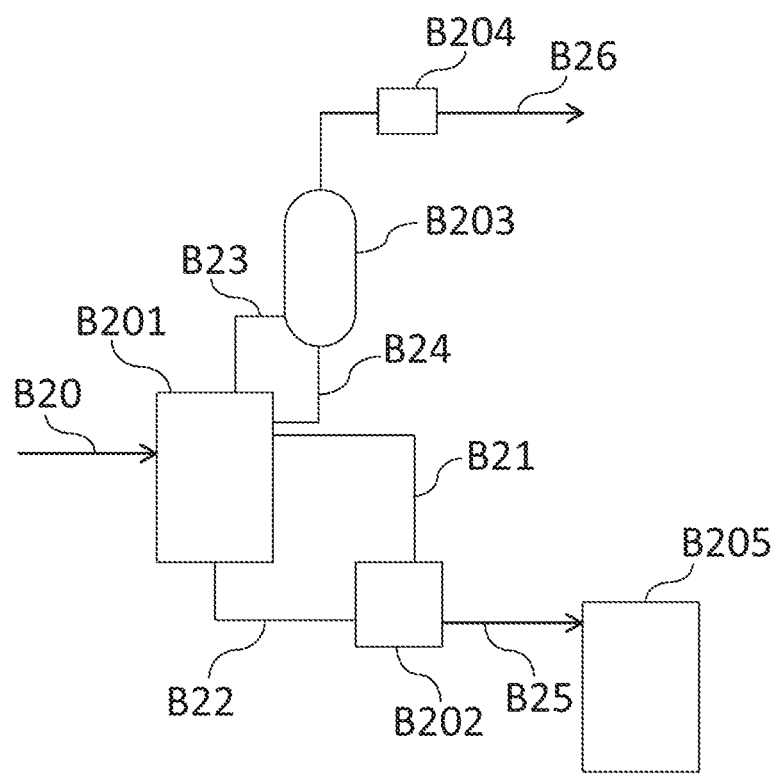
FIG. 2 is a schematic configuration drawing illustrating another example of a collection device to be used in the collection method according to the present invention.

FIG. 2 is a schematic configuration drawing illustrating another example of the collection device in which a tank-type reactor (1) is used as a reactor in the collection method according to the present embodiment.

The collection device shown in FIG. 2 contains: a reaction tank (pressure-resistant reactor) B201 in which a liquid phase component formed as a by-product in the step for producing the compound (I) and at least one active hydrogen-containing compound are mixed and reacted; a condenser B203 in which the gas phase component formed as a by-product by the decomposition reaction in the reaction tank B201 is cooled; a storage tank B205 in which the liquid phase component generated in the decomposition reaction in the reaction tank B201 is stored; a pressure-holding valve B204 configured to maintain the pressure to discharge a gas phase components that are not condensed in the condenser B203; a pump B202 configured to extract the liquid phase component from the reaction tank B201 to return the liquid phase component to the reaction tank B201 again to allow the liquid phase component to be stirred and circulated; a line B20 configured to supply the liquid phase component formed as a by-product in the step for producing the compound (I) to the reaction tank B201; a line B24 configured to transfer the gas phase component formed as a by-product in the reaction tank B201 to the condenser B203; a line B23 configured to return the condensed liquid obtained by cooling in the condenser B203 to the reaction tank B201; a line B26 configured to discharge a gas phase component that is not condensed in the condenser B203; a line B21 configured to pass the liquid phase component extracted from the reaction tank B201 to return to the reaction tank B201, or to transfer the storage tank B205; and a line B25 configured to transfer a liquid phase component extracted from the reaction tank B201 to the storage tank B205.

The amount of the liquid fed through the pump B202 may be appropriately determined depending on the amount of the reaction liquid in the reaction tank B201 or materials to be used.

Figure 3:
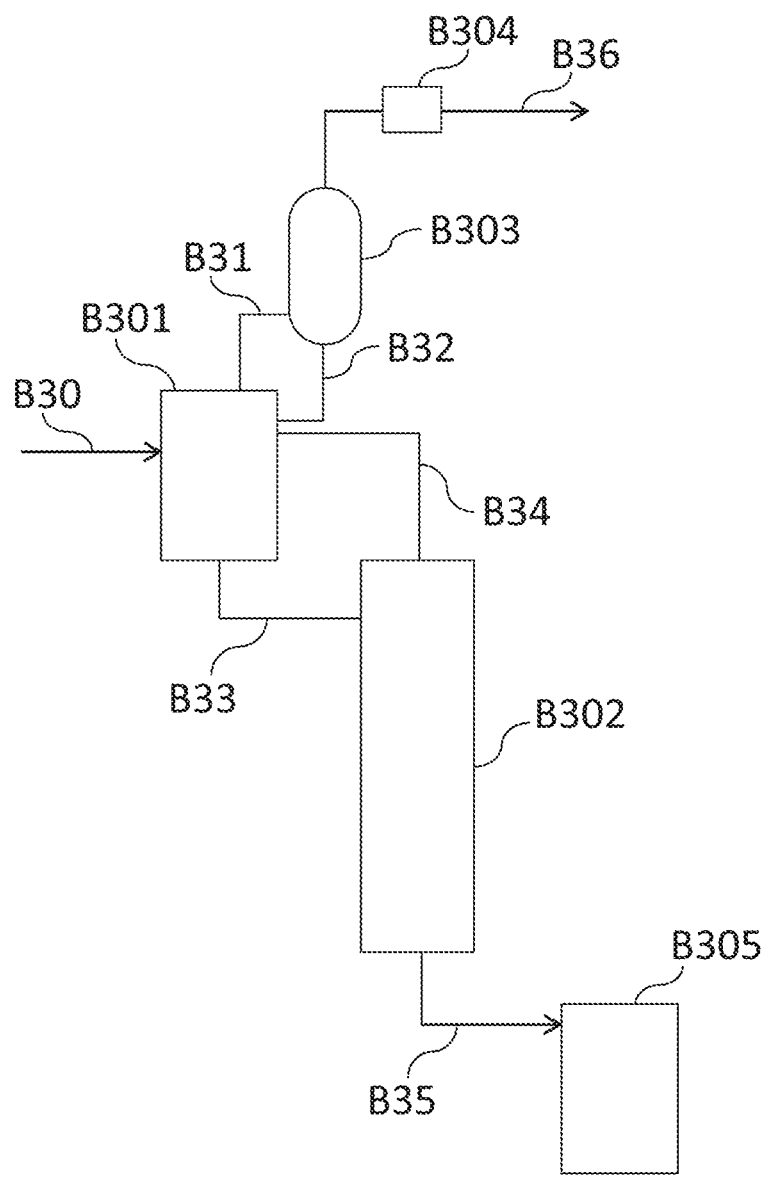
FIG. 3 is a schematic configuration drawing illustrating another example of a collection device to be used in the collection method according to the present invention.

FIG. 3 is a schematic configuration drawing illustrating another example of the collection device in which a tank-type reactor (1) is used as a reactor in the collection method according to the present embodiment.

The collection device shown in FIG. 3 contains: a stirring tank (pressure-resistant reactor) B301 in which a liquid phase component formed as a by-product in the step for producing the compound (I) and at least one active hydrogen-containing compound are mixed and reacted; a reaction tank (pressure-resistant reactor) B302 in which liquid phase components formed by the decomposition reaction in the stirring tank B301 are reacted; a condenser B303 in which a gas phase component formed as a by-product by the decomposition reaction in the stirring tank B301 is cooled; a storage tank B305 in which the liquid phase component generated in the decomposition reaction in the reaction tank B302 is stored; a pressure-holding valve B304 configured to maintain the pressure to discharge a gas phase components that is not condensed in the condenser B303; a line B30 configured to supply the liquid phase component formed as a by-product in the step for producing the compound (I) to the stirring tank B301; a line B32 configured to transfer the gas phase component generated in the stirring tank B301 to the condenser B303; a line B31 configured to return the condensed liquid obtained by cooling in the condenser B303 to the stirring tank B301; a line B36 configured to discharge the gas phase component that is not condensed in the condenser B303; a line B33 configured to transfer the liquid phase component generated in the decomposition reaction in the stirring tank B301 to the reaction tank B302; a line B34 configured to return the gas phase component formed as a by-product by the decomposition reaction in the reaction tank B302 to the stirring tank B301; and a line B35 configured to transfer the liquid phase component generated in the decomposition reaction in the reaction tank B302 to the storage tank B305.

(2) Extruder

Although a reciprocating type extruder configured to realize extrusion using a plunger or a continuous type extruder configured to realize extrusion by rotating a screw may be used as an extruder, the continuous type extruder is preferably used to conduct the decomposition reaction under stable conditions. Although the screw may be monoaxial or multiaxial (such as biaxial), the screw is preferably multi-axial, and more preferably biaxial, because there is a case in which the viscosity of remaining components is increased or the remaining components are solidified when the viscosity of a reaction liquid is high or the decomposition reaction is conducted while extracting a partial amount or all of decomposed products as gas phase components using an extruder provided with a degassing part.

Figure 4:
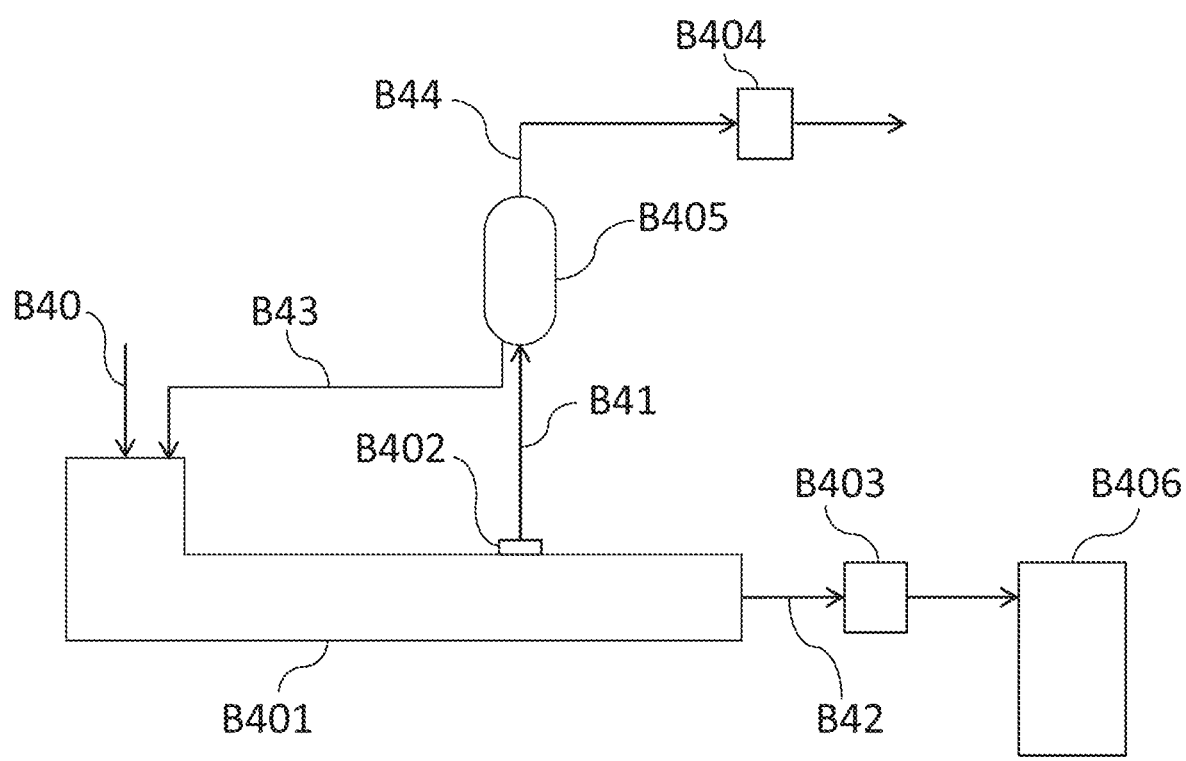
FIG. 4 is a schematic configuration drawing illustrating another example of a collection device to be used in the collection method according to the present invention.

FIG. 4 is a schematic configuration drawing illustrating one example of a collection device to be used in the collection method according to the present embodiment, in which an extruder (2) is used as a reactor.

The collection device shown in FIG. 4 contains: an extruder B401 in which a liquid phase component formed as a by-product in the step for producing the compound (I) and an active hydrogen-containing compound are reacted; a condenser B405 in which a gas phase component formed as a by-product by the decomposition reaction in the extruder B401 is cooled; a storage tank B406 in which the liquid phase component generated in the decomposition reaction in the extruder B401 is stored; a pressure-holding valve B403 configured to maintain the pressure to discharge the liquid phase component generated in the decomposition reaction in the extruder B401; a pressure-holding valve B404 configured to maintain the pressure to discharge the gas phase components that are not condensed in the condenser B405; a line B40 configured to supply the liquid phase component formed as a by-product in the step for producing the compound (I) to the extruder B401; a vent port B402 configured to extract the gas phase component formed as a by-product by the decomposition reaction in the extruder B401; a line B41 configured to transfer the gas phase component extracted from the vent port B402 to the condenser B405; a line B43 configured to return the condensed liquid obtained by cooling in the condenser B405 to the extruder B401; a line B44 configured to discharge the gas phase components that are not condensed in the condenser B405; and a line B42 configured to transfer the liquid phase component obtained in the extruder B401 to the storage tank B406.

Although one vent port B402 is indicated in FIG. 4, plural vent ports may be formed.

Although only one each of the lines B40, B41, B42, B43 and B44 is indicated, a plurality of each of the lines B40, B41, B42, B43 and B44 may be formed.

Figure 5:
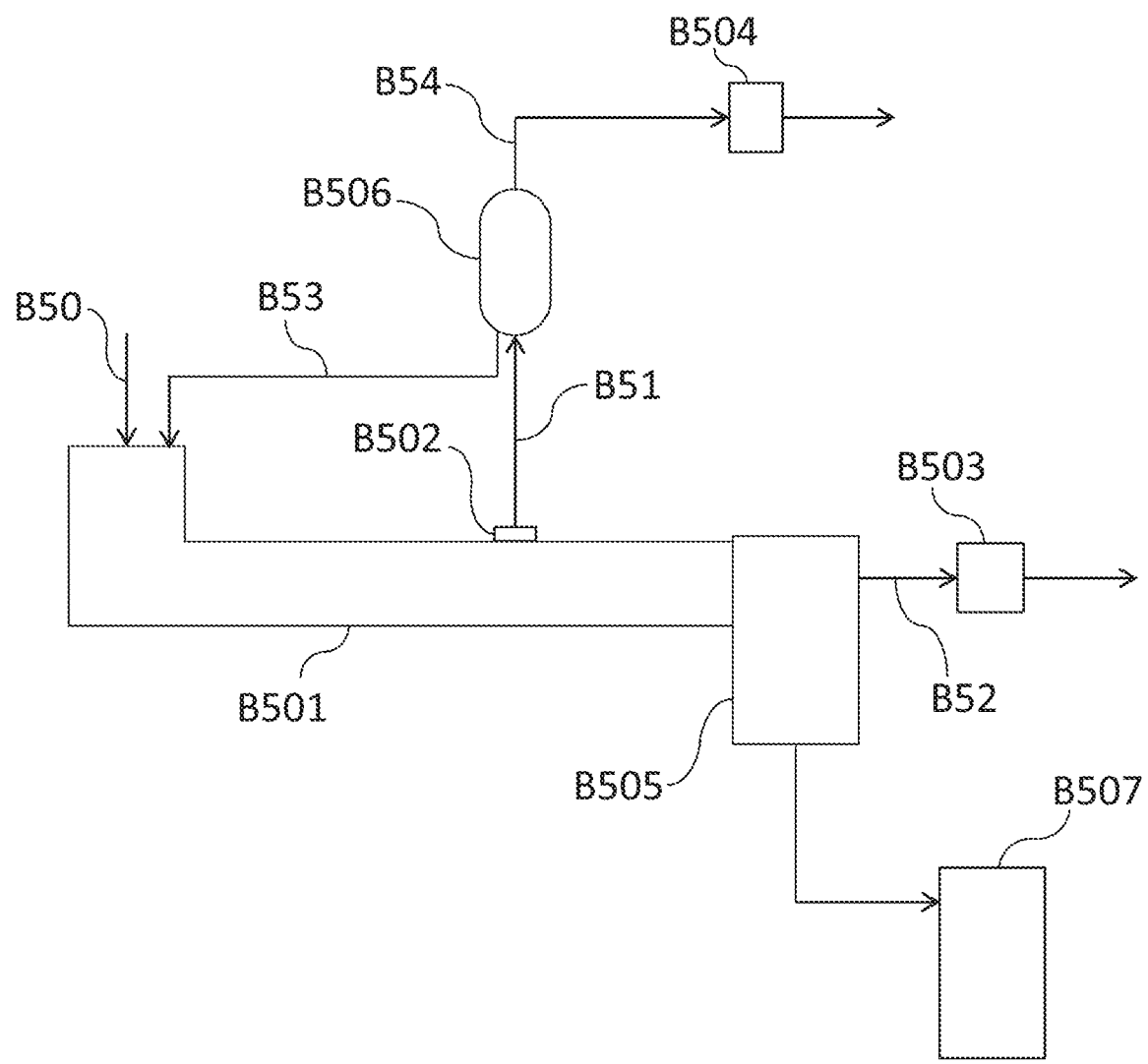
FIG. 5 is a schematic configuration drawing illustrating another example of a collection device to be used in the collection method according to the present invention.

FIG. 5 is a schematic configuration drawing illustrating another example of the collection device used in the collection method according to the present embodiment, in which an extruder (2) is used as a reactor.

The collection device shown in FIG. 5 contains: an extruder B501 in which a liquid phase component formed as a by-product in the step for producing the compound (I) and an active hydrogen-containing compound are reacted; a vent port B502 in which a gas phase component formed as a by-product by the decomposition reaction in the extruder B501 is extracted; a condenser B506 in which the gas phase component extracted from the vent port B502 is cooled; a pressure-holding valve B504 configured to maintain the pressure to discharge the gas phase components that are not condensed in the condenser B506; a storage tank B507 in which the liquid phase component generated in the decomposition reaction in the extruder B501 is stored; a receiver B505 in which decomposition products discharged from the extruder B501 are collected; a pressure-holding valve B503 configured to maintain the pressure to discharge gas phase components contained in the decomposition products collected in the receiver B505 without being discharged from the vent port B502; a storage tank B507 in which liquid phase components contained in the decomposition products collected in the receiver B505 are stored; a line B50 configured to supply the liquid phase component formed as a by-product in the step for producing the compound (I) to the extruder B501; a line B51 configured to transfer the gas phase component extracted from the vent port B502 to the condenser B506; a line B53 configured to return the condensed liquid obtained by cooling in the condenser B506 to the extruder B501; a line B54 configured to discharge the gas phase components that are not condensed in the condenser B506; and a line B52 configured to discharge the gas phase components contained in the decomposition products collected in the receiver B505. The collection device shown in FIG. 5 is particularly preferably used in the case where the viscosity of remaining components is increased or remaining components are solidified. A collection part configured to collect, from the receiver 505, the decomposition products collected in the receiver 505, so as to conduct the decomposition reaction continuously.

Thin-Film Evaporator (3)

Examples of a device having a part configured to form a thin-film of a reaction liquid on the heated surface include a thin-film evaporator, a molecular distillation device, and a centrifugal thin-film evaporator.

Figure 6:
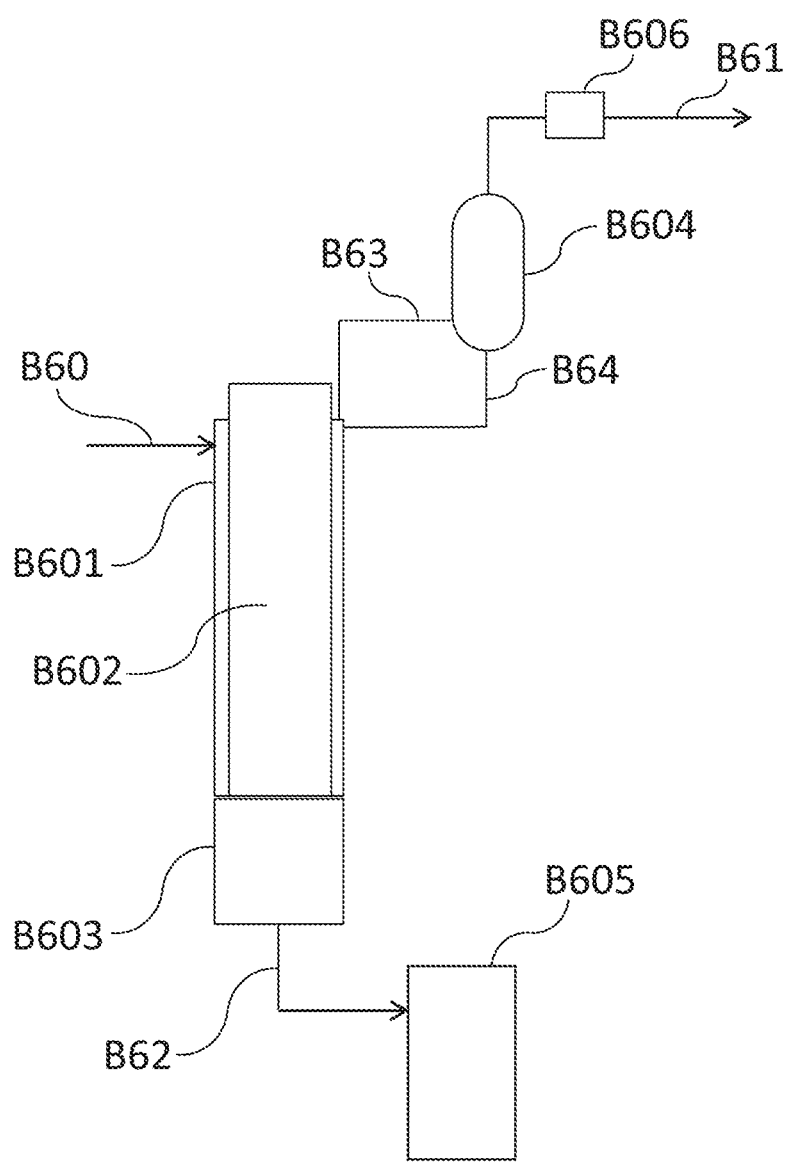
FIG. 6 is a schematic configuration drawing illustrating another example of a collection device to be used in the collection method according to the present invention.

FIG. 6 is a schematic configuration drawing illustrating one example of a collection device used in the collection method according to the present embodiment, in which a thin-film evaporator (3) is used as a reactor.

The collection device shown in FIG. 6 contains: a thin-film evaporator B602 having a heated evaporation surface B601 on which a liquid phase component formed as a by-product in the step for producing the compound (1) and an active hydrogen-containing compound are reacted; a condenser B604 in which a gas phase component formed as a by-product by the decomposition reaction on the heated evaporation surface B601 is cooled; a collection part B603 in which the liquid phase component generated in the decomposition reaction on the heated evaporation surface B601 is collected; a storage tank B605 in which the liquid phase component collected in the collection part B603 is stored; a pressure-holding valve B606 configured to maintain the pressure to discharge the gas phase components that are not condensed in the condenser B604; a line B60 configured to supply the liquid phase component formed as a by-product in the step for producing the compound (I) to the thin-film evaporator B602; a line B64 configured to transfer the gas phase component generated as a by-product on the heated evaporation surface B601 to the condenser B604; a line B63 configured to return the condensed liquid obtained by cooling in the condenser B604 to the thin-film evaporator B602; a line B61 configured to discharge the gas phase components that are not condensed in the condenser B604; and a line B62 configured to transfer the liquid phase component collected in the collection part B603 to the storage tank B605.

The liquid phase component and the active hydrogen-containing compound supplied from the line B60 to the thin-film evaporator B602 are developed on the heated evaporation surface B601 of the thin-film evaporator.

The heated evaporation surface B601 is appropriately heated with an electric heater, an oil jacket, or the like.

The thin-film evaporator B602 may be of a conventionally-known type without any particular limitation, and may be of a type in which centrifugal dispersion is conducted, or a thin film is formed by pressing a liquid against the heated evaporation surface B601 by a stirring blade. The liquid phase component and the active hydrogen-containing compound developed on the heated evaporation surface B601 cause the decomposition reaction.

The gas phase component generated as a by-product by the decomposition reaction on the heated evaporation surface B601 is extracted from the line B64 to be introduced into the condenser B604. The condensed liquid obtained by cooling in the condenser B604 is supplied through the line B63 to the thin-film evaporator B602. The gas phase component which is not condensed in the condenser B604 is discharged from the pressure-holding valve B606 through the line B61.

The liquid phase component generated by the decomposition reaction on the heated evaporation surface B601 slips on the heated evaporation surface B601 and then is collected in the collection part B603. The component collected in the collection part B603 is collected through the line B62 in the storage tank B605. A discharging part, such as a stirring blade or a screw blade, is preferably formed on the collection part B603. The stirring blade or the screw blade formed on the collection part B603 may be connected with the same support drive as that of the thin-film evaporator B602, or the different support drive from that of the thin-film evaporator B602.

[Step (5)]

The collection method according to the present embodiment preferably further contains a step (5) in which the compound (III) is separated from the liquid phase component (reaction liquid) discharged in the step (4).

As the method for separating the compound (III) from the reaction liquid obtained in the step (4), a conventionally-known method may be adopted, and examples thereof include: distillation separation; liquid-liquid separation; solid-liquid separation; and membrane separation.

In the step (5), the compound (III) may be separated continuously from the liquid phase component (reaction liquid) discharged continuously in the step (4).

[Step (6)]

The collection method according to the present embodiment preferably further contains a step (6) in which the compound (III) separated in the step (5) is purified. As the method for purifying the compound (III), a conventionally-known method may be adopted, and examples thereof include: distillation separation, liquid-liquid separation, solid-liquid separation, and membrane separation. In the step (6), the compound (III) separated continuously in the step (5) may be purified continuously.

The compound (III) collected in the step (6) is preferably recycled to the production step of the compound (I). At the time, the compound (III) is preferably collected by distillation in the step (6) such that, relative to the total mass of the compound (III), the amount of metallic components becomes 1000 ppm by mass or less and the amount of halogen atoms becomes 1000 ppm by mass or less, because the method for producing the compound (I) or the quality of the compound (I) produced by the method is often affected thereby.

[Step (7)]

In the case where the step (1) is conducted using a compound having a carbamate group (—NH—C(=O)—OR), such as compounds of the above-shown general formulae (XIII) to (XVI), for example, a hydroxyl compound represented by ROH is generated by the reaction with an active hydrogen-containing compound.

In the case where a compound of the general formula (V) (hereinafter, may be referred to as "compound (V)") shown below is used as a hydroxy compound in the method for producing the compound (I), a carbamate group is a group of the following general formula (IV) (hereinafter, may be referred to as "group (IV)"), and a compound (V), that is, an aromatic hydroxy compound, is generated by conducting the step (1) using a compound having the group (IV).

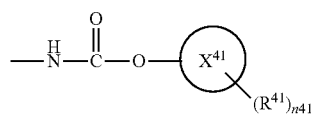

(IV)

In the general formula (IV), $X^{41}$ is a C6-12 aromatic hydrocarbon ring or a heteroaromatic ring. $R^4$ represents a substituent group of $X^{41}$, and is a C1-20 alkyl group which may be substituted with a phenyl group and/or a hydroxy phenyl group, an amino group, or a hydroxy group. n41 represents the number of the substituent group $R^{41}$, and is an integer of 0 to 4, and preferably an integer of 0 to 3. In the case where n41 is 2 or more, $R^4$ is identical to or different from each other.

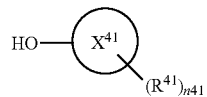

(V)

In the general formula (V), $X^{41}$, $R^{41}$ and n41 are the same groups as those described in the general formula (IV).

$X^{41}$ is a C6-12 aromatic hydrocarbon ring or heteroaromatic ring.

Although examples of the aromatic hydrocarbon ring include a benzene ring and a naphthalene ring, the aromatic hydrocarbon ring is preferably a benzene ring.

Examples of the heteroaromatic ring include a pyridine ring.

Preferable examples of the compound (V) include phenol, tetramethylbutylphenol, di(dimethylbenzyl)phenol, heptylphenol, nonylphenol, tribenzylphenol, di-tert-aminophenol, phenylphenol, diisopropylphenol, tribenzylphenol, hydroquinone, and bisphenol A.

In this case, the compound (V) is preferably collected by further conducting the following step (7) after the compound (V) is separated in the step (5) together with the compound (III) from the reaction liquid obtained in the step (4) and then the step (6) is conducted.

Step (7): a step in which the compound (V) is purified.

As the method for purifying the compound (V) separated in the step (5), a conventionally-known method may be adopted, and examples thereof include distillation separation, liquid-liquid separation, solid-liquid separation, and membrane separation.

The step (7) may be conducted at the same time as the step (5) or the step (6), or the steps (1) to (5) may be conducted continuously.

The compound (V) collected in the step (7) is preferably recycled to the method for producing the compound (I). At the time, the compound (V) is preferably collected by distillation in the step (7) such that, relative to the total mass of the compound (V), the amount of metallic components becomes 1000 ppm by mass or less and the amount of halogen atoms becomes 1000 ppm by mass or less, because the method for producing the compound (I) or the quality of the compound (I) produced by the method is often affected thereby.

«Collection Method»

An organic amine collection method according to the second embodiment of the present invention is a method in which the compound (III) is collected from a liquid phase component containing a high-boiling point compound that is formed as a by-product in the method for producing the compound (I), the method containing the following steps (A), (B) and (4):

step (A): a step for mixing the liquid phase component, water, and a compound of general formula (III);

step (B): a step for reacting the liquid phase component with water inside the reactor; and step (4): a step for discharging, as a liquid phase component inside the reactor, the reaction liquid containing the compound (III) to the outside of the reactor.

In the collection method according to the present embodiment, the same configuration as that of the collection method according to the first embodiment may not be explained.

[Step (A)]

The step (A) is a step for mixing the liquid phase component containing a high-boiling point compound that is formed as a by-product in the method for producing the compound (I), water, and the compound (III).

The liquid phase component containing a high-boiling point compound that is formed as a by-product in the method for producing the compound (I) and the compound (III) are the same as described in the first embodiment.

The stoichiometric ratio of water used in the step (A), relative to the total mol of biuret groups, allophanate groups, isocyanurate groups, carbamate groups and urea groups, contained in the liquid phase component, is preferably 1 to 200.

The stoichiometric ratio (molar ratio) of the compound (III) used in the step (A), relative to water, is preferably 0.01 to 200.

The amount of the biuret groups, allophanate groups, isocyanurate groups, carbamate groups, urea groups and Fries rearrangement terminals are the same as described in the first embodiment.

The liquid phase component, water and the compound (III) may be mixed in advance, and then supplied to a reactor in which the step (B) is conducted, or may be supplied thereto separately to be mixed in the reactor. The liquid phase component, water and the compound (III) may be heated before supplying them to the reactor in which the step (B) is conducted unless an essence of the present embodiment is interfered.

[Step (B)]

Step (B) is a step for reacting the liquid phase component with water inside the reactor.

The temperature in the reactor at the step (B) is preferably 100° C. to 350° C., more preferably 150° C. to 330° C., and even more preferably 200° C. to 300° C.

The pressure in the reactor is preferably 0.01 kPa to 15 MPa (absolute pressure), and may be reduced pressure, normal pressure, or increased pressure.

In view of the above-mentioned preferable temperature range or compounds generated by the decomposition reaction, the pressure is preferably increased pressure, more preferably 0.101 MPa to 15 MPa (absolute pressure), even more preferably 0.5 MPa to 13 MPa (absolute pressure), and particularly preferably 2 MPa to 8 MPa (absolute pressure).

The reaction time (the residence time in the case of a continuous reaction) is preferably 0.01 hours to 100 hours, and a reaction liquid may be sampled appropriately to measure the production amount of the target compound (III) to determine the time required to obtain the predetermined production amount as the reaction time.

[Step (4)]

Step (4) is a step for discharging, as a liquid phase component inside the reactor, the reaction liquid containing the compound (III) to the outside of the reactor, and may be conducted in the same way as that of the first embodiment.

(Collection Device)

Although the same collection devices as the first embodiment may be used as collection devices in the collection method according to the present embodiment, the following collection devices may also be used.

Figure 8A:
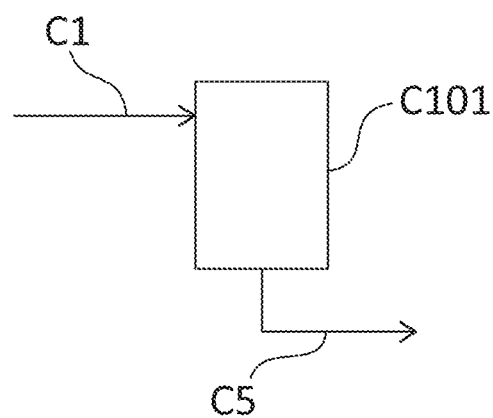
FIG. 8A is a schematic configuration drawing illustrating another example of a collection device to be used in the collection method according to the present invention.

FIG. 8A is a schematic configuration drawing illustrating one example of a collection device used in the collection method according to the present embodiment, in which a tank-type reactor (1) is used as a reactor.

The collection device shown in FIG. 8A contains: a stirring tank (pressure-resistant reactor) C101 in which a liquid phase component formed as a by-product in the step for producing the compound (I) and water are reacted; a line C1 configured to supply the liquid phase component formed as a by-product in the step for producing the compound (I), water and a compound (III) to the stirring tank C101; and a line C5 configured to discharge a liquid phase component obtained in the stirring tank C101.

The collection device shown in FIG. 8A may further contain: an instrumentation device such as a liquid feeding pump, a flow meter, or a thermometer; or a conventionally-known process device such as a heat exchanger, as needed.

Figure 8B:
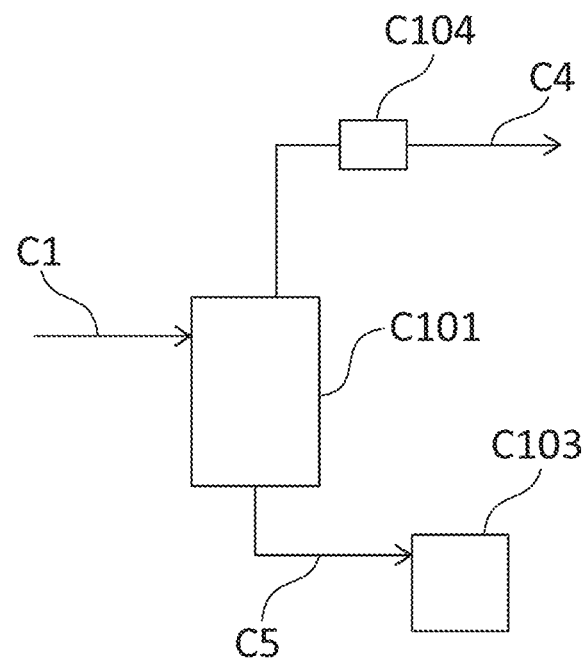
FIG. 8B is a schematic configuration drawing illustrating another example of a collection device to be used in the collection method according to the present invention.

FIG. 8B is a schematic configuration drawing illustrating another example of the collection device used in the collection method according to the present embodiment, in which a tank-type reactor (1) is used as a reactor.

The collection device shown in FIG. 8B contains: a stirring tank (pressure-resistant reactor) C101 in which a liquid phase component formed as a by-product in the step for producing the compound (1) and water are reacted; a storage tank C103 in which a liquid phase component generated in the decomposition reaction in the stirring tank C101 is stored; a pressure-holding valve C104 configured to maintain the pressure to discharge a gas phase component generated as a by-product in the stirring tank C101; a line C1 configured to supply the liquid phase component formed as a by-product in the step for producing the compound (I), water and a compound (III) to the stirring tank C101; a line C4 configured to discharge a gas phase component generated in the stirring tank C101; and a line C5 configured to transfer the liquid phase component obtained in the stirring tank C101 to the storage tank C103.

The collection device shown in FIG. 8B may further contain: an instrumentation device such as a liquid feeding pump, a flow meter, or a thermometer; or a conventionally-known process device such as a heat exchanger, as needed. In addition, the collection device shown in FIG. 8B may be equipped with plural tank-type reactors connected with each other, as needed.

Figure 9:
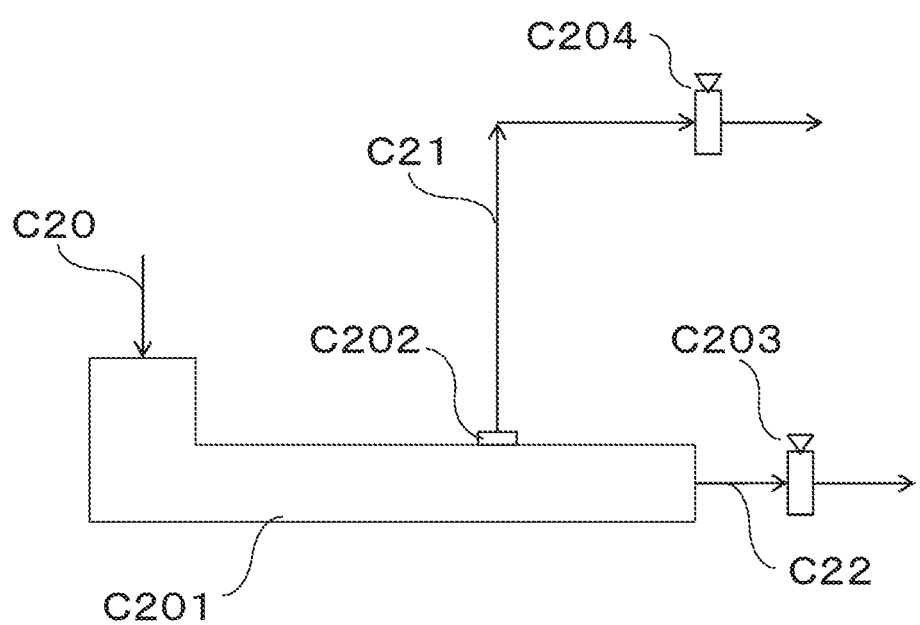
FIG. 9 is a schematic configuration drawing illustrating another example of a collection device to be used in the collection method according to the present invention.

FIG. 9 is a schematic configuration drawing illustrating one example of the collection device used in the collection method according to the present embodiment, in which an extruder (2) is used as a reactor.

The collection device shown in FIG. 9 contains: an extruder C201 in which a liquid phase component formed as a by-product in the step for producing the compound (I) and water are reacted; a vent port C202 configured to extract a gas phase component formed as a by-product by the decomposition reaction in the extruder C201; a pressure-holding valve C203 configured to maintain the pressure to discharge the liquid phase component generated in the decomposition reaction in extruder C201; a pressure-holding valve C204 configured to maintain the pressure to discharge the gas phase component generated as a by-product in the extruder C201; a line C20 configured to supply the liquid phase component formed as a by-product in the step for producing the compound (I), water and a compound (III) to the extruder C201; a line C21 configured to discharge the gas phase component extracted from the vent port C202; and a line C22 configured to discharge the liquid phase component obtained in the extruder C201.

Although one vent port C202 is indicated in FIG. 9, plural vent ports C202 may be formed.

Although one each of the lines C20, C21 and C22 is indicated, a plurality of each of the lines C20, C21 and C22 may be formed.

Figure 10:
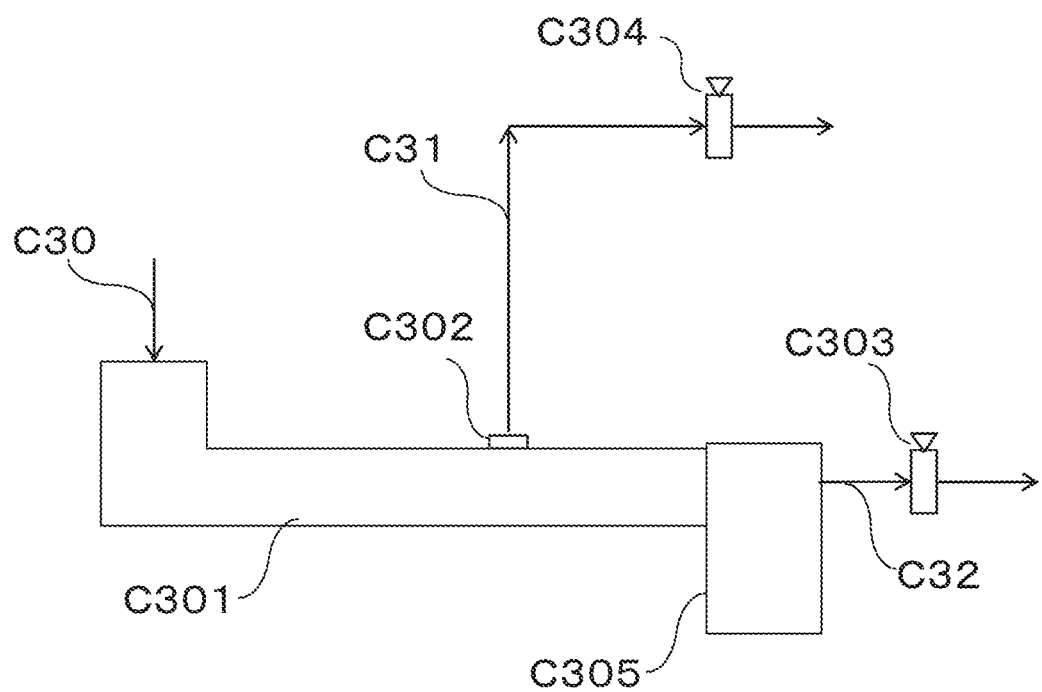
FIG. 10 is a schematic configuration drawing illustrating another example of a collection device to be used in the collection method according to the present invention.

FIG. 10 is a schematic configuration drawing illustrating another example of the collection device used in the collection method according to the present embodiment, in which an extruder (2) is used as a reactor.

The collection device shown in FIG. 10 contains: an extruder C301 in which a liquid phase component formed as a by-product in the step for producing the compound (I) and water are reacted; a vent port C302 configured to extract a gas phase component formed as a by-product by the decomposition reaction in the extruder C301; a pressure-holding valve C304 configured to maintain the pressure to discharge the gas phase component from the vent port C302; a receiver C305 in which the liquid phase component discharged from the extruder C301 is collected; a pressure-holding valve C303 configured to maintain the pressure to discharge the liquid phase component from the receiver C305; a line C30 configured to supply the liquid phase component formed as a by-product in the step for producing the compound (I), water and a compound (III) to the extruder C301; a line C31 configured to discharge the gas phase component extracted from the vent port C302; and a line C32 configured to discharge the liquid phase component from the receiver C305.

Figure 11:
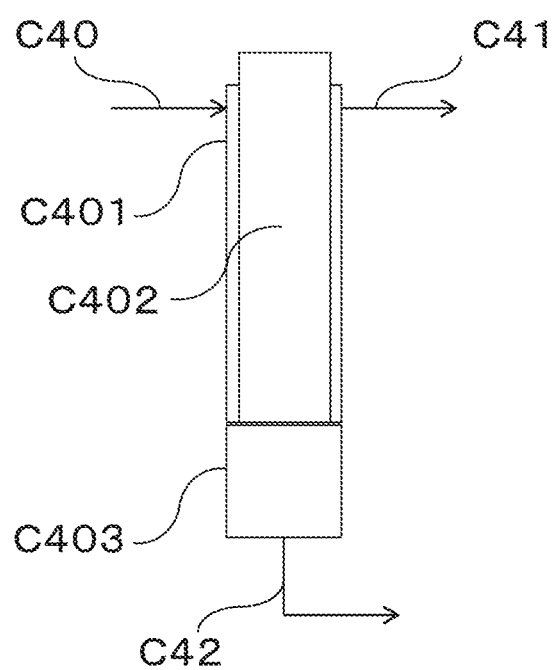
FIG. 11 is a schematic configuration drawing illustrating another example of a collection device to be used in the collection method according to the present invention.

FIG. 11 is a schematic configuration drawing illustrating one example of a collection device used in the collection method according to the present embodiment, in which a thin-film evaporator (3) is used as a reactor.

The collection device shown in FIG. 11 contains: a thin-film evaporator C402 equipped with a heated evaporation surface C401 on which a liquid phase component formed as a by-product in the step for producing the compound (I) and water are reacted; a collection part C403 in which the liquid phase component generated in the decomposition reaction in the heated evaporation surface C401 is collected; a line C40 configured to supply the liquid phase component formed as a by-product in the step for producing the compound (I), water and a compound (III) to the thin-film evaporator C402; a line C41 configured to discharge the gas phase component generated as a by-product on the heated evaporation surface B601; and a line C42 configured to discharge the liquid phase component from the collection part C403.

Figure 7:
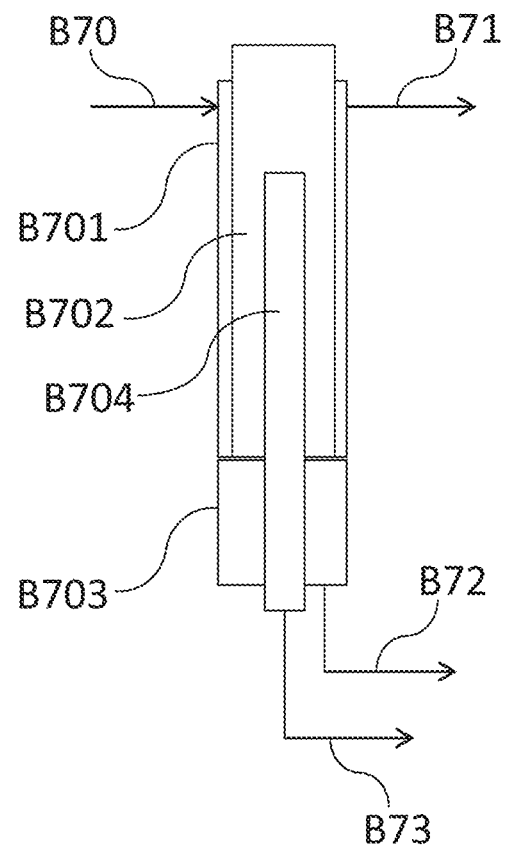
FIG. 7 is a schematic configuration drawing illustrating another example of a collection device to be used in the collection method according to the present invention.

FIG. 7 is a schematic configuration drawing illustrating another example of the collection device used in the collection method according to the present embodiment, in which a thin-film evaporator (3) is used as a reactor.

The collection device shown in FIG. 7 contains: a thin-film evaporator B702 having both a heated evaporation surface B701 on which a liquid phase component formed as a by-product in the step for producing the compound (1) and an active hydrogen-containing compound are reacted, and a condenser B704 in which a gas phase component formed as a by-product by the decomposition reaction on the heated evaporation surface B701 is cooled; a collection part B703 in which the liquid phase component generated in the decomposition reaction on the heated evaporation surface B701 is collected; a line B70 configured to supply the liquid phase component formed as a by-product in the step for producing the compound (1) to the thin-film evaporator B702; a line B71 configured to discharge the gas phase components that are not condensed in the condenser B704; a line B73 configured to discharge the condensed liquid obtained by cooling in the condenser B704; and a line B72 configured to discharge the liquid phase component collected in the collection part B703.

The steps (5) to (7) are preferably conducted in the present embodiment in the same way as the first embodiment.

EXAMPLES

Although the present embodiment will be explained below in detail with reference to Examples and Comparative Examples, the present embodiment is not limited to these examples. Hereinafter, the term "%" means "% by mass" and the term "ppm" means "ppm by mass".

<Analysis Method>
(1) NMR Analysis Method
Device: JNM-A400 FT-NMR system manufactured by JEOL LTD., in Japan.
Preparation of $^1$H-NMR analysis sample
0.3 g of a sample solution was weighed, and then 0.7 g of deuterated chloroform and 0.05 g of tetramethyltin as an internal standard substance were added thereto and mixed uniformly to obtain a NMR analysis sample.

Quantitative Analysis Method
Each standard substance was subjected to analysis to prepare a standard curve, and the quantitative analysis of each analysis sample solution was conducted based on the standard curve.
(2) Gas Chromatography Analysis Method
Device: GC-14B manufactured by Shimadzu Corporation in Japan.
Column: Porapack N having a diameter of 3 mm, a length of 3 m, and made of SUS.
Column temperature: 60° C.
Injection inlet temperature: 120° C.
Carrier gas: Helium
Carrier gas flow rate: 40 mL/min
Detector: FID (flame ionization detector)
Gas chromatography analysis sample
1.0 g of a sample solution was weighed, and then 10 g of toluene and 0.1 g of n-hexane as an internal standard substance were added thereto and mixed uniformly to obtain a gas chromatography analysis sample.
(3) Liquid Chromatography Analysis Method
Device: LC-10AT manufactured by Shimadzu Corporation in Japan.
Column: Inertsil ODS having a particle size of 5 μm, an inner diameter of 2.1 mm and a length of 250 mm.
Column temperature: 40° C.
Developing solvent: water/acetonitrile=90/10
Developing solvent flow rate: 1 mL/min
Detector: Photodiode array detector
Liquid chromatography analysis sample
1.0 g of a sample solution was weighed, and then 10 g of acetic acid was added thereto and mixed uniformly to obtain a liquid chromatography analysis sample.
Quantitative Analysis Method
Each standard substance was subjected to analysis to prepare a standard curve, and the quantitative analysis of each analysis sample solution was conducted based on the standard curve.

Example 1

Step (1-A): Step for obtaining a liquid phase component containing a high-boiling point compound formed as a by-product in the preparation of a compound (I).
(Preparation of Carbamate)
A device shown in FIG. 12 was used.
A mixture composed of 9.8 kg of toluene-2,4-diamine, 10.3 kg of urea, and 261.9 kg of 4-(1,1,3,3-tetramethylbutyl) phenol was supplied at 90 kg/Hr via a line A1 to a continuous multistage distillation column A101.

The continuous multistage distillation column A101 was a device in which a carbamate-forming step was conducted, the column bottom temperature thereof was set at 250° C. and the column top pressure thereof was set at 5 kPa by conducting heating using a reboiler A111.

The reaction liquid was extracted at 90.7 kg/Hr from the bottom part of the continuous multistage distillation column A101.

The gas phase component was extracted from the column top part of the continuous multistage distillation column A101, to be introduced via a line A3 into a condenser A103. The gas phase component introduced into the condenser A103 was cooled to 100° C. in the condenser A103 to obtain a mixture liquid composed of 4-(1,1,3,3-tetramethylbutyl) phenol and urea. The mixture liquid composed of 4-(1,1,3, 3-tetramethylbutyl)phenol and urea obtained in the condenser A103 was supplied at 9 kg/Hr via a line A4 to the line A1.

The gas phase components that are not condensed in the condenser A103 were discharged via a line A9 from the condenser A103.

(Thermal Decomposition of Carbamate)

The reaction liquid was supplied from the bottom part of the continuous multistage distillation column A101 via a line A5 to a thermal decomposition device A102. The thermal decomposition device A102 was a device in which an isocyanate was produced by a thermal decomposition reaction of a carbamate, and was composed of: a tubular reactor; and a separation tank in which a liquid phase component and a gas phase component containing an isocyanate were separated. The internal pressure was set at 1 kPa, and the device was heated externally at 250° C.

The gas phase component generated in the thermal decomposition device A102 was supplied at 8 m/second from a line A7 to the separation column A109 to separate 4-(1,1,3,3-tetramethylbutyl)phenol and 2,4-toluene diisocyanate. The heat quantity required to conduct distillation separation was supplied by a reboiler A112.

The 4-(1,1,3,3-tetramethylbutyl)phenol was collected from the column bottom of the separation column A109 via a line A18.

The component containing the 2,4-toluene diisocyanate was collected from the column top of the separation column A109, and then supplied via a condenser A114 and a line A20 to a purification column A110, to conduct distillation purification of 2,4-toluene diisocyanate. The heat quantity required to conduct distillation purification was supplied by a reboiler A113.

The 2,4-toluene diisocyanate was collected at 2.4 kg/Hr from the column top of the purification column A110 via a condenser A115 and a line A17.

The component present at the column bottom of the purification column A110 was extracted from a line A19.

A partial amount of the liquid phase component collected from the bottom part of the thermal decomposition device A102 was collected via a line A8 to be supplied at a liquid temperature of 180° C. to the following step (1-1) as a liquid phase component containing a high-boiling point compound. The remaining liquid phase component was supplied via a line A6 to the thermal decomposition device A102 again. At the time, the flow rate per wetted perimeter at the bottom part of the thermal decomposition device A102 was 50 kg/m-hour.

The viscosity of the liquid phase component collected from the line A8 at 150° C. was 70 mPa·s.

The liquid phase component collected from the line A8 was analyzed by $^1$H-NMR to confirm that 0.90 mol of carbamate bonds, 0.13 mol of groups (II-1) and (11-2) in total, 0.12 mol of allophanate bonds and isocyanurate bonds in total, and 0.22 mol of Fries rearrangement terminals were contained per kg of the liquid phase component.

In addition, as a result of the liquid chromatography analysis, it was confirmed that the liquid phase component contained a compound of the following formula (1-a-1), a compound of the following formula (1-b-1), and 57% by mass of 4-(1,1,3,3-tetramethylbutyl)phenol.

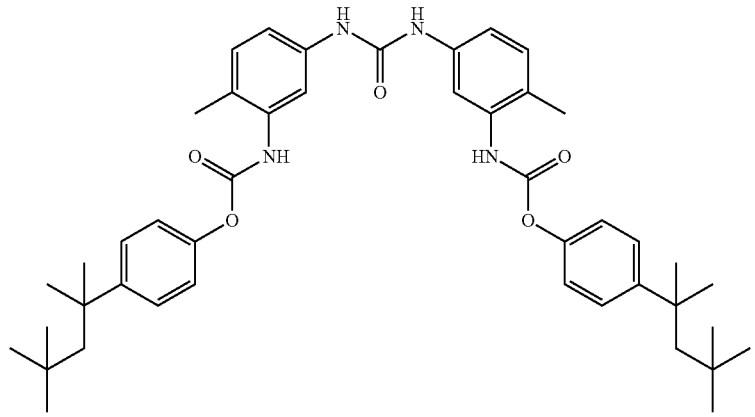

(1-a-1)

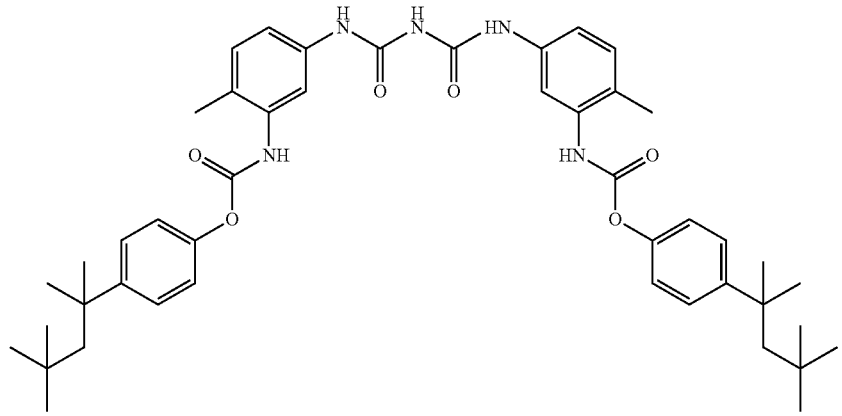

(1-b-1)

Step (1-1): Step for reacting the liquid phase component containing the high-boiling point compound and an active hydrogen-containing compound.

A device shown in FIG. 1 was used. 50 kg of the liquid phase component containing the high-boiling point compound collected from a line A8 was supplied to a pressure-resistant reactor B101 via a line B1 while maintaining the temperature thereof at 180° C. Then, 100 kg of water was supplied to the pressure-resistant reactor B101 to obtain a mixture liquid. The pressure-resistant reactor B101 was heated at 280° C. and at a pressure of 6.5 MPa for 5 hours.

Step (1-2): Step for returning a condensed liquid obtained by cooling the gas phase component to the reactor.

The gas phase component in the pressure-resistant reactor B101 at the step (1-1) was introduced into a condenser B102 via a line B3. The gas phase component introduced into the condenser B102 was cooled in the condenser B102 to 10° C. to obtain a condensed liquid, and then the condensed liquid was returned to the pressure-resistant reactor B101 via a line B2. The step was continually conducted during the step (1-1).

Step (1-3): Step for discharging a gas phase component that was not condensed to the outside of the reactor.

The gas phase components that were not condensed in the step (1-2) were extracted from a pressure-holding valve B104 through a line B4 as a gas component (the main component of which was confirmed to be carbon dioxide as a result of analysis). The step was continually conducted during the step (1-1).

Step (1-4): Step for discharging the reaction liquid to the outside of the reactor After the step (1-1) was conducted and then the reaction liquid was cooled, the reaction liquid was collected through a line B5 in a storage tank B103. The reaction liquid was subjected to a gas chromatography analysis to confirm that 8.3 mol of toluene-2,4-diamine was contained.

Step (1-5): Step for separating a compound (III)

The collected reaction liquid was distilled under reduced pressure to collect a crude toluene-2,4-diamine at a yield of 80%.

Step (1-6): Step for purifying the compound (III)

The crude toluene-2,4-diamine collected in the step (1-5) was subjected to distillation purification. The purity of the collected toluene-2,4-diamine was 99% by mass or more (including a margin of error in the gas chromatography analysis). The amount of metallic atoms was less than 1000 ppm, and that of halogen atoms was less than 1000 ppm, relative to the total mass of toluene-2,4-diamine.

Step (1-7): Step for Separating a Compound (V)

The residual liquid remaining after collecting the compound (III) in the step (1-5) was distilled under reduced pressure to collect a crude 4-(1,1,3,3-tetramethylbutyl)phenol at a yield of 81%.

Step (1-8): Step for purifying the compound (V)

The crude 4-(1,1,3,3-tetramethylbutyl)phenol collected in the step (1-7) was subjected to distillation purification. The purity of the collected 4-(1,1,3,3-tetramethylbutyl)phenol was 99% by mass or more (including a margin of error in the gas chromatography analysis). The amount of metallic atoms was less than 1000 ppm, and that of halogen atoms was less than 1000 ppm, relative to the total mass of 4-(1,1,3,3-tetramethylbutyl)phenol.

Step (1-B): Preparation of compound (I) by reusing the collected compound (III) and compound (V).

The toluene-2,4-diamine and the 4-(1,1,3,3-tetramethylbutyl)phenol, collected in the steps (1-6) and (1-8), were used, and the deficient amounts of toluene-2,4-diaimine and 4-(1,1,3,3-tetramethylbutyl)phenol, were newly added, to be supplied through the line A1 to the continuous multistage distillation column A101 to conduct the step (1-A), and 2,4-toluene diisocyanate was collected from a line 17 at 2.4 kg/Hr.

Example 2

Step (2-A)
(Preparation of Carbamate)

Figure 13:
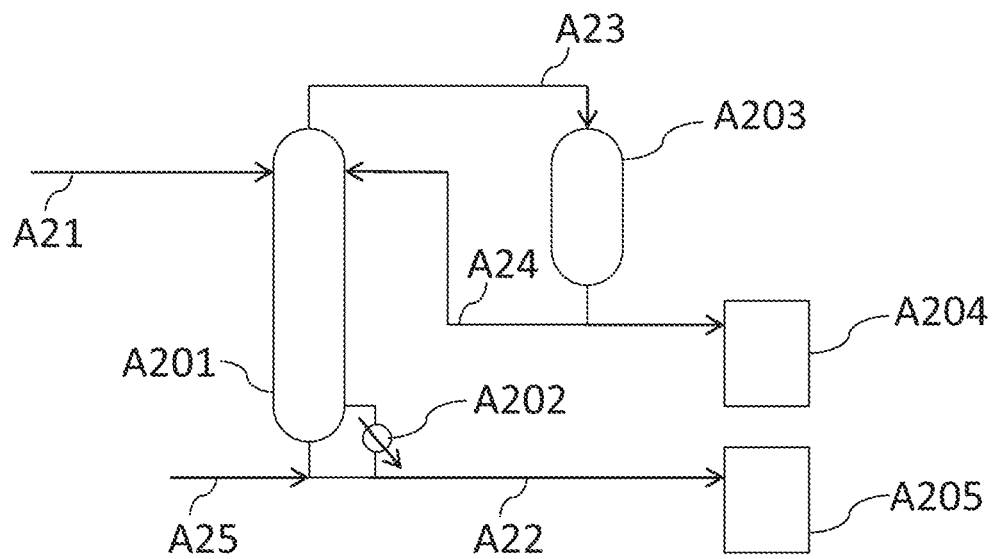
FIG. 13 is an explanation drawing illustrating a carbamate production facility used in the step (2-A) in Example 2.

A device shown in FIG. 13 was used to conduct carbamate-forming reaction.

A mixture composed of 11.3 kg of 1-amino-3-aminomethyl-3,5,5-trimethylcyclohexane, 15.1 kg of urea, and 220.3 kg of 1-butanol was supplied at 20 kg/Hr via a line A21 to a continuous multistage distillation column A201. 1-Butanol was supplied appropriately from a line A25.

The gas phase component generated in the continuous multistage distillation column A201 was introduced via a line A23 into a condenser A203. The gas phase component introduced into the condenser A203 was cooled to 0° C. to obtain a mixture liquid composed of 1-butanol and urea. A partial amount of the mixture liquid was supplied through a line A24 at 3.5 kg/Hr to the continuous multistage distillation column A201, and the remaining mixture liquid was collected in a storage tank A204.

The continuous multistage distillation column A201 was a device in which the carbamate-forming step is conducted, and the column bottom temperature was set at 220° C. and the column top pressure was set at 1.2 MPa by conducting heating using a reboiler A202.

The reaction liquid was extracted from the bottom part of the continuous multistage distillation column A201 to collect the reaction liquid via a line A22 in a storage tank A205.

(Preliminary Condensation)

Figure 14:
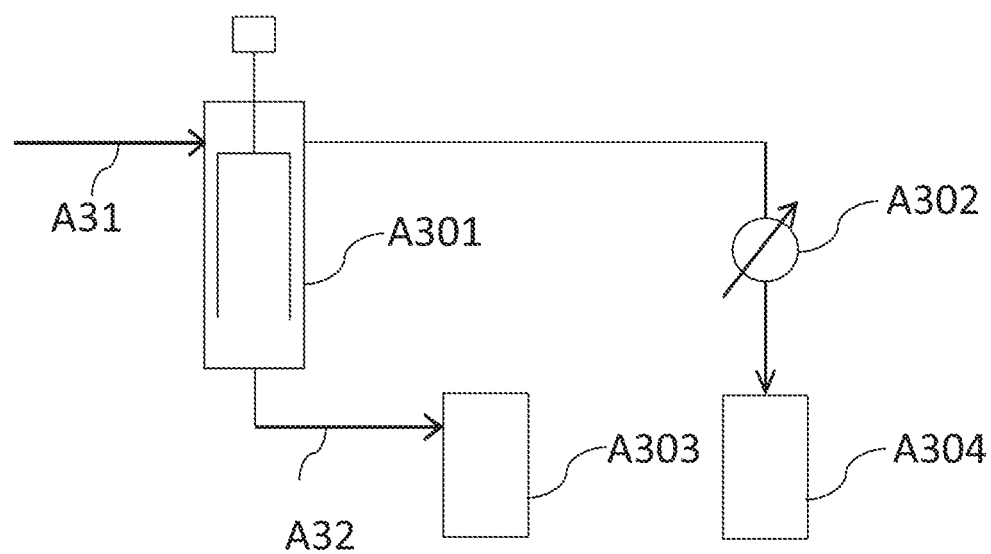
FIG. 14 is an explanation drawing illustrating a device used in a preliminary condensation step in Example 2.

The preliminary condensation step was conducted using a device shown in FIG. 14. The reaction liquid collected in the storage tank A205 at the carbamate-forming step was supplied through a line A31 at 21 kg/Hr to a thin-film evaporator A301. The temperature of the heated evaporation surface of the thin-film evaporator A301 was set at 130° C., and the internal pressure thereof was set at 70 kPa.

The gas phase component generated in the thin-film evaporator A301 was condensed in a condenser A302, and collected in a storage tank A304. The collected product was 1-butanol.

In contrast, the liquid phase component generated in the thin-film evaporator A301 was collected through a line A32 in a storage tank A303 at 10 kg/Hr.

(Thermal Decomposition of Carbamate)

Figure 15:
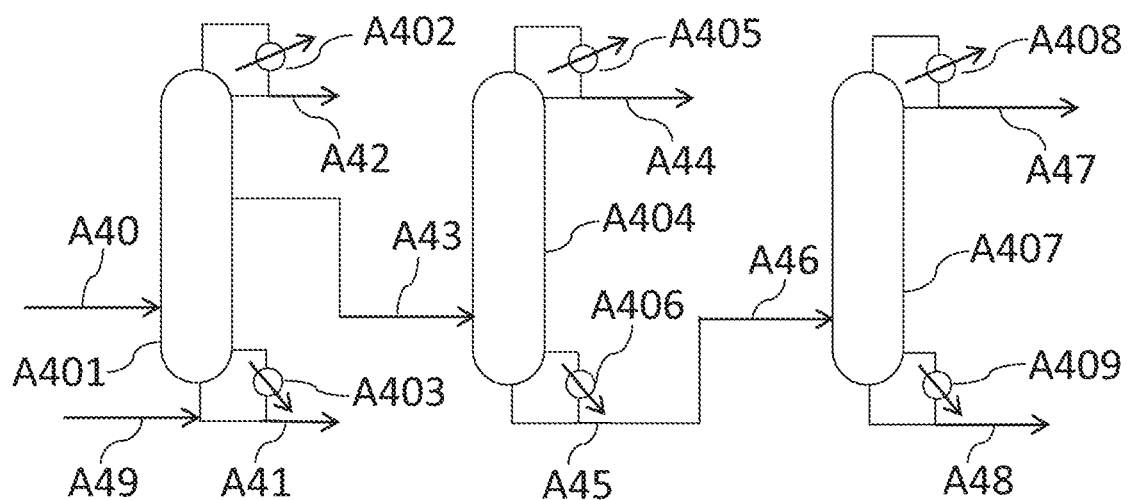
FIG. 15 is an explanation drawing illustrating a device used in a step for thermally decomposing carbamate in Example 2.

The thermal decomposition step was conducted using a device shown in FIG. 15. A thermal decomposition device A401 was a multistage distillation column in which an isophorone diisocyanate was produced by a thermal decomposition reaction of N-substituted carbamate, and the total reflux state of dibenzyl ether was realized at a column top pressure at 25 kPa by conducting heating using a reboiler A403. The liquid phase component collected in the storage tank A303 at the preliminary condensation step was supplied thereto via a line A40 at 5 kg/Hr, and dibenzyl ether was supplied thereto via a line A49. The gas phase component was extracted from the column top and collected via a condenser A402 from a line A42, and the liquid phase component was collected from a line A41.

A fraction containing isophorone diisocyanate was collected from a line A43 formed in the middle stage of the thermal decomposition device A401, and then supplied to a separation column A404. The gas phase component containing 1-butanol was subjected to distillation separation in the separation column A404, to collect the gas phase component via a condenser A405 from a line A44. The heat quantity required to conduct distillation separation was supplied from a reboiler A406.

The liquid phase component collected from the column bottom part of the separation column A404 was supplied to a separation column A407 via a line A45 and a line A46. In the separation column A407, the liquid phase component was subjected to distillation separation to be collected from a line A48. The heat quantity required to conduct distillation separation in the separation column A407 was supplied from a reboiler A409.

The gas phase component collected from the column top of the separation column A404 was condensed in a condenser A408 to collect isophorone diisocyanate from a line A47.

The liquid phase component collected from a line A41 was used as a liquid phase component containing a high-boiling point compound according to the present embodiment.

The viscosity of the liquid phase component containing the high-boiling point compound at 150° C. was 40 mPa·s.

The liquid phase component was analyzed by $^1$H-NMR to confirm that 2.56 mol of carbamate bonds, 0.14 mol of groups (II-1) and (II-2) in total, 0.10 mol of allophanate bonds and isocyanurate bonds in total, and dibenzyl ether were contained per kg of the liquid phase component.

It was confirmed as a result of the analysis of the liquid phase component by liquid chromatography that a compound of the following formula (2-a-1) and a compound of the following formula (2-b-1) were contained.

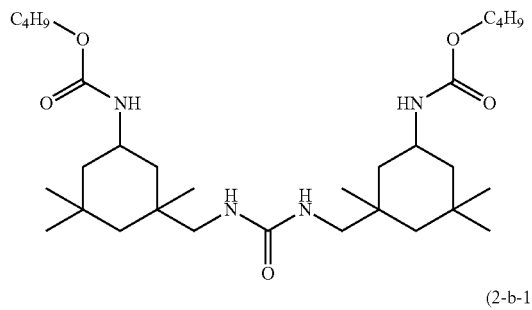

(2-a-1)

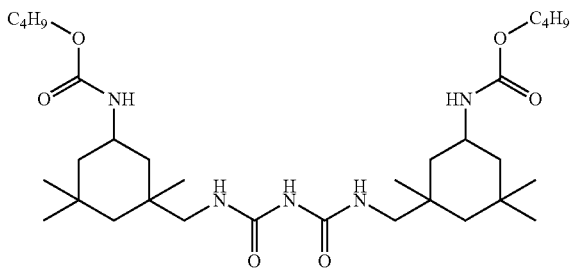

(2-b-1)

Step (2-1): Step for reacting the liquid phase component containing the high-boiling point compound and an active hydrogen-containing compound.

A device shown in FIG. 2 was used. 50 kg of the liquid phase component containing the high-boiling point compound collected via a line A41 was supplied to a pressure-resistant reactor B201 via a line B20 while maintaining the temperature thereof at 180° C.

100 kg of water and 16 kg of ethanol were added to the pressure-resistant reactor B201, followed by circulating the liquid phase component through a line B21 and a line B22 using a pump B202 to allow the reaction to proceed at 250° C. and 4.3 MPa for 5 hours.

Step (2-2): Step for returning a condensed liquid obtained by cooling the gas phase component to the inside of the reactor The gas phase component in the pressure-resistant reactor B201 at the step (2-1) was introduced via a line B24 into a condenser B203. The introduced gas phase component was cooled in the condenser B203 at 10° C. to obtain a condensed liquid, and the condensed liquid was returned via a line B23 to the pressure-resistant reactor B201. The step was continually conducted during the step (2-1).

Step (2-3): Step for discharging a gas phase component that was not condensed to the outside of the reactor.

The gas phase components that were not condensed in the step (2-2) were extracted from a pressure-holding valve B204 through a line B26 as a gas component (the main component of which was confirmed to be carbon dioxide as a result of analysis). The step was continually conducted during the step (2-1).

Step (2-4): Step for discharging the reaction liquid to the outside of the reactor After the step (2-1) was conducted and then the reaction liquid was cooled, the reaction liquid was collected through a line B25 in a storage tank B205.

The reaction liquid was subjected to a gas chromatography analysis to confirm that 1-amino-3-aminomethyl-3,5,5-trimethylcyclohexane was contained.

Step (2-5): Step for separating a compound (III)

The collected reaction liquid was distilled under reduced pressure to collect a crude 1-amino3-aminomethyl-3,5,5-trimethylcyclohexane at a yield of 90%.

Step (2-6): Step for purifying the compound (III)

The crude 1-amino-3-aminomethyl-3,5,5-trimethylcyclohexane collected in the step (2-5) was subjected to distillation purification. The purity of the collected 1-amino-3-aminomethyl-3,5,5-trimethylcyclohexane was 99% by mass or more (including a margin of error in the gas chromatography analysis). The amount of metallic atoms was less than 1000 ppm, and that of halogen atoms was less than 1000 ppm, relative to the total mass of 1-amino-3-aminomethyl-3,5,5-trimethylcyclohexane.

Example 3

Step (3-A): Step for obtaining a liquid phase component containing the high-boiling point compound formed as a by-product in the preparation of a compound (I)

(Preparation of Carbamate)

Figure 16:
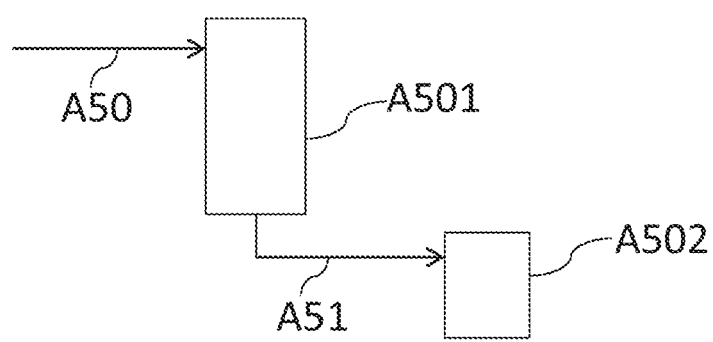
FIG. 16 is an explanation drawing illustrating a carbamate production facility used in Examples 3 and 4.

A device shown in FIG. 16 was used.

50 kg of phenol was supplied via a line 50 to a stirring tank A501, and then 38 kg of diphenyl carbonate was supplied thereto to obtain a uniform solution. 15 kg of 4,4'-dicyclohexylmethane diamine was added thereto slowly while maintaining the temperature of the stirring tank A501 at 40° C. After the addition was completed, stirring was conducted for 5 hours, followed by transferring the reaction liquid via a line A51 to a storage tank 502.

(Thermal Decomposition of Carbamate)

Dicyclohexylmethane diisocyanate and a liquid phase component containing a high-boiling point compound were obtained by the same method as that of the "thermal decomposition of carbamate" in Example 2.

The viscosity of the liquid phase component containing the high-boiling point compound at 150° C. was 50 mPa·s.

The liquid phase component containing the high-boiling point compound was analyzed by $^1$H-NMR to confirm that 2.67 mol of carbamate bonds, 0.17 mol of groups (II-1) and (II-2) in total, 0.62 mol of allophanate bonds and isocyanurate bonds in total, 0.02 mol of Fries rearrangement terminals, and dibenzyl ether were contained per kg of the liquid phase component.

It was confirmed as a result of a liquid chromatography analysis of the liquid phase component containing the high-boiling point compound that the liquid phase component containing the high-boiling point compound contained a compound of the following formula (3-a-1) and a compound of the following formula (3-b-1).

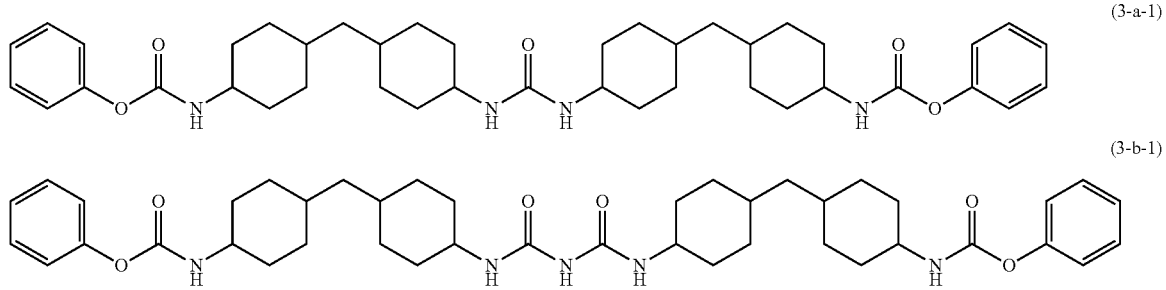

(3-a-1)

(3-b-1)

Step (3-1): Step for reacting the liquid phase component containing the high-boiling point compound and an active hydrogen-containing compound.

A device shown in FIG. 3 was used.

50 kg of the liquid phase component containing the high-boiling point compound collected in the step (3-A) was supplied to a stirring tank B301 via a line B30 while maintaining the temperature thereof at 180° C.

100 kg of water and 50 kg of methanol were added to the stirring tank B301 to obtain a uniform solution at 250° C. and 4.9 MPa. The solution was supplied continuously through a line B33 to a stirring tank B302 heated at 250° C. and pressurized at 4.9 MPa.

The gas phase component generated in the stirring tank B302 was introduced via a line B34 into the stirring tank B301.

Step (3-2): Step for returning a condensed liquid obtained by cooling the gas phase component to the inside of the reactor The gas phase component in the pressure-resistant reactor B301 at the step (3-1) was introduced via a line B32 into a condenser B303. The introduced gas phase component was cooled in the condenser B303 at 5° C. to obtain a condensed liquid. The obtained condensed liquid was returned via a line B31 to the stirring tank B301. The step was continually conducted during the step (3-1).

Step (3-3): Step for discharging a gas phase component that was not condensed to the outside of the reactor.

The gas phase components that were not condensed in the step (3-2) were extracted from a pressure-holding valve B304 through a line B36 as a gas component (the main component of which was confirmed to be carbon dioxide as a result of analysis). The step was continually conducted during the step (3-1).

Step (3-4): Step for discharging the reaction liquid to the outside of the reactor The reaction liquid in the step (3-1) was collected from the bottom part of the stirring tank B302 via a line 35 in a storage tank B305. An average residence time was 3 hours.

The reaction liquid was subjected to a gas chromatography analysis to confirm that 4, 4'-dicyclohexylmethanediainine was contained.

Step (3-5): Step for separating a compound (III)

The collected reaction liquid was distilled under reduced pressure to collect a crude 4, 4'-dicyclohexylmethanediamine at a yield of 90%.

Step (3-6): Step for purifying the compound (III)

The crude 4, 4'-dicyclohexylmethanediamine collected in the step (3-5) was subjected to distillation purification.

The purity of the collected 4, 4'-dicyclohexylmethanediamine was 99% by mass or more (including a margin of error in the gas chromatography analysis). The amount of metallic atoms was less than 1000 ppm, and that of halogen atoms was less than 1000 ppm, relative to the total mass of 4, 4'-dicyclohexylmethanediamine.

Example 4

Step (4-A): Step for obtaining a liquid phase component containing a high-boiling point compound formed as a by-product in the preparation of a compound (I)

(Preparation of Carbamate)

A reaction liquid was obtained by the same method as that of the "preparation of carbamate" in Example 3 using a device shown in FIG. 16, except that 50 kg of phenol, 38 kg of diphenyl carbonate, and 8.2 kg of 1,6-hexamethylenediamine were used. It was confirmed as a result of a liquid chromatography analysis of the reaction liquid that a carbamate of the following formula (4-1) was produced at a yield of 95%, relative to 1,6-hexamethylenediamine.

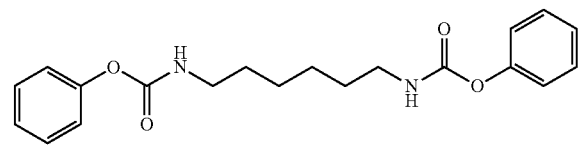

(4-1)

(Ester Exchange Reaction)

Figure 17:
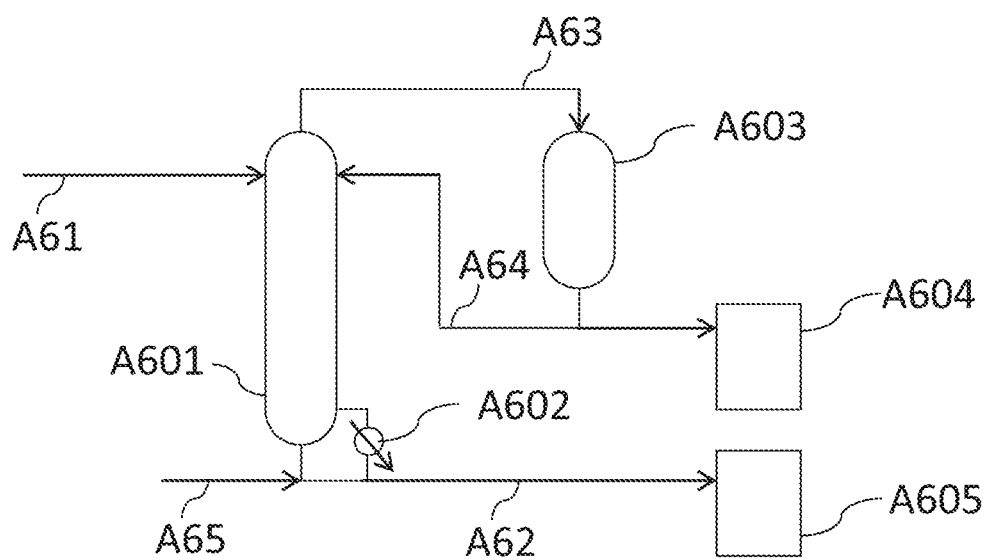
FIG. 17 is an explanation drawing illustrating a device used in ester exchange reaction in Example 4.

A device shown in FIG. 17 was used.

4-(α,α-Dimethylbenzyl)phenol was supplied via a line A65 to a multistage distillation column A601, and then heated using a reboiler A602 to realize total reflux state in the multistage distillation column A601. The reaction liquid obtained by the "preparation of carbamate" was supplied thereto through a line A61 to conduct an ester exchange reaction of the compound of the formula (4-1). A gas phase component containing phenol generated by the ester exchange reaction was supplied via a line A63 to a condenser A603. A partial amount of a condensed liquid obtained by cooling the gas phase component at 100° C. in the condenser A603 was supplied via a line A64 to a multistage distillation column A601, and the remaining condensed liquid was collected in a storage tank A604. The resultant reaction liquid was collected via a line A62 in a storage tank A605.

It was confirmed as a result of a liquid chromatography analysis of the reaction liquid that a compound of the following formula (4-2) was produced at a yield of 95%, relative to the compound of formula (4-1).

Step (4-1): Step for reacting the liquid phase component containing the high-boiling point compound and an active hydrogen-containing compound.

A device shown in FIG. 4 was used.

50 kg of the liquid phase component containing the high-boiling point compound collected in the step (4-A) was supplied via a line B40 to an extruder B401 heated at 280° C. and pressurized at 6.7 MPa while maintaining the temperature of the liquid phase component at 180° C.

100 kg of water, relative to 50 kg of the liquid phase component containing the high-boiling point compound, was added continuously to the extruder B401.

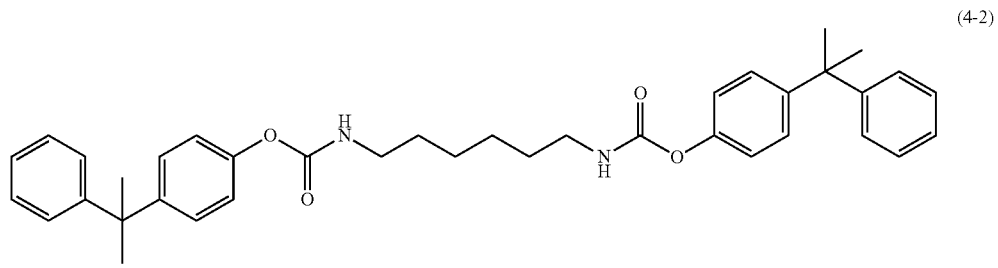 [SMILES: CC(C)(c1ccccc1)c1ccc(OC(=O)NCCCCCCNC(=O)Oc2ccc(C(C)(C)c3ccccc3)cc2)cc1]

(4-2)

(Thermal Decomposition of Carbamate)

A liquid phase component containing a high-boiling point compound was obtained by the same method as that of the "thermal decomposition of carbamate" in Example 1.

The liquid phase component containing the high-boiling point compound was analyzed by $^1$H-NMR to confirm that 2.05 mol of carbainate bonds, 0.19 mol of groups (II-1) and (II-2) in total, 0.48 mol of allophanate bonds and isocyanurate bonds in total, 0.02 mol of Fries rearrangement terminals, and 1.25 mol of 4-(α,α-dimethylbenzyl)phenol were contained per kg of the liquid phase component.

It was confirmed as a result of a liquid chromatography analysis of the liquid phase component containing the high-boiling point compound that the liquid phase component containing the high-boiling point compound contained a compound of the following formula (4-a-1) and a compound of the following formula (4-b-1).

Step (4-2): Step for returning a condensed liquid obtained by cooling the gas phase component to the inside of the reactor The gas phase component in the extruder B401 at the step (4-1) was extracted via a line 41 from a vent port B402 formed on the extruder B401 and then introduced into a condenser B405. The introduced gas phase component was cooled in the condenser B405 to obtain a condensed liquid. The obtained condensed liquid was returned via a line B43 to the extruder B401. The step was continually conducted during the step (4-1).

Step (4-3): Step for discharging a gas phase component that was not condensed to the outside of the reactor.

The gas phase components that were not condensed in the step (4-2) were extracted from a pressure-holding valve B404 through a line B44 as a gas component (the main

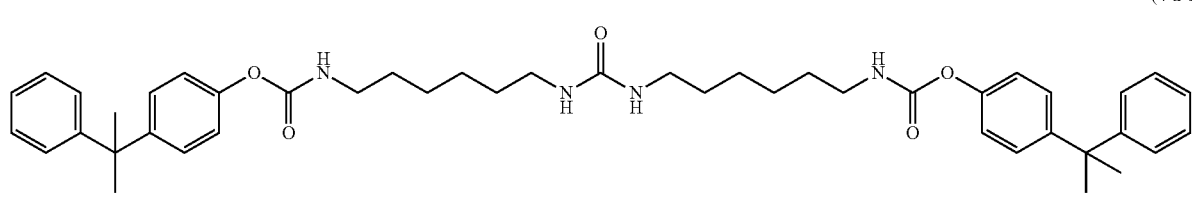

(4-a-1)

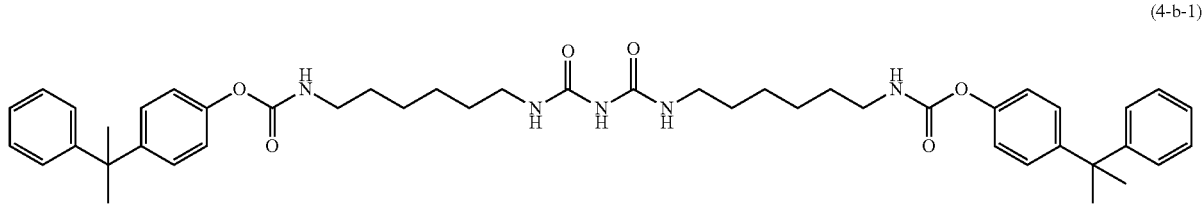

(4-b-1)

component of which was confirmed to be carbon dioxide as a result of analysis). The step was continually conducted during the step (4-1).

Step (4-4): Step for discharging the reaction liquid to the outside of the reactor The reaction liquid in the step (4-1) was collected from a discharge outlet of the extruder 401 via a line 42 with a pressure-holding valve B403 in a storage tank B406.

The reaction liquid was subjected to a gas chromatography analysis to confirm that 1,6-hexamethylenediamine was contained.

Step (4-5): Step for Separating a Compound (III)

The collected reaction liquid was distilled under reduced pressure to collect a crude 1,6-hexamethylenediamine at a yield of 78%.

Step (4-6): Step for purifying the compound (III)

The crude 1,6-hexamethylenediamine collected in the step (4-5) was subjected to distillation purification. The purity of the collected 1,6-hexamethylenediamine was 99% by mass or more (including a margin of error in the gas chromatography analysis). The amount of metallic atoms was less than 1000 ppm, and that of halogen atoms was less than 1000 ppm, relative to the total mass of 1,6-hexamethylenediamine.

Step (4-7): Step for separating a compound (V)

The residual liquid remaining after collecting 1,6-hexamethylenediamine in the step (4-5) was distilled under reduced pressure to collect a crude 4-(α,α-dimethylbenzyl)phenol at a yield of 74%.

Step (4-8): Step for purifying the compound (V)

The crude 4-(α,α-dimethylbenzyl)phenol collected in the step (4-7) was subjected to distillation purification. The purity of the 4-(α,α-dimethylbenzyl)phenol was 99% by mass or more (including a margin of error in the gas chromatography analysis). The amount of metallic atoms was less than 1000 ppm, and that of halogen atoms was less than 1000 ppm, relative to the total mass of 4-(α,α-dimethylbenzyl)phenol.

Example 5

Step (5-A): Step for obtaining a liquid phase component containing a high-boiling point compound formed as a by-product in the preparation of a compound (I)
(Preparation of Ureido-Containing Compound)

Figure 18:
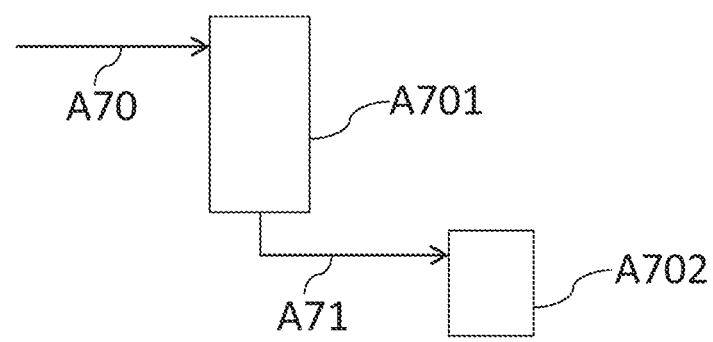
FIG. 18 is an explanation drawing illustrating a production device used in the step (5-1) in Example 5 to produce a compound having an ureido group.

A device shown in FIG. 18 was used.

10.3 kg of urea and 261.9 kg of 4-(1,1,3,3-tetramethylbutyl)phenol were supplied via a line A70 to a stirring tank A701. After obtaining a uniform solution at 130° C., 9.8 kg of toluene-2,4-diamine was added thereto, and then stirred for 5 hours to collect the reaction liquid via a line 71 in the storage tank 702.

It was confirmed as a result of a liquid chromatography analysis of the reaction liquid that a compound of the following formula (5-1) was produced at a yield of 90%, relative to toluene-2,4-diamine.

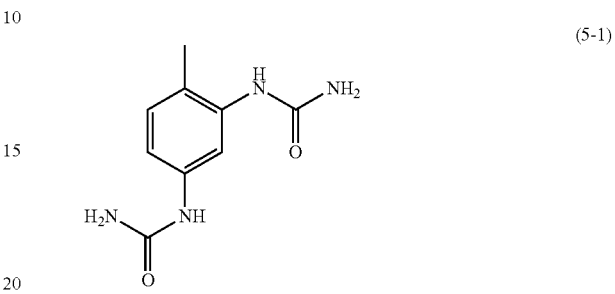

(5-1)

(Preparation of Carbamate)

The same method as that of "preparation of carbamate" in Example 1 was conducted, except that the reaction liquid obtained by the "preparation of ureido-containing compound" was supplied at 90 kg/Hr via a line A1 to a continuous multistage distillation column A101.

(Thermal Decomposition of Carbamate)

The same method as that of the "thermal decomposition of carbamate" in Example 1 was conducted to obtain a liquid phase component containing a high-boiling point compound.

The viscosity of the resultant liquid phase component at 150° C. was 82 mPa·s.

The liquid phase component containing the high-boiling point compound was analyzed by $^1$H-NMR to confirm that 1.33 mol of carbamate bonds, 0.10 mol of groups (II-1) and (II-2) in total, 0.10 mol of allophanate bonds and isocyanurate bonds in total, and 0.16 mol of Fries rearrangement terminals were contained per kg of the liquid phase component.

It was confirmed as a result of a liquid chromatography analysis of the liquid phase component containing the high-boiling point compound that the liquid phase component containing the high-boiling point compound contained a compound of the following formula (5-a-1), a compound of the following formula (5-b-1), and 42% by mass of 4-(1,1,3,3-tetramethylbutyl)phenol.

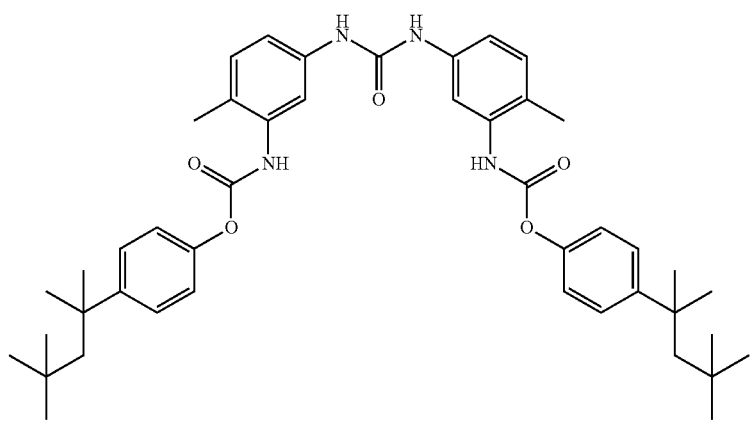

(5-a-1)

(5-b-1)

[Chemical structure diagram]

Step (5-1): Step for reacting the liquid phase component containing the high-boiling point compound and an active hydrogen-containing compound.

A device shown in FIG. 5 was used.

50 kg of the liquid phase component containing the high-boiling point compound collected in the step (5-A) was supplied via a line B50 to an extruder B501 heated at 280° C. and pressurized at 6.7 MPa while maintaining the temperature of the liquid phase component at 180° C.

100 kg of water, relative to 50 kg of the liquid phase component containing the high-boiling point compound, was added continuously to the extruder B501.

Step (5-2): Step for returning a condensed liquid obtained by cooling the gas phase component to the inside of the reactor The gas phase component generated in the extruder B501 at the step (5-1) was extracted via a line 51 from a vent port B502 formed on the extruder B501 and then introduced into a condenser B506. The introduced gas phase component was cooled in the condenser B506 to 10° C. to obtain a condensed liquid. The obtained condensed liquid was returned via a line B53 to the extruder B501. The step was continually conducted during the step (5-1).

Step (5-3): Step for discharging a gas phase component that was not condensed to the outside of the reactor.

The gas phase components that were not condensed in the step (5-2) were extracted from a pressure-holding valve B504 through a line B54 as a gas component (the main component of which was confirmed to be carbon dioxide as a result of analysis). The step was continually conducted during the step (5-1).

Step (5-4): Step for discharging the reaction liquid to the outside of the reactor The reaction liquid collected in a receiver B505 formed at a discharge part of the extruder B501 in the step (5-1) was collected via a line B55 in a storage tank B507.

The collected reaction liquid was subjected to a gas chromatography analysis to confirm that toluene-2,4-diamine was contained.

Step (5-5): Step for separating a compound (III)

The collected reaction liquid was distilled under reduced pressure to collect a crude toluene-2,4-diamine at a yield of 73%.

Step (5-6): Step for purifying the compound (III)

The crude toluene-2,4-diamine collected in the step (5-5) was subjected to distillation purification. The purity of the collected toluene-2,4-diamine was 99% by mass or more (including a margin of error in the gas chromatography analysis). The amount of metallic atoms was less than 1000 ppm, and that of halogen atoms was less than 1000 ppm, relative to the total mass of toluene-2,4-diamine.

Step (5-7): Step for separating a compound (V)

The residual liquid remaining after collecting the compound (III) in the step (5-5) was distilled under reduced pressure to collect a crude 4-(1,1,3,3-tetramethylbutyl)phenol at a yield of 78%.

Step (5-8): Step for purifying the compound (V)

The crude 4-(1,1,3,3-tetramethylbutyl)phenol collected in the step (5-7) was subjected to distillation purification. The purity of the collected 4-(1,1,3,3-tetramethylbutyl)phenol was 99% by mass or more (including a margin of error in the gas chromatography analysis). The amount of metallic atoms was less than 1000 ppm, and that of halogen atoms was less than 1000 ppm, relative to the total mass of 4-(1,1,3,3-tetramethylbutyl)phenol.

Example 6

Step (6-A): Step for obtaining a liquid phase component containing a high-boiling point compound formed as a by-product in the preparation of a compound (I)

A distillate residue (melted product) generated when 2,4-toluene diisocyanate was produced by a reaction of 1,5-pentamethylenediamine and phosgene was obtained. The distillate residue was used as a composition containing a high-boiling point compound.

The liquid phase component containing the high-boiling point compound contained large amounts of insoluble components when a sample was prepared. Only soluble components obtained by conducting filtering were analyzed by $^1$H-NMR to confirm that the presence of a compound having both a group (II-1) and a group (II-2).

Step (6-1):

A device shown in FIG. 6 was used.

50 kg of the distillate residue in the step (6-A) was mixed with 50 kg of water and 30 kg of ethanol while maintaining the temperature thereof at 300° C., followed by supplying the mixture liquid via a line B60 to a thin-film evaporator B602.

The supplied mixture liquid was developed in a thin-film state on a heated evaporation surface B601 heated at 280° C. and at 6.7 MPa.

Step (6-2): Step for returning a condensed liquid obtained by cooling the gas phase component to the inside of the reactor The gas phase component generated as a by-product by the decomposition reaction on the heated evaporation surface B601 at the step (6-1) was extracted from a line B64 and then introduced into a condenser B604. The introduced gas phase component was cooled in the condenser B604 to 10° C. to obtain a condensed liquid. The obtained condensed liquid was returned via a line B63 to the thin-film evaporator B602. The step was continually conducted during the step (6-1).

Step (6-3): Step for discharging a gas phase component that was not condensed to the outside of the reactor.

The gas phase components that were not condensed in the step (6-2) were extracted from a pressure-holding valve B606 through a line B61 as a gas component (the main component of which was confirmed to be carbon dioxide as a result of analysis). The step was continually conducted during the step (6-1).

Step (6-4): Step for discharging the reaction liquid to the outside of the reactor The reaction liquid generated by the decomposition reaction on the heated evaporation surface B601 in the step (6-1) slipped on the heated evaporation surface B601 to be collected in a collection part B603. The component collected in the collection part B603 was collected via a line B62 in a storage tank B605.

The collected reaction liquid was subjected to a gas chromatography analysis to confirm that toluene-2,4-diamine was contained.

Step (6-5): Step for separating a compound (III)

The collected reaction liquid was distilled under reduced pressure to collect a crude 1,5-pentamethylenediamine.

Step (6-6): Step for purifying the compound (III)

The crude 1,5-pentamethylenediamine collected in the step (6-5) was subjected to distillation purification. The purity of the collected 1,5-pentamethylenediamine was 99% by mass or more (including a margin of error in the gas chromatography analysis). The amount of metallic atoms was less than 1000 ppm, and that of halogen atoms was less than 1000 ppm, relative to the total mass of 1,5-pentamethylenediamine.

Example 7

Step (7-A): Step for obtaining a liquid phase component containing the high-boiling point compound formed as a by-product in the preparation of a compound (I).

1,5-Pentamethylenediamine was produced by the same method as that of the step (6-A) in Example 6, and a composition containing a high-boiling point compound was collected.

The liquid phase component containing the high-boiling point compound contained large amounts of insoluble components when a sample was prepared. Only soluble components obtained by conducting filtering were analyzed by $^1$H-NMR to confirm that the presence of a compound having both a group (II-1) and a group (II-2).

Step (7-1):

A device shown in FIG. 7 was used.

50 kg of the distillate residue in the step (7-A) was mixed with 50 kg of water and 25 kg of 1,5-pentamethylenediamine while maintaining the temperature thereof at 300° C., followed by supplying the mixture liquid via a line B70 to a thin-film evaporator B702.

The supplied mixture liquid was developed in a thin-film state on a heated evaporation surface B701 heated at 280° C. and at 6.7 MPa. The gas phase component was cooled in the condenser B704 at 50° C., and the condensed liquid was discharged through a line B73.

Step (7-2): Step for discharging the reaction liquid to the outside of the reactor.

The reaction liquid in the step (7-1) was collected in a collection part B703 formed in the bottom part of the thin-film evaporator, followed by discharging the reaction liquid via a line B72.

It was confirmed as a result of a gas chromatography analysis of the discharged reaction liquid that 1,5-pentamethylenediamine was contained.

Step (7-3): Step for separating a compound (III)

The discharged reaction liquid was distilled under reduced pressure to collect a crude 1,5-pentamethylenediamine.

Step (7-4): Step for purifying the compound (III)

The crude 1,5-pentamethylenediamine collected in the step (7-3) was subjected to distillation purification. The purity of the collected 1,5-pentamethylenediamine was 99% by mass or more (including a margin of error in the gas chromatography analysis). The amount of metallic atoms was less than 1000 ppm, and that of halogen atoms was less than 1000 ppm, relative to the total mass of 1,5-pentamethylenediamine.

Examples 8 to 52

A step (1) in which a liquid phase component containing a high-boiling point compound formed as a by-product in the preparation of a compound (I) and an active hydrogen-containing compound were reacted in a reactor; a step (2) in which a gas phase component in the reactor was cooled to obtain a condensed liquid, and then the condensed liquid was returned to the inside of the reactor; a step in which a gas phase components that were not condensed was discharged to the outside of the reactor; step (4) in which the liquid phase component in the reactor was discharged to the outside of the reactor; a step (5) in which a compound (III) was separated; a step (6) in which the compound (III) was purified; a step (7) in which a compound (V) was separated; and a step in which a compound (V) was generated, were conducted by combining the methods described in Examples 1 to 7. Results thereof are indicated in tables. An organic primary amine used as an active hydrogen compound was not included in a yield of an organic primary amine.

In Examples 8 to 10, 14 to 17, 34, 39 and 43 in which the thermal decomposition of carbamate was conducted by the same method as that of the "thermal decomposition of carbamate" in Example 2, compounds shown in the following table were used instead of dibenzyl ether.

TABLE 1

| Examples | Compound used instead of dibenzyl ether |
|---|---|
| Example 8 | n-Pentadecane |
| Example 9 | Benzyl butyl phthalate |
| Example 10 | Benzyl toluene |
| Example 14 | Diethyl phthalate |
| Example 15 | Bis(2-methoxyethyl) phthalate |
| Example 16 | Tri(2-ethylhexyl) trimellitate |
| Example 17 | Chlorododecane |
| Example 34 | Fluorene |
| Example 39 | Benzyl toluene |
| Example 43 | Tri(2-ethylhexyl) trimellitate |

TABLE 2

Figure 12:
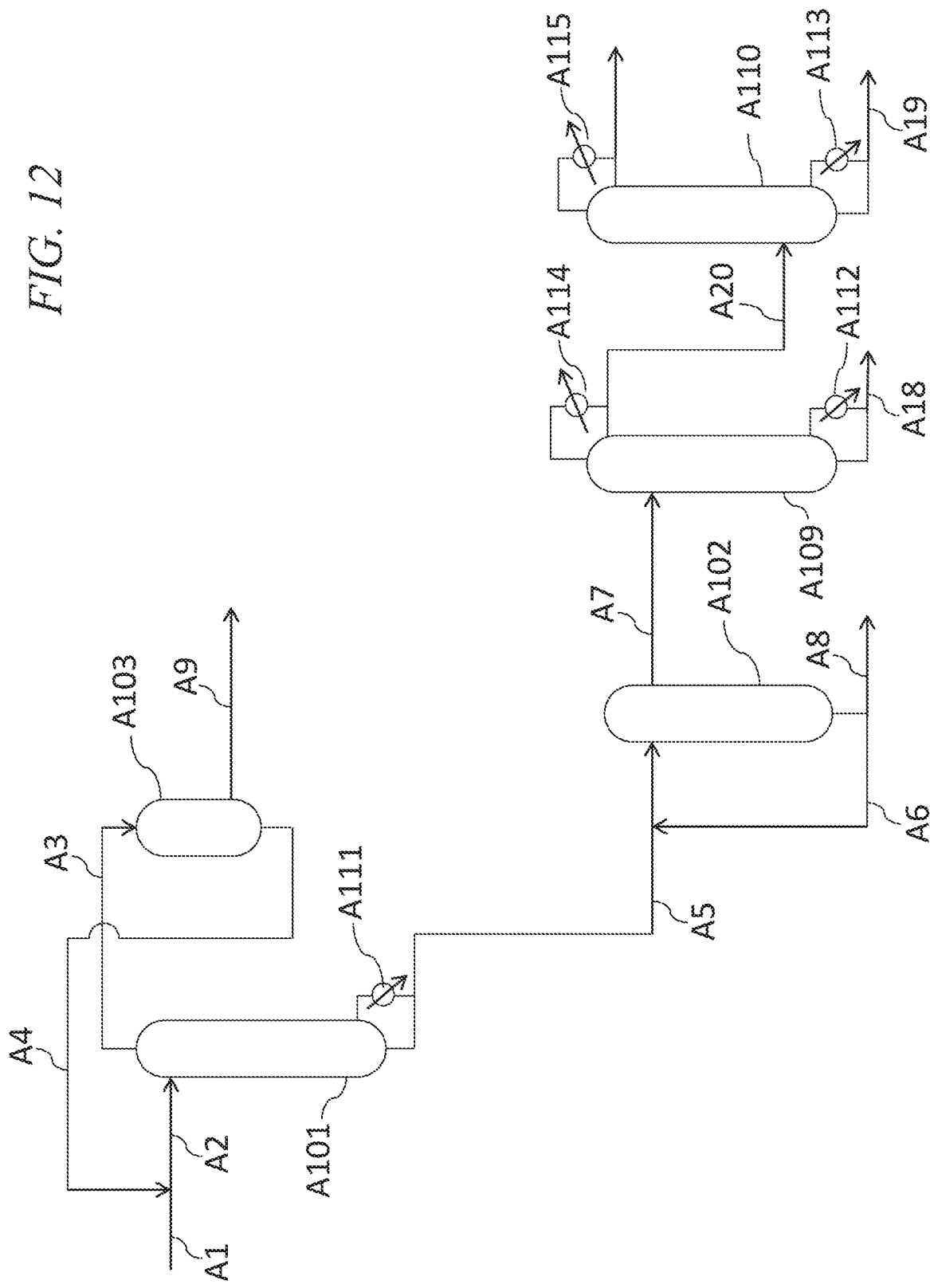
FIG. 12 is an explanation drawing illustrating a carbamate production facility used in the step (1-A) in Example 1.

| | Preparation of carbamate | | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hour · m) | Linear velocity of gas phase component (m/second) |
| Ex. 1 | 2,4-Diamino toluene | Urea | 4-(1,1,3,3-Tetra-methyl butyl) phenol | FIG. 12 | FIG. 12 | 50 | 8.0 |
| Ex. 2 | 1-Amino-3-amino methyl-3,5,5-trimethyl cyclohexane | Urea | 1-Butanol | FIG. 13 | FIG. 15 | — | — |
| Ex. 3 | 4,4'-Dicyclo-hexyl methane diamine | Diphenyl carbonate | Phenol | FIG. 16 | FIG. 15 | — | — |
| Ex. 4 | 1,6-Hexa-methylene diamine | Diphenyl carbonate | Phenol 4-(α,α-Dimethyl benzyl) phenol | FIG. 16 FIG. 17 | FIG. 12 | 50 | 8.0 |
| Ex. 5 | 2,4-Diamino toluene | Urea | 4-(1,1,3,3-Tetra-methyl butyl) phenol | FIG. 18 + FIG. 12 | FIG. 12 | 50 | 8.0 |
| Ex. 6 | 1,5-Penta-methylene diamine | — | — | Phosgene method | — | — | — |
| Ex. 7 | 1,5-Penta-methylene diamine | — | — | Phosgene method (identical to Example 6) | — | — | — |

TABLE 3

| | Preparation of carbamate | | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 8 | 2,4-Diamino toluene | Diphenyl carbonate | Ethanol | FIG. 16 (Method identical to preparation of carbamate in Example 3) | FIG. 15 (Method identical to thermal decomposition of carbamate in Example 2) | 64 | 5.3 |
| Ex. 9 | 1,5-Penta-methylene diamine | Diphenyl carbonate | Phenol | FIG. 16 (Method identical to preparation of carbamate in Example 3) | FIG. 15 (Method identical to thermal decomposition of carbamate in Example 2) | 32 | 2.5 |
| Ex. 10 | 1,6-Hexa-methylene diamine | Diphenyl carbonate | Phenol | FIG. 16 (Method identical to preparation of carbamate in Example 3) | FIG. 15 (Method identical to thermal decomposition of carbamate in Example 2) | 79 | 5.5 |

TABLE 3-continued

| | | Preparation of carbamate | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 11 | 1-Amino-3-amino methyl-3,5,5-trimethyl cyclohexane | Diphenyl carbonate | 1-Butanol | FIG. 16 (Method identical to preparation of carbamate in Example 3) | FIG. 15 (Method identical to thermal decomposition of carbamate in Example 2) | 59 | 2.2 |
| Ex. 12 | Xylylene diamine | Diphenyl carbonate | Phenol | FIG. 16 (Method identical to preparation of carbamate in Example 3) | FIG. 15 (Method identical to thermal decomposition of carbamate in Example 2) | 43 | 6.4 |

TABLE 4

| | | Preparation of carbamate | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 13 | Hydrogenated xylene diamine | Diphenyl carbonate | Phenol | FIG. 16 (Method identical to preparation of carbamate in Example 3) | FIG. 15 (Method identical to thermal decomposition of carbamate in Example 2) | 14 | 9.5 |
| Ex. 14 | 1,3-Bis(2-amino-2-propyl) benzene | Dibutyl carbonate | 1-Butanol | FIG. 16 (Method identical to preparation of carbamate in Example 3) | FIG. 15 (Method identical to thermal decomposition of carbamate in Example 2) | 69 | 7.3 |
| Ex. 15 | 1,3-Bis(2-amino-2-propyl) cyclohexane | Diphenyl carbonate | Phenol | FIG. 16 (Method identical to preparation of carbamate in Example 3) | FIG. 15 (Method identical to thermal decomposition of carbamate in Example 2) | 77 | 1.4 |
| Ex. 16 | 4-Amino methyl-1,8-octane diamine | Diphenyl carbonate | Phenol | FIG. 16 (Method identical to preparation of carbamate in Example 3) | FIG. 15 (Method identical to thermal decomposition of carbamate in Example 2) | 76 | 4.6 |
| Ex. 17 | 2,4-Diamino toluene | Urea | 4-Ethoxy Phenol | FIG. 13 (Method identical to preparation of carbamate and preliminary condensation in Example 2) | FIG. 15 (Method identical to thermal decomposition of carbamate in Example 2) | 55 | 7.2 |

TABLE 4-continued

| | Preparation of carbamate | | | | Thermal decomposition of carbamate | | |
|---|---|---|---|---|---|---|---|
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 18 | 1,5-Penta-methylene diamine | Urea | 4-(1,1,3,3-Tetra-methyl butyl) phenol | FIG. 12 (Method identical to preparation of carbamate in Example 1) | FIG. 12 (Method identical to thermal decomposition of carbamate in Example 1) | 41 | 2.4 |

TABLE 5

| | Preparation of carbamate | | | | Thermal decomposition of carbamate | | |
|---|---|---|---|---|---|---|---|
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 19 | 1,6-Hexa-methylene diamine | Urea | 1-Butanol | FIG. 13 (Method identical to preparation of carbamate and preliminary condensation in Example 2) | FIG. 15 (Method identical to thermal decomposition of carbamate in Example 2) | 75 | 1.7 |
| Ex. 20 | 1-Amino-3-amino methyl-3,5,5-trimethyl cyclohexane | Urea | Phenol | FIG. 13 (Method identical to preparation of carbamate and preliminary condensation in Example 2) | FIG. 15 (Method identical to thermal decomposition of carbamate in Example 2) | 67 | 4.8 |
| Ex. 21 | Xylylene diamine | Urea | 4-Phenyl phenol | FIG. 12 (Method identical to preparation of carbamate in Example 1) | FIG. 12 (Method identical to thermal decomposition of carbamate in Example 1) | 87 | 3.4 |
| Ex. 22 | Hydro-genated xylene diamine | Urea | p-Dodecyl phenol | FIG. 12 (Method identical to preparation of carbamate in Example 1) | FIG. 12 (Method identical to thermal decomposition of carbamate in Example 1) | 229 | 5.3 |
| Ex. 23 | 1,3-Bis(2-amino-2-propyl) benzene | Urea | Bisphenol A | FIG. 12 (Method identical to preparation of carbamate in Example 1) | FIG. 12 (Method identical to thermal decomposition of carbamate in Example 1) | 209 | 5.7 |

TABLE 6

| | Preparation of carbamate | | | | Thermal decomposition of carbamate | | |
| --- | --- | --- | --- | --- | --- | --- | --- |
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 24 | 1,3-Bis(2-amino-2-propyl)cyclohexane | Urea | 2,4-di-(α,α-dimethyl benzyl) phenol | FIG. 12 (Method identical to preparation of carbamate in Example 1) | FIG. 12 (Method identical to thermal decomposition of carbamate in Example 1) | 230 | 5.7 |
| Ex. 25 | 4-Aminomethyl-1,8-octane diamine | Urea | Styrenated phenol (tri-substituent) | FIG. 12 (Method identical to preparation of carbamate in Example 1) | FIG. 12 (Method identical to thermal decomposition of carbamate in Example 1) | 239 | 9.5 |
| Ex. 26 | 2,4-Diamino toluene | Urea | Hydroquinone | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 277 | 1.7 |
| Ex. 27 | 1,5-Pentamethylene diamine | Urea | ρ-Heptyl phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 182 | 3.1 |
| Ex. 28 | 1,6-Hexamethylene diamine | Urea | 4-Nonyl phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 85 | 3.8 |

TABLE 7

| | | Preparation of carbamate | | | Thermal decomposition of carbamate | | |
| --- | --- | --- | --- | --- | --- | --- | --- |
| | | | | | | Flow rate per wetted perimeter (kg/hr · m) | Linear velocity of gas phase component (m/s) |
| | Organic primary amine | Carbonic acid derivative | Hydroxy compound | Method, device FIG. | Method, device FIG. | | |
| Ex. 29 | 1-Amino-3-amino methyl-3,5,5-trimethyl cyclohexane | Urea | Tribenzyl phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 49 | 4 |
| Ex. 30 | Xylylene diamine | Urea | 4-Phenyl phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 106 | 1.5 |
| Ex. 31 | Hydrogenated xylene diamine | Urea | Styrenated phenol (tri-substituent) | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 13 | 1.6 |
| Ex. 32 | 1,3-Bis(2-amino-2-propyl) benzene | Urea | Bisphenol A | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 167 | 7.2 |

TABLE 8

| | Preparation of carbamate | | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 33 | 1,3-Bis(2-amino-2-propyl)cyclohexane | Urea | Tribenzyl phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 33 | 8.7 |
| Ex. 34 | 4-Amino methyl-1,8-octane diamine | Urea | 2-tert-amino phenol | FIG. 18 (Method identical to preparation of ureido group-containing compound in Example 5) + FIG. 12 (Method identical to preparation of carbamate in Example 5) | FIG. 15 (Method identical to thermal decomposition of carbamate in Example 2) | 192 | 5.2 |
| Ex. 35 | 2,4-Diamino toluene | Urea | Isobutanol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 289 | 6.5 |
| | | | 4-(1,1,3,3-Tetra-methyl butyl) phenol | FIG. 17 (Method identical to ester exchange reaction in Example 4) | | | |

TABLE 9

| | Preparation of carbamate | | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 36 | 1,5-Pentamethylene diamine | Urea | Phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 124 | 7.4 |
| | | | 2,4-Di-tert-amylphenol | FIG. 17 (Method identical to ester exchange reaction in Example 4) | | | |
| Ex. 37 | 1,6-Hexamethylene diamine | Urea | Phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 50 | 8.0 |
| | | | 4-(α,α Dimethyl benzyl) phenol | FIG. 17 (Method identical to ester exchange reaction in Example 4) | | | |
| Ex. 38 | 1-Amino-3-amino methyl-3,5,5-trimethyl cyclohexane | Urea | 2,6-Xylenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 128 | 7.0 |
| | | | 4-Phenyl phenol | FIG. 17 (Method identical to ester exchange reaction in Example 4) | | | |

TABLE 10

| | Preparation of carbamate | | | | Thermal decomposition of carbamate | | |
|---|---|---|---|---|---|---|---|
| | Organic primary amine | Carbonic acid derivative | Hydroxy compound | Method, device FIG. | Method, device FIG. | Flow rate per wetted perimeter (kg/hr · m) | Linear velocity of gas phase component (m/s) |
| Ex. 39 | Xylylene diamine | Urea | Isoamyl alcohol | FIG. 18 (Method identical to preparation of ureido group-containing compound in Example 5) + FIG. 12 (Method identical to preparation of carbamate in Example 5) | FIG. 15 (Method identical to thermal decomposition of carbamate in Example 2) | 13 | 4.0 |
| | | | Phenol | FIG. 17 (Method identical to ester exchange reaction in Example 4) | | | |
| Ex. 40 | Hydrogenated xylene diamine | Urea | Phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 294 | 7.2 |
| | | | Bisphenol A | FIG. 17 (Method identical to ester exchange reaction in Example 4) | | | |
| Ex. 41 | 1,3-Bis(2-amino-2-propyl)benzene | Urea | 2-Ethyl hexanol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 53 | 1.8 |
| | | | 2,4-di-(α,α-dimethyl benzyl) phenol | FIG. 17 (Method identical to ester exchange reaction in Example 4) | | | |

TABLE 11

| | Preparation of carbamate | | | | Thermal decomposition of carbamate | | |
| --- | --- | --- | --- | --- | --- | --- | --- |
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 42 | 1,3-Bis(2-amino-2-propyl)cyclohexane | Urea | 4-Ethyl phenol | FIG. 18 (Method identical to preparation of ureido group-containing compound in Example 5) + FIG. 12 (Method identical to preparation of carbamate in Example 5) | FIG. 12 (Method identical to thermal decomposition of carbamate in Example 1) | 264 | 2.9 |
| | | | 4-Phenyl pehnol | FIG. 17 (Method identical to ester exchange reaction in Example 4) | | | |
| Ex. 43 | 4-Amino methyl-1,8-octane diamine | Urea | 1-Butanol | FIG. 18 (Method identical to preparation of ureido group-containing compound in Example 5) + FIG. 12 (Method identical to preparation of carbamate in Example 5) | FIG. 15 (Method identical to thermal decomposition of carbamate in Example 2) | 224 | 5.0 |
| | | | Phenol | FIG. 17 (Method identical to ester exchange reaction in Example 4) | | | |
| Ex. 44 | 2,4-Diamino toluene | Dibutyl carbonate | 1-Butanol | FIG. 16 (Method identical to preparation of carbamate in Example 3) | FIG. 12 (Method identical to thermal decomposition of carbamate in Example 1) | 180 | 4.1 |
| | | | 2,6-Diisopropyl phenol | FIG. 17 (Method identical to ester exchange reaction in Example 4) | | | |

TABLE 12

| | Preparation of carbamate | | | | Thermal decomposition of carbamate | | |
|---|---|---|---|---|---|---|---|
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 45 | 1,5-Penta-methylene diamine | Diphenyl carbonate | Phenol | FIG. 16 (Method identical to preparation of carbamate in Example 3) | FIG. 12 (Method identical to thermal decomposition of carbamate in Example 1) | 124 | 7.4 |
| | | | 4-Phenyl phenol | FIG. 17 (Method identical to ester exchange reaction in Example 4) | | | |
| Ex. 46 | 1,6-Hexa-methylene diamine | Dibutyl carbonate | 1-Butanol | FIG. 16 (Method identical to preparation of carbamate in Example 3) | FIG. 12 (Method identical to thermal decomposition of carbamate in Example 1) | 114 | 5.3 |
| | | | 2,4-di-(α,α-dimethyl benzyl) phenol | FIG. 17 (Method identical to ester exchange reaction in Example 4) | | | |
| Ex. 47 | 1-Amino-3-amino methyl-3,5,5-trimethyl cyclohexane | Diphenyl carbonate | Phenol | FIG. 16 (Method identical to preparation of carbamate in Example 3) | FIG. 12 (Method identical to thermal decomposition of carbamate in Example 1) | 21 | 5.9 |
| | | | Styrenated phenol (tri-substituent) | FIG. 17 (Method identical to ester exchange reaction in Example 4) | | | |

TABLE 13

| | Preparation of carbamate | | | | Thermal decomposition of carbamate | | |
|---|---|---|---|---|---|---|---|
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 48 | Xylylene diamine | Diphenyl carbonate | Phenol | FIG. 16 (Method identical to preparation of carbamate in Example 3) | FIG. 12 (Method identical to thermal decomposition of carbamate in Example 1) | 201 | 5.4 |
| | | | 4-Nonyl phenol | FIG. 17 (Method identical to ester exchange reaction in Example 4) | | | |

TABLE 13-continued

| | | Preparation of carbamate | | | Thermal decomposition of carbamate | | |
| --- | --- | --- | --- | --- | --- | --- | --- |
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 49 | Hydrogenated xylene diamine | Diphenyl carbonate | Phenol | FIG. 16 (Method identical to preparation of carbamate in Example 3) | FIG. 12 (Method identical to thermal decomposition of carbamate in Example 1) | 65 | 8.4 |
| | | | 2,4-Di-tert-amylphenol | FIG. 17 (Method identical to ester exchange reaction in Example 4) | | | |
| Ex. 50 | 1,3-Bis(2-amino-2-propyl) benzene | Diphenyl carbonate | Phenol | FIG. 16 (Method identical to preparation of carbamate in Example 3) | FIG. 12 (Method identical to thermal decomposition of carbamate in Example 1) | 26 | 6.4 |
| | | | Bisphenol A | FIG. 17 (Method identical to ester exchange reaction in Example 4) | | | |

TABLE 14

| | | Preparation of carbamate | | | Thermal decomposition of carbamate | | |
| --- | --- | --- | --- | --- | --- | --- | --- |
| | | | | | | Flow rate | Linear velocity |
| | Organic primary amine | Carbonic acid derivative | Hydroxy compound | Method, device FIG. | Method, device FIG. | per wetted perimeter (kg/hr · m) | of gas phase component (m/s) |
| Ex. 51 | 1,3-Bis(2-amino-2-propyl) cyclohexane | Diphenyl carbonate | Phenol | FIG. 16 (Method identical to preparation of carbamate in Example 3) | FIG. 12 (Method identical to thermal decomposition of carbamate in Example 1) | 31 | 4.6 |
| | | | 4-Dodecyl phenol | FIG. 17 (Method identical to ester exchange reaction in Example 4) | | | |
| Ex. 52 | 4-Amino methyl-1,8-octane diamine | Diphenyl carbonate | Phenol | FIG. 16 (Method identical to preparation of carbamate in Example 3) | FIG. 12 (Method identical to thermal decomposition of carbamate in Example 1) | 225 | 3.4 |
| | | | Styrenated phenol (tri-substituent) | FIG. 17 (Method identical to ester exchange reaction in Example 4) | | | |

TABLE 15

| | Transfer temperature to step (1) (° C.) | Composition containing high-boiling point compound | | | | | | | |
|---|---|---|---|---|---|---|---|---|---|
| | | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa · s) | Used amount (kg) |
| Ex. 1 | 180 | 0.90 | 0.13 | 0.12 | 0.22 | 2.77 | 4-(1,1,3,3-tetra-methyl butyl) phenol | 70 | 50 |
| Ex. 2 | 180 | 2.56 | 0.14 | 0.10 | 0.00 | — | — | 40 | 50 |
| Ex. 3 | 180 | 2.67 | 0.17 | 0.62 | 0.02 | — | — | 50 | 50 |
| Ex. 4 | 180 | 2.05 | 0.19 | 0.48 | 0.02 | 1.25 | 4-(α,α-di-methyl benzyl) phenol | 60 | 50 |
| Ex. 5 | 180 | 1.33 | 0.10 | 0.10 | 0.16 | 2.04 | 4-(1,1,3,3-tetra-methyl butyl) phenol | 82 | 50 |
| Ex. 6 | 300 | — | Unclear since the analyzed sample contained (an) unsoluble component(s). | | | — | — | 150 | 50 |
| Ex. 7 | 300 | — | Unclear since the analyzed sample contained (an) unsoluble component(s). | | | — | — | 150 | 50 |

TABLE 16

| | Transfer temperature to step (1) (° C.) | Composition containing high-boiling point compound | | | | | | | |
|---|---|---|---|---|---|---|---|---|---|
| | | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa · s) | Used amount (kg) |
| Ex. 8 | 200 | 2.60 | 0.49 | 0.41 | 0.06 | 7.83 | Ethanol | 150 | 50 |
| Ex. 9 | 230 | 2.78 | 0.99 | 0.21 | 0.03 | 3.72 | Phenol | 60 | 50 |
| Ex. 10 | 160 | 2.62 | 0.02 | 0.79 | 0.03 | 4.26 | Phenol | 100 | 50 |
| Ex. 11 | 340 | 2.44 | 0.62 | 0.20 | 0.14 | 4.19 | 1-Butanol | 140 | 50 |
| Ex. 12 | 220 | 3.63 | 0.18 | 0.52 | 0.05 | 2.02 | Phenol | 80 | 50 |

TABLE 17

| | Transfer temperature to step (1) (° C.) | Composition containing high-boiling point compound | | | | | | | |
|---|---|---|---|---|---|---|---|---|---|
| | | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa · s) | Used amount (kg) |
| Ex. 13 | 220 | 3.27 | 0.32 | 0.52 | 0.08 | 2.02 | Phenol | 100 | 50 |
| Ex. 14 | 150 | 2.20 | 0.69 | 0.19 | 0.10 | 4.32 | 1-Butanol | 80 | 50 |

TABLE 17-continued

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 15 | 260 | 2.18 | 0.65 | 0.23 | 0.14 | 2.66 | Phenol | 50 | 50 |
| Ex. 16 | 210 | 2.47 | 0.20 | 0.16 | 0.04 | 2.55 | Phenol | 100 | 50 |
| Ex. 17 | 220 | 1.34 | 0.50 | 0.06 | 0.10 | 3.55 | 4-Ethoxy Phenol | 100 | 50 |
| Ex. 18 | 160 | 2.08 | 0.01 | 0.29 | 0.05 | 1.70 | 4-(1,1,3,3-tetra-methyl butyl) phenol | 70 | 50 |

TABLE 18

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 19 | 240 | 3.09 | 0.42 | 0.45 | 0.06 | 4.86 | 1-Butanol | 60 | 50 |
| Ex. 20 | 300 | 2.60 | 0.41 | 0.48 | 0.02 | 2.55 | Phenol | 60 | 50 |
| Ex. 21 | 260 | 1.63 | 0.24 | 0.23 | 0.08 | 2.59 | 4-Phenyl phenol | 80 | 50 |
| Ex. 22 | 240 | 1.72 | 0.25 | 0.22 | 0.07 | 0.91 | ρ-Dodecyl phenol | 90 | 50 |
| Ex. 23 | 300 | 1.45 | 0.09 | 0.04 | 0.04 | 1.88 | Bis-phenol A | 50 | 50 |

TABLE 19

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 24 | 260 | 1.00 | 0.08 | 0.23 | 0.06 | 1.24 | 2,4-di-(α,α-di-methyl benzyl) phenol | 60 | 50 |
| Ex. 25 | 330 | 0.77 | 0.28 | 0.06 | 0.01 | 0.86 | Styrenated phenol (tri-substituent) | 100 | 50 |
| Ex. 26 | 250 | 2.10 | 0.12 | 0.17 | 0.11 | 3.91 | Hydro-quinone | 90 | 50 |

TABLE 19-continued

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 27 | 270 | 2.51 | 0.55 | 0.02 | 0.04 | 1.14 | p-Heptyl phenol | 80 | 50 |
| Ex. 28 | 340 | 1.04 | 0.24 | 0.02 | 0.10 | 2.63 | 4-Nonyl phenol | 70 | 50 |

TABLE 20

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 29 | 230 | 1.24 | 0.11 | 0.07 | 0.02 | 0.96 | Tri-benzyl phenol | 50 | 50 |
| Ex. 30 | 210 | 2.52 | 0.29 | 0.06 | 0.09 | 1.29 | 4-Phenyl phenol | 90 | 50 |
| Ex. 31 | 330 | 1.34 | 0.19 | 0.17 | 0.03 | 0.57 | Styrenated phenol (tri-substituent) | 60 | 50 |
| Ex. 32 | 280 | 1.36 | 0.29 | 0.08 | 0.04 | 1.75 | Bis-phenol A | 90 | 50 |
| Ex. 33 | 260 | 1.07 | 0.34 | 0.06 | 0.01 | 1.02 | Tri-benzyl phenol | 60 | 50 |
| Ex. 34 | 210 | 0.94 | 0.20 | 0.08 | 0.05 | 3.35 | 2-tert-amyl phenol | 60 | 50 |

TABLE 21

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 35 | 260 | 1.16 | 0.21 | 0.17 | 0.03 | 2.52 | 4-(1,1,3,3-Tetra-methyl butyl) phenol | 70 | 50 |
| Ex. 36 | 350 | 1.89 | 0.44 | 0.20 | 0.02 | 1.32 | 2,4-Di-tert-amyl phenol | 50 | 50 |
| Ex. 37 | 200 | 1.86 | 0.13 | 0.34 | 0.03 | 1.70 | 4-(α,α-Di-methyl benzyl) phenol | 100 | 50 |

TABLE 21-continued

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 38 | 290 | 1.39 | 0.14 | 0.06 | 0.02 | 3.23 | 4-Phenyl phenol | 90 | 50 |
| Ex. 39 | 160 | 2.01 | 0.91 | 0.01 | 0.16 | 4.15 | Phenol | 70 | 50 |
| Ex. 40 | 300 | 2.03 | 0.41 | 0.03 | 0.06 | 0.96 | Bisphenol A | 50 | 50 |

TABLE 22

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 41 | 190 | 1.40 | 0.29 | 0.15 | 0.01 | 0.76 | 2,4-Di-(α,α-dimethyl benzyl) phenol | 50 | 50 |
| Ex. 42 | 300 | 1.70 | 0.11 | 0.21 | 0.07 | 2.17 | 4-Phenyl phenol | 100 | 50 |
| Ex. 43 | 180 | 1.35 | 0.01 | 0.40 | 0.02 | 6.06 | Phenol | 60 | 50 |
| Ex. 44 | 210 | 1.47 | 0.25 | 0.09 | 0.09 | 2.52 | 2,6-Diisopropyl phenol | 60 | 50 |
| Ex. 45 | 220 | 0.81 | 0.26 | 0.06 | 0.12 | 4.05 | 4-Phenyl phenol | 80 | 50 |
| Ex. 46 | 310 | 1.64 | 0.03 | 0.13 | 0.02 | 0.85 | 2,4-Di-(α,α-dimethyl benzyl) phenol | 90 | 50 |

TABLE 23

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 47 | 190 | 1.37 | 0.19 | 0.05 | 0.06 | 0.44 | Styrenated phenol (trisubstituent) | 50 | 50 |
| Ex. 48 | 320 | 1.97 | 0.05 | 0.35 | 0.02 | 1.27 | 4-Nonyl phenol | 50 | 50 |
| Ex. 49 | 340 | 2.19 | 0.37 | 0.11 | 0.03 | 0.68 | 2,4-Di-tert-amyl phenol | 60 | 50 |

TABLE 23-continued

| | | Composition containing high-boiling point compound | | | | | | |
|---|---|---|---|---|---|---|---|---|
| | Transfer temperature to step (1) (° C.) | Carbamate bond (mol/kg) | Total of groups (II-1) and (II-2) (mol/kg) | Total of allophanate bond and nurate bond (mol/kg) | Fries rearrangement terminal (mol/kg) | Hydroxy compound (mol/kg) | Hydroxy compound | Viscosity at 150° C. (mPa·s) | Used amount (kg) |
| Ex. 50 | 320 | 0.89 | 0.17 | 0.09 | 0.09 | 2.50 | Bis-phenol A | 60 | 50 |
| Ex. 51 | 180 | 0.67 | 0.17 | 0.08 | 0.05 | 2.44 | 4-Dodecyl phenol | 80 | 50 |
| Ex. 52 | 160 | 0.73 | 0.18 | 0.06 | 0.03 | 0.91 | Styrenated phenol (tri-substituent) | 80 | 50 |

TABLE 24

| | | | Steps (1)-(4) | | | Steps (5)-(6) | Steps (7)-(8) |
|---|---|---|---|---|---|---|---|
| | Device FIG. | Active hydrogen compound | Used amount of active hydrogen compound (kg) | Temperature (° C.) | Pressure (MPa) | Device• Method | Device• Method |
| Ex. 1 | FIG. 1 | Water | 100 | 280 | 6.5 | Distillation column | Distillation column |
| Ex. 2 | FIG. 2 | Water Ethanol | 100 16 | 250 | 4.3 | Distillation column | — |
| Ex. 3 | FIG. 3 | Water Ethanol | 100 50 | 250 | 4.9 | Distillation column | Distillation column |
| Ex. 4 | FIG. 4 | Water | 100 | 280 | 6.7 | Distillation column | Distillation column |
| Ex. 5 | FIG. 5 | Water | 100 | 280 | 6.7 | Distillation column | Distillation column |
| Ex. 6 | FIG. 6 | Water Ethanol | 50 30 | 280 | 6.7 | Distillation column | — |
| Ex. 7 | FIG. 7 | Water 1,5-Penta-methylene diamine | 50 25 | 280 | 6.7 | Distillation column | — |
| Ex. 8 | FIG. 3 | Water | 50 | 200 | 1.5 | Distillation column | Distillation column |

TABLE 25

| | | | Steps (1)-(4) | | | Steps (5)-(6) | Steps (7)-(8) |
|---|---|---|---|---|---|---|---|
| | Device FIG. | Active hydrogen compound | Used amount of active hydrogen compound (kg) | Temperature (° C.) | Pressure (MPa) | Device• Method | Device• Method |
| Ex. 9 | FIG. 2 | Water 1,5-Penta-methylene diamine | 50 20 | 220 | 2.4 | Distillation column | Distillation column |
| Ex. 10 | FIG. 7 | Water 1,6-Hexa-methylene diamine | 50 50 | 250 | 4 | Distillation column | Distillation column |
| Ex. 11 | FIG. 4 | Water | 50 | 280 | 6.5 | Distillation column | Distillation column |
| Ex. 12 | FIG. 5 | Water | 40 | 250 | 4 | Distillation column | Distillation column |
| Ex. 13 | FIG. 6 | Water | 60 | 190 | 1.3 | Distillation column | Distillation column |
| Ex. 14 | FIG. 1 | Water | 50 | 270 | 5.8 | Distillation column | Distillation column |

TABLE 25-continued

| | Device FIG. | Active hydrogen compound | Steps (1)-(4) Used amount of active hydrogen compound (kg) | Temperature (° C.) | Pressure (MPa) | Steps (5)-(6) Device•Method | Steps (7)-(8) Device•Method |
|---|---|---|---|---|---|---|---|
| Ex. 15 | FIG. 1 | Water | 60 | 220 | 2.5 | Distillation column | Distillation column |
| Ex. 16 | FIG. 2 | Water 4-Aminomethyl-1,8-octane diamine | 60 30 | 280 | 6.9 | Distillation column | Distillation column |

TABLE 26

| | Device FIG. | Active hydrogen compound | Steps (1)-(4) Used amount of active hydrogen compound (kg) | Temperature (° C.) | Pressure (MPa) | Steps (5)-(6) Device•Method | Steps (7)-(8) Device•Method |
|---|---|---|---|---|---|---|---|
| Ex. 17 | FIG. 5 | Water | 50 | 190 | 1.4 | Distillation column | Distillation column |
| Ex. 18 | FIG. 4 | Water | 50 | 230 | 2.8 | Distillation column | Distillation column |
| Ex. 19 | FIG. 5 | Water | 50 | 190 | 1.3 | Distillation column | Distillation column |
| Ex. 20 | FIG. 7 | Water 1-Amino-3-aminomethyl-3,5,5-trimethyl cyclohexane | 50 30 | 210 | 1.6 | Distillation column | Distillation column |
| Ex. 21 | FIG. 6 | Water | 50 | 220 | 1.7 | Distillation column | Distillation column |
| Ex. 22 | FIG. 1 | Water | 50 | 270 | 5.9 | Distillation column | Distillation column |
| Ex. 23 | FIG. 2 | Water | 60 | 270 | 5.9 | Distillation column | Distillation column |
| Ex. 24 | FIG. 3 | Water | 60 | 280 | 6.8 | Distillation column | Distillation column |

TABLE 27

| | Device FIG. | Active hydrogen compound | Steps (1)-(4) Used amount of active hydrogen compound (kg) | Temperature (° C.) | Pressure (MPa) | Steps (5)-(6) Device•Method | Steps (7)-(8) Device•Method |
|---|---|---|---|---|---|---|---|
| Ex. 25 | FIG. 4 | Water 4-Aminomethyl-1,8-octane diamine | 60 20 | 200 | 1.4 | Distillation column | Distillation column |
| Ex. 26 | FIG. 5 | Water | 50 | 270 | 5.8 | Distillation column | Distillation column |
| Ex. 27 | FIG. 6 | Water 1,5-Pentamethylene diamine | 50 30 | 220 | 1.7 | Distillation column | Distillation column |
| Ex. 28 | FIG. 7 | Water 1,6-Hexamethylene diamine | 50 30 | 220 | 1.7 | Distillation column | Distillation column |

TABLE 27-continued

| | Device FIG. | Active hydrogen compound | Used amount of active hydrogen compound (kg) | Temperature (° C.) | Pressure (MPa) | Steps (5)-(6) Device• Method | Steps (7)-(8) Device• Method |
|---|---|---|---|---|---|---|---|
| Ex. 29 | FIG. 1 | Water 1-Amino-3-amino methyl-3,5,5-trimethyl cyclohexane | 50 20 | 270 | 5.8 | Distillation column | Distillation column |
| Ex. 30 | FIG. 2 | Water | 50 | 190 | 1.3 | Distillation column | Distillation column |
| Ex. 31 | FIG. 3 | Water | 50 | 210 | 1.6 | Distillation column | Distillation column |

TABLE 28

| | Device FIG. | Active hydrogen compound | Used amount of active hydrogen compound (kg) | Temperature (° C.) | Pressure (MPa) | Steps (5)-(6) Device• Method | Steps (7)-(8) Device• Method |
|---|---|---|---|---|---|---|---|
| Ex. 32 | FIG. 4 | Water | 50 | 210 | 1.6 | Distillation column | Distillation column |
| Ex. 33 | FIG. 5 | Water | 50 | 190 | 1.3 | Distillation column | Distillation column |
| Ex. 34 | FIG. 7 | Water 4-Amino methyl-1,8-octane diamine | 50 20 | 200 | 1.4 | Distillation column | Distillation column |
| Ex. 35 | FIG. 6 | Water | 50 | 270 | 5.8 | Distillation column | Distillation column |
| Ex. 36 | FIG. 7 | Water 1,5-Penta-methylene diamine | 50 30 | 220 | 1.7 | Distillation column | Distillation column |
| Ex. 37 | FIG. 2 | Water 1,6-Hexa-methylene diamine | 50 30 | 260 | 5.9 | Distillation column | Distillation column |
| Ex. 38 | FIG. 3 | Water 1-Amino-3-amino methyl-3,5,5-trimethyl cyclohexane | 50 30 | 240 | 4.3 | Distillation column | Distillation column |

TABLE 29

| | Device FIG. | Active hydrogen compound | Used amount of active hydrogen compound (kg) | Temperature (° C.) | Pressure (MPa) | Steps (5)-(6) Device• Method | Steps (7)-(8) Device• Method |
|---|---|---|---|---|---|---|---|
| Ex. 39 | FIG. 4 | Water | 60 | 220 | 1.7 | Distillation column | Distillation column |
| Ex. 40 | FIG. 5 | Water | 80 | 240 | 4.3 | Distillation column | Distillation column |
| Ex. 41 | FIG. 6 | Water | 90 | 200 | 1.5 | Distillation column | Distillation column |

TABLE 29-continued

| | Device FIG. | Active hydrogen compound | Steps (1)-(4) Used amount of active hydrogen compound (kg) | Temperature (° C.) | Pressure (MPa) | Steps (5)-(6) Device•Method | Steps (7)-(8) Device•Method |
|---|---|---|---|---|---|---|---|
| Ex. 42 | FIG. 1 | Water | 50 | 280 | 5.9 | Distillation column | Distillation column |
| Ex. 43 | FIG. 1 | Water | 50 | 280 | 5.9 | Distillation column | Distillation column |
| Ex. 44 | FIG. 2 | Water | 50 | 240 | 4.3 | Distillation column | Distillation column |
| Ex. 45 | FIG. 3 | Water 1,5-Penta methylene diamine | 50 30 | 280 | 5.8 | Distillation column | Distillation column |

TABLE 30

| | Device FIG. | Active hydrogen compound | Steps (1)-(4) Used amount of active hydrogen compound (kg) | Temperature (° C.) | Pressure (MPa) | Steps (5)-(6) Device•Method | Steps (7)-(8) Device•Method |
|---|---|---|---|---|---|---|---|
| Ex. 46 | FIG. 4 | Water 1,6-Hexa methylene diamine | 50 30 | 250 | 4.6 | Distillation column | Distillation column |
| Ex. 47 | FIG. 7 | Water 1-Amino-3-amino methyl-3,5,5-trimethyl cyclohexane | 50 10 | 210 | 1.6 | Distillation column | Distillation column |
| Ex. 48 | FIG. 5 | Water | 50 | 280 | 5.8 | Distillation column | Distillation column |
| Ex. 49 | FIG. 6 | Water | 50 | 270 | 5.6 | Distillation column | Distillation column |
| Ex. 50 | FIG. 1 | Water | 50 | 230 | 4.1 | Distillation column | Distillation column |
| Ex. 51 | FIG. 2 | Water | 50 | 260 | 5.1 | Distillation column | Distillation column |
| Ex. 52 | FIG. 3 | Water | 50 | 260 | 5.1 | Distillation column | Distillation column |

TABLE 31

| | Collected product | Amount of collected product (kg) | Yield (%) | Amount of metallic component (ppm) | Amount of halogen atom (ppm) |
|---|---|---|---|---|---|
| Ex. 1 | 2,4-Diaminotoluene | 4.8 | 80 | Less than 1000 | Less than 1000 |
| | 4-(1,1,3,3-Tetramethylbutyl)phenol | 34.3 | 81 | 1000 | 1000 |
| Ex. 2 | 1-Amino-3-aminomethyl-3,5,5-trimethylcyclohexane | 12.1 | 90 | Less than 1000 | Less than 1000 |
| Ex. 3 | 4,4'-Dicyclohexylmethanediamine | 23.3 | 90 | Less than 1000 | Less than 1000 |
| Ex. 4 | 1,6-Hexamethylenediamine | 8.9 | 78 | Less than 1000 | Less than 1000 |
| | 4-(α,α-Dimethylbenzyl)phenol | 26.3 | 74 | 1000 | 1000 |
| Ex. 5 | 2,4-Diamino toluene | 6.8 | 73 | Less than 1000 | Less than 1000 |
| | 4-(1,1,3,3-Tetramethylbutyl)phenol | 29.6 | 78 | 1000 | 1000 |

TABLE 31-continued

| | Collected product | Amount of collected product (kg) | Yield (%) | Amount of metallic component (ppm) | Amount of halogen atom (ppm) |
|---|---|---|---|---|---|
| Ex. 6 | 1,5-Pentamethylenediamine | 36.7 | — | Less than 1000 | Less than 1000 |
| Ex. 7 | 1,5-Pentamethylenediamine | 32.1 | — | Less than 1000 | Less than 1000 |
| Ex. 8 | 2,4-Diaminotoluene | 15.5 | 73 | Less than 1000 | Less than 1000 |

TABLE 32

| | Collected product | Amount of collected product (kg) | Yield (%) | Amount of metallic component (ppm) | Amount of halogen atom (ppm) |
|---|---|---|---|---|---|
| Ex. 9 | 1,5-Pentamethylenediamine | 13.3 | 96 | Less than 1000 | Less than 1000 |
| Ex. 10 | 1,6-Hexamethylenediamine | 13.7 | 93 | Less than 1000 | Less than 1000 |
| Ex. 11 | 1-Amino-3-aminomethyl-3,5,5-trimethylcyclohexane | 16.3 | 83 | Less than 1000 | Less than 1000 |
| Ex. 12 | Xylylenediamine | 15.6 | 81 | Less than 1000 | Less than 1000 |
| Ex. 13 | Hydrogenated xylenediamine | 14.4 | 72 | Less than 1000 | Less than 1000 |
| Ex. 14 | 1,3-Bis(2-amino-2-propyl)benzene | 16.7 | 80 | Less than 1000 | Less than 1000 |
| Ex. 15 | 1,3-Bis(2-amino-2-propyl)cyclohexane | 16.1 | 73 | Less than 1000 | Less than 1000 |

TABLE 33

| | Collected product | Amount of collected product (kg) | Yield (%) | Amount of metallic component (ppm) | Amount of halogen atom (ppm) |
|---|---|---|---|---|---|
| Ex. 16 | 4-Aminomethyl-1,8-octane diamine | 13.7 | 92 | Less than 1000 | Less than 1000 |
| Ex. 17 | 2,4-Diaminotoluene | 8.7 | 74 | Less than 1000 | Less than 1000 |
| Ex. 18 | 1,5-Pentamethylene diamine 4-(1,1,3,3-Tetramethylbutyl)phenol | 6.5 28.4 | 82 71 | Less than 1000 | Less than 1000 |
| Ex. 19 | 1,6-Hexamethylene diamine | 11.5 | 73 | Less than 1000 | Less than 1000 |
| Ex. 20 | 1-Amino-3-aminomethyl-3,5,5-tri-methylcyclohexane | 17.9 | 85 | Less than 1000 | Less than 1000 |
| Ex. 21 | Xylylenediamine 4-Phenylphenol | 7.8 27.9 | 78 75 | Less than 1000 | Less than 1000 |
| Ex. 22 | Hydrogenated xylenediamine p-Dodecylphenol | 8.3 26.5 | 78 83 | Less than 1000 | Less than 1000 |

TABLE 34

| | Collected product | Amount of collected product (kg) | Yield (%) | Amount of metallic component (ppm) | Amount of halogen atom (ppm) |
|---|---|---|---|---|---|
| Ex. 23 | 1,3-Bis(2-amino-2-propyl)benzene Bisphenol A | 6.3 28.9 | 71 74 | Less than 1000 | Less than 1000 |
| Ex. 24 | 1,3-Bis(2-amino-2-propyl)cyclohexane 2,4-di-(α,α-dimethylbenzyl)phenol | 7.5 32.2 | 78 83 | Less than 1000 | Less than 1000 |
| Ex. 25 | 4-Aminomethyl-1,8-octane diamine Styrenated phenol (trisubstituent) | 6.0 32.4 | 92 97 | Less than 1000 | Less than 1000 |

TABLE 34-continued

| | Collected product | Amount of collected product (kg) | Yield (%) | Amount of metallic component (ppm) | Amount of halogen atom (ppm) |
|---|---|---|---|---|---|
| Ex. 26 | 2,4-Diaminotoluene | 10.7 | 81 | Less than 1000 | Less than 1000 |
| | Hydroquinone | 28.8 | 84 | 1000 | 1000 |
| Ex. 27 | 1,5-Pentamethylene diamine | 8.9 | 93 | Less than 1000 | Less than 1000 |
| | p-Heptylphenol | 32.6 | 91 | 1000 | 1000 |
| Ex. 28 | 1,6-Hexamethylene diamine | 3.9 | 76 | Less than 1000 | Less than 1000 |
| | 4-Nonylphenol | 30.3 | 71 | 1000 | 1000 |

TABLE 35

| | Collected product | Amount of collected product (kg) | Yield (%) | Amount of metallic component (ppm) | Amount of halogen atom (ppm) |
|---|---|---|---|---|---|
| Ex. 29 | 1-Amino-3-aminomethyl-3,5,5-trimethyl cyclohexane | 6.7 | 91 | Less than 1000 | Less than 1000 |
| | Tribenzyl phenol | 37.6 | 92 | 1000 | 1000 |
| Ex. 30 | Xylylene diamine | 9.1 | 77 | Less than 1000 | Less than 1000 |
| | 4-Phenyl phenol | 25.5 | 75 | 1000 | 1000 |
| Ex. 31 | Hydrogenated xylene diamine | 5.7 | 70 | Less than 1000 | Less than 1000 |
| | Styrenated phenol (trisubstituent) | 34.0 | 85 | 1000 | 1000 |
| Ex. 32 | 1,3-Bis(2-amino-2-propyl)benzene | 9.0 | 82 | Less than 1000 | Less than 1000 |
| | Bisphenol A | 28.1 | 77 | 1000 | 1000 |
| Ex. 33 | 1,3-Bis(2-amino-2-propyl)cyclohexane | 7.1 | 74 | Less than 1000 | Less than 1000 |
| | Tribenzyl phenol | 32.2 | 84 | 1000 | 1000 |
| Ex. 34 | 4-Aminomethyl-1,8-octane diamine | 6.9 | 94 | Less than 1000 | Less than 1000 |

TABLE 36

| | Collected product | Amount of collected product (kg) | Yield (%) | Amount of metallic component (ppm) | Amount of halogen atom (ppm) |
|---|---|---|---|---|---|
| Ex. 35 | 2,4-Diaminotoluene | 6.5 | 70 | Less than 1000 | Less than 1000 |
| | 4-(1,1,3,3-Tetramethylbutyl)phenol | 29.7 | 77 | 1000 | 1000 |
| Ex. 36 | 1,5-Pentamethylene diamine | 7.9 | 91 | Less than 1000 | Less than 1000 |
| | 2,4-Di-tert-amylphenol | 35.0 | 92 | 1000 | 1000 |
| Ex. 37 | 1,6-Hexamethylene diamine | 5.0 | 90 | Less than 1000 | Less than 1000 |
| | 4-(α,α-Dimethylbenzyl)phenol | 21.0 | 91 | 1000 | 1000 |
| Ex. 38 | 1-Amino-3-aminomethyl-3,5,5-trimethyl cyclohexane | 7.9 | 97 | Less than 1000 | Less than 1000 |
| | 4-Phenyl phenol | 36.9 | 93 | 1000 | 1000 |
| Ex. 39 | Xylylene diamine | 10.8 | 76 | Less than 1000 | Less than 1000 |
| Ex. 40 | Hydrogenated xylene diamine | 8.6 | 80 | Less than 1000 | Less than 1000 |
| | Bisphenol A | 27.4 | 77 | 1000 | 1000 |

TABLE 37

| | Collected product | Amount of collected product (kg) | Yield (%) | Amount of metallic component (ppm) | Amount of halogen atom (ppm) |
|---|---|---|---|---|---|
| Ex. 41 | 1,3-Bis(2-amino-2-propyl)benzene | 9.6 | 82 | Less than 1000 | Less than 1000 |
| | 2,4-di-(α,α-dimethylbenzyl)phenol | 28.1 | 78 | 1000 | 1000 |
| Ex. 42 | 1,3-Bis(2-amino-2-propyl)cyclohexane | 10.3 | 78 | Less than 1000 | Less than 1000 |
| | 4-Phenyl phenol | 26.2 | 77 | 1000 | 1000 |
| Ex. 43 | 4-Aminomethyl-1,8-octane diamine | 9.1 | 80 | Less than 1000 | Less than 1000 |
| Ex. 44 | 2,4-Diaminotoluene | 8.7 | 83 | Less than 1000 | Less than 1000 |
| | 2,6-Diisopropylphenol | 27.1 | 73 | 1000 | 1000 |
| Ex. 45 | 1,5-Pentamethylene diamine | 4.2 | 94 | Less than 1000 | Less than 1000 |
| | 4-Phenyl phenol | 40.0 | 82 | 1000 | 1000 |
| Ex. 46 | 1,6-Hexamethylene diamine | 6.0 | 96 | Less than 1000 | Less than 1000 |
| | 2,4-di-(α,α-dimethylbenzyl)phenol | 38.1 | 91 | 1000 | 1000 |

TABLE 38

| | Collected product | Amount of collected product (kg) | Yield (%) | Amount of metallic component (ppm) | Amount of halogen atom (ppm) |
|---|---|---|---|---|---|
| Ex. 47 | 1-Amino-3-aminomethyl-3,5,5-trimethyl cyclohexane | 7.9 | 82 | Less than 1000 | Less than 1000 |
| | Styrenated phenol (trisubstituent) | 36.8 | 94 | 1000 | 1000 |
| Ex. 48 | Xylylene diamine | 9.1 | 85 | Less than 1000 | Less than 1000 |
| | 4-Nonyl phenol | 28.1 | 78 | 1000 | 1000 |
| Ex. 49 | Hydrogenated xylene diamine | 8.5 | 82 | Less than 1000 | Less than 1000 |
| | 2,4-Di-tert-amylphenol | 24.1 | 70 | 1000 | 1000 |
| Ex. 50 | 1,3-Bis(2-amino-2-propyl)benzene | 6.0 | 75 | Less than 1000 | Less than 1000 |
| | Bisphenol A | 31.3 | 77 | 1000 | 1000 |
| Ex. 51 | 1,3-Bis(2-amino-2-propyl)cyclohexane | 5.2 | 78 | Less than 1000 | Less than 1000 |
| | 4-Dodecylphenol | 30.4 | 72 | 1000 | 1000 |
| Ex. 52 | 4-Aminomethyl-1,8-octane diamine | 4.4 | 76 | Less than 1000 | Less than 1000 |
| | Styrenated phenol (trisubstituent) | 29.4 | 85 | 1000 | 1000 |

Comparative Example 1

A crude toluene-2,4-diamine was collected by conducting the same method as that of Example 1 except that the condenser B102 was not cooled and the step corresponding to the step (1-2) in Example 1 was not conducted. The yield thereof was 38%. In addition, a crude 4-(1,1,3,3-tetramethylbutyl)phenol was collected at a yield of 43%.

Comparative Example 2

A crude 1-amino-3-aminomethyl-3,5,5-trimethylcyclohexane was collected by conducting the same method as that of Example 2 except that the condenser B203 was not cooled and the step corresponding to the step (2-2) in Example 2 was not conducted. The yield thereof was 41%.

Comparative Example 3

A crude 4, 4'-dicyclohexylmethanediamine was collected by conducting the same method as that of Example 3 except that the condenser 303 was not cooled and the step corresponding to the step (3-2) in Example 3 was not conducted. The yield thereof was 42%.

Comparative Example 4

A crude 1,6-hexamethylenediamine was collected by conducting the same method as that of Example 4 except that the condenser 405 was not cooled and the step corresponding to the step (4-2) in Example 4 was not conducted. The yield thereof was 37%. In addition, a crude 4-(α,α-dimethylbenzyl)phenol was collected at a yield of 46%.

Comparative Example 5

A crude toluene-2,4-diamine was collected by conducting the same method as that of Example 5 except that the condenser 506 was not cooled and the step corresponding to the step (5-2) in Example 5 was not conducted. The yield thereof was 48%. In addition, a crude 4-(1,1,3,3-tetramethylbutyl)phenol was collected at a yield of 35%.

Comparative Example 61

A crude 1,5-pentamethylenediamine was collected by conducting the same method as that of Example 6 except that the condenser 604 was not cooled and the step corresponding to the step (6-2) in Example 6 was not conducted. The yield thereof was 32%.

Comparative Example 7

A crude 1,5-pentamethylenediamine was collected by conducting the same method as that of Example 7 except that 1,5-pentamethylenediamine was not added in the step (7-1). The yield thereof was 22%.

EXPLANATION OF REFERENCE NUMERALS

B1, B2, B3, B4, B5, B20, B21, B22, B23, B24, B25, B26, B30, B31, B32, B33, B34, B35, B36, B40, B41, B42, B43, B44, B50, B51, B52, B53, B54, B55, B60, B61, B62, B63, B64, B70, B71, B72, B73, A1, A3, A4, A5, A6, A7, A8, A9, A17, A18, A19, A20, A21, A22, A23, A24, A31, A32, A40, A41, A42, A43, A44, A45, A46, A47, A48, A49, A50, A51, A61, A62, A63, A64, A65, A70, A71, C1, C4, C5, C20, C21, C22, C30, C31, C32, C40, C41, C42: Line B101, B301, A501, A701, C101: Stirring tank (pressure-resistant reactor)

B201, B302: Reaction tank

B102, B203, B303, B405, B506, B604, B704, A103, A114, A115, A203, A302, A402, A405, A408, A603: Condenser B103, B205, B305, B406, B507, B605, A204, A205, A303, A304, A502, A604, A605, A702, C103: Storage tank B104, B204, B304, B403, B404, B503, B504, B606, C104, C203, C204, C303, C304: Pressure-holding valve B202: Pump B401, B501, C201, C301: Extruder B402, B502, C202, C302: Vent port B505, C305: Receiver B601, B701, C401: Heated evaporation surface B602, B702, A301, C402: Thin-film evaporator B603, B703, C403: Collection part A101, A201: Continuous multistage distillation column A601: Multistage distillation column A102, A401: Thermal decomposition device A111, A112, A113, A202, A403, A406, A409, A602: Reboiler A109, A404, A407: Separation column A110: Purification column

INDUSTRIAL APPLICABILITY

The present invention makes it possible to collect efficiently useful components such as organic amine compounds from high-boiling point components formed as by-products when an isocyanate compound is produced.

The invention claimed is:

1. A method for collecting a compound of general formula (III) from a liquid phase component that is formed as a by-product in a method for producing a compound of general formula (I), comprising:
   step (1): a step for reacting the liquid phase component with at least two active hydrogen-containing compound in a reactor;
   step (2): a step for returning a condensed liquid obtained by cooling gas phase components in the reactor to the reactor;
   step (3): a step for discharging gas phase components that are not condensed in the step (2) outside of the reactor; and
   step (4): a step for discharging, as a liquid phase component inside the reactor, the reaction liquid containing the compound of general formula (III) outside of the reactor,

in the general formula (I), $R^{11}$ represents a monovalent to trivalent organic group, and n11 represents an integer of 1 to 3, and

in the general formula (III), $R^{31}$ represents a monovalent to trivalent organic group, and n31 represents an integer of 1 to 3, wherein the at least two active hydrogen-containing compounds are either water and an aromatic hydroxy compound or urea and an aromatic hydroxy compound, and the gas phase components discharged in step (3) comprises carbon dioxide and ammonia.

2. The collection method according to claim 1, wherein the method for producing a compound of general formula (I) is a method in which the compound of general formula (I) is produced from a carbonic acid derivative, a hydroxy compound and the compound of general formula (III).

3. The collection method according to claim 1, wherein the liquid phase component that is formed as a by-product in the method for producing the compound of general formula (I) is a liquid phase component extracted from a thermal decomposition reactor when a gas phase component comprising the compound of general formula (I) generated by supplying a liquid containing a carbamate produced from a carbonic acid derivative, a hydroxy compound and the compound of general formula (III) to the thermal decomposition reactor and then subjecting the carbamate to thermal decomposition reaction is collected.

4. The collection method according to claim 3, wherein the thermal decomposition reactor comprises: a tubular reactor; and a separation tank in which the liquid phase component and the gas phase component comprising the compound of general formula (I) are separated,
   wherein a flow rate per wetted perimeter of the tubular reactor is 10 kg/hour·m to 1000 kg/hour·m.

5. The collection method according to claim 3, wherein a linear velocity of the gas phase component in a separation tank in which the liquid phase component and the gas phase component comprising the compound of general formula (I) are separated is 10 m/second or less.

6. The collection method according to claim 3, wherein the liquid phase component extracted from the thermal decomposition reactor is supplied to the reactor in which the step (1) is conducted while maintaining the liquid phase component at a temperature of 150° C. to 350° C.

7. The collection method according to claim 1, wherein the liquid phase component comprises a hydroxy compound.

8. The collection method according to claim 1, wherein the liquid phase component comprises a compound having at least one group selected from the group consisting of a group of formula (II-1) and a group of formula (II-2):

9. The collection method according to claim 8, wherein the liquid phase component comprising a high-boiling point compound comprises a hydroxy compound in an amount of 20% by mass to 70% by mass, relative to a total mass of the liquid phase component.

10. The collection method according to claim 1, wherein the liquid phase component has a viscosity at 150° C. of 100 mPa·s or less.

11. The collection method according to claim 1, wherein the reactor is at least one reactor selected from the group consisting of a tank-type reactor, an extruder and a thin-film evaporator.

12. The collection method according to claim 1, wherein at least one of the active hydrogen-containing compound is water, and the gas phase component discharged in the step (3) comprises carbon dioxide.

13. The collection method according to claim 12, wherein the condensed liquid in the step (2) is water.

14. The collection method according to claim 1, wherein the compound of the general formula (III) is further used as the active hydrogen-containing compound.

15. The collection method according to claim 1, further comprising:
step (5): a step for separating the compound of the general formula (III) from the reaction liquid obtained in the step (4); and
step (6): a step for purifying the compound of the general formula (III).

16. The collection method according to claim 15, wherein the compound of the general formula (III) is collected by distillation in the step (6), such that, relative to a total mass of the compound of the general formula (III), an amount of metallic components becomes 1000 ppm by mass or less and an amount of halogen atoms becomes 1000 ppm by mass or less.

17. The collection method according to claim 15, wherein the compound of the general formula (III) collected in the step (6) is recycled to produce the compound of general formula (I).

18. The collection method according to claim 15, wherein the liquid phase component comprises a compound having a group of general formula (IV), a compound of general formula (V) is separated in the step (5) together with the compound of the general formula (III) from the reaction liquid obtained in the step (4), and further comprising:
step (7): a step for purifying the compound of the general formula (V),
wherein the step (7) is conducted after the step (6),

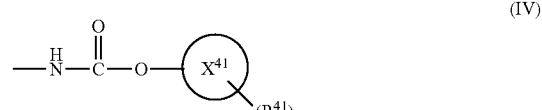

(IV)

(V)

in the general formulae (IV) and (V), $X^{41}$ represents a C6-12 unsubstituted or substituted aromatic hydrocarbon ring or heteroaromatic ring, $R^{41}$ represents a C1-20 alkyl group, which may be substituted with at least one group selected from the group consisting of a phenyl group and a hydroxy phenyl group, an amino group, or a hydroxy group, and n41 represents an integer of 0 to 4, and $R^{41}$ is identical to or different from each other when n41 is 2 or more.

19. The collection method according to claim 18, wherein the compound of the general formula (V) is collected by distillation in the step (7), such that, relative to a total mass of the compound of the general formula (V), an amount of metallic components becomes 1000 ppm by mass or less and an amount of halogen atoms becomes 1000 ppm by mass or less.

20. The collection method according to claim 18, wherein the compound of the general formula (V) collected in the step (7) is recycled to produce the compound of general formula (I).

* * * * *